(12) United States Patent
Spellberg et al.

(10) Patent No.: US 8,747,846 B2
(45) Date of Patent: Jun. 10, 2014

(54) **COMPOSITIONS AND METHODS FOR IMMUNIZATION AGAINST DRUG RESISTANT *ACINETOBACTER BAUMANNII***

(75) Inventors: Brad J. Spellberg, Rancho Palos Verdes, CA (US); Lin Lin, Rancho Palos Verdes, CA (US); Ashraf Ibrahim, Irvine, CA (US); Guanpingsheng Luo, Torrance, CA (US)

(73) Assignee: Los Angeles Biomedical Research Institute at Harbor-UCLA Medical Center, Torrance, CA (US)

( * ) Notice: Subject to any disclaimer, the term of this patent is extended or adjusted under 35 U.S.C. 154(b) by 0 days.

(21) Appl. No.: 13/470,177

(22) Filed: May 11, 2012

(65) Prior Publication Data

US 2012/0301474 A1  Nov. 29, 2012

Related U.S. Application Data

(60) Provisional application No. 61/486,177, filed on May 13, 2011.

(51) Int. Cl.
*A61K 39/00* (2006.01)
*A61K 39/395* (2006.01)

(52) U.S. Cl.
USPC .................................... 424/130.1; 424/139.1

(58) Field of Classification Search
None
See application file for complete search history.

(56) References Cited

U.S. PATENT DOCUMENTS 6,562,958 B1 * 5/2003 Breton et al. ................ 536/23.7
6,713,062 B1 3/2004 Merchant

OTHER PUBLICATIONS

Smith et al (Genes and Development vol. 21, pp. 601-614, 2007).*
Adams et al. "Resistance to colistin in *Acinetobacter baumannii* associated with mutations in the PmrAB two-component system," Antimicrob Agents Chemother 53:3628-3634 (2009).
Alustan et al., "*Acinetobacter Baumannii*: emergence of four strains with novel bla(OXA-51-like) genes in patients with diabetes mellitus," J Chemother 21:290-295 (2009).
Bartual et al., "Development of a multilocus sequence typing scheme for characterization of clinical isolates of *Acinetobacter baumannii*," J Clin Microbiol 43:4382-4390 (2005).
Beavers et al., "Comparison of risk factors for recovery of *Acinetobacter baumannii* during outbreaks at tow Kentucky hospitals 2006," Public Health Rep 124:868-874 (2009).
Bird et al., "Single-Chain Antigen-Binding Proteins," Science 242:423-426 (1988).
Boucher et al., "Bad bugs, no drugs: no ESKAPE! An update from the Infectious Diseases Society of America," Clin Infect Dis 48:1-12 (2009).
Caricato et al., "Risk factors and outcome of *Acinetobacter Baumanii* infection in severe trauma patients," Intensive Care Med 35:1964-1969 (2009).
Choi et al., "*Acinetobacter baumannii* outer membrane protein A targets the nucleus and induces cytotoxicity," Cell Microbiol 10:309-319 (2008).
D'Agata et al., "An outbreak of *Acinetobacter baumannii*: the importance of cross-transmission," Infect Control Hosp Epidemiol 21:588-591 (2000).
Deris et al., "The prevalence and risk factors of nosocomial *Acinetobacter* blood stream infections in tertiary teaching hospital in north-eastern Malaysia," Trop Biomed 26:123-129 (2009).
Dizbay et al., "Nosocomial imipenem-resistant *Acinetobacter baumannii* infections: Epidemiology and risk factors," Scand J Infect Dis, 42:741-746 (2010).
Doi et al., "Extensively drug-resistant *Acinetobacter baumannii*," Emerg Infect Dis 15:980-982 (2009).
Falagas et al., "Pandrug-resistant *Klebsiella pneumoniae, Pseudomonas aeruginosa* and *Acinetobacter baumannii* infections: characteristics and outcome in a series of 28 patients," Int J Antimicrob Agents 32:450-454 (2008).
Furniss et al., "*Acinetobacter* infection is associated with acquired glucose intolerance in burn patients," J Burn Care Rehabil 26:405-408 (2005).
Gordon et al., "A review of clinical and microbiological outcomes following treatment of infections involving mulitidrug-resistant *Acinetobacter baumannii* with tigecycline," J Antimicrob Chemother 63:775-780 (2009).
Hernan et al., "Selection of colistin-resistant *Acinetobacter baumannii* isolates in postneurosurgical meningitis in an intensive care unit with high presence of heteroresistance to colistin," Diagn Microbiol Infect Dis 65:188-191 (2009).
Hidron et al., "NHSN annual update: antimicrobial-resistant pathogens associated with healthcare-associated infections: annual summary of data reported to the National Healthcare Safety Network at the Centers for Disease Control and Prevention, 2006-2007," Infect Control Hosp Epidemiol 29:996-1011 (2008).
Higgins et al., "Global spread of carbapenem-resistant *Acinetobacter baumannii*," J Antimicrob Chemother 65:233-238 (2010).

(Continued)

*Primary Examiner* — Albert Navarro
(74) *Attorney, Agent, or Firm* — Jones Day

(57) ABSTRACT

The present invention provides vaccine compositions comprising OmpA, or antigenic fragments thereof, and related methods of active immunization against *A. baumannii* infection. The invention also provides antibodies and antigen-binding parts thereof that specifically bind to OmpA, and related methods of passive immunization against *A. baumannii* infection. The compositions and methods of the invention are useful for preventing or treating *A. baumannii* infections, including those caused by strains resistant to carbapenems and all other antibiotics except colistin or tigecycline, also referred to as extreme drug resistant (XDR) *A. baumannii* infections, and those resistant to every FDA approved antibiotic, also referred to as pan-drug resistant (PDR) *A. baumannii* infections.

4 Claims, 16 Drawing Sheets
(3 of 16 Drawing Sheet(s) Filed in Color)

(56) References Cited

OTHER PUBLICATIONS

Hoffmann et al., "Increasing resistance of *Acinetobacter* species to imipenem in United States hospitals, 1999-2006," Infect Control Hosp Epidemiol 31:196-197 (2010).
Holliger et al., "'Diabodies': Small bivalent and bispecific antibody fragments," Proc. Natl. Acad. Sci. USA 90:6444-6448 (1993).
Huston et al., "Protein engineering of antibody binding sites: Recovery of specific activity in anti-digoxin single-chain Fv analogue produced in *Escherichia coli*," Proc. Natl. Acad. Sci. USA 85:5879-5883 (1988).
Ibrahim et al., "Deferiprone iron chelation as a novel therapy for experimental mucormycosis," J Antimicrob Chemother 58:1070-1073 (2006).
Ibrahim et al., "The iron chelator deferasirox protects mice from mucormycosis through iron starvation," J Clin Invest 117:2649-2657 (2007).
Ibrahim et al., "The anti-Candida rA1s1p-N vaccine is broadly active against disseminated candidiasis," Infect Immun 74:3039-3041 (2006).
Ibrahim et al., "Vaccination with recombinant N-terminal domain of Als1p improves survival during murine disseminated candidiasis by enhancing cell-mediated, not humoral, immunity," Infect Immun 73:999-1005 (2005).
Jyothisri et al., "Purication and characterization of a major 49 kDa outer membrane protein of *Acinetobacter baumannii*," FEBS Letters, 443(1):57-60 (1999).
Kallen et al., "Multidrug Resistance among Gram-Negative Pathogens Causing Healthcare-Associated Infections Reported to the National Healthcare Safety Network, 2006-2008," Infect Control Hosp Epidemiol 31:528-531 (2010).
Kim et al., "Serum resistance of *Acinetobacter baumannii* through the binding of factor H to outer membrane proteins," FEMS Microbiol Lett 301:224-231 (2009).
King et al., "Serum resistance and biofilm formation in clinical isolates of *Acinetobacter baumannii*," FEMS Immunol Med Microbiol 55:414-421 (2009).
Kipriyanov et al., "Recombinant Single-Chain Fv Fragments Carrying C-Terminal Cysteine Residues: Production of Bivalent and Biotinylated Miniantibodies," Mol Immunol 31:1047-1058 (1994).
Kipriyanov et al. "Single-chain antibody streptavidin fusions: Tetrameric bifunctional scFv-complexes with biotin binding activity and enhanced affinity to antigen," Human Antibodies and Hybridomas 6:93-101 (1995).
Lautenbach et al., "Epidemiology and impact of imipenem resistance in *Acinetobacter baumannii*," Infect Control Hosp Epidemiol 30:1186-1192 (2009).
Lindblad, E.B., "Aluminum adjuvants—in retrospect and prospect," Vaccine 22:3658-3668 (2004).
Lindblad, E.B., "Aluminum compounds for use in vaccines," Immunol Cell Biol 82:497-505 (2004).
Livermore et al., "Antimicrobial treatment and clinical outcome for infections with carbapenem- and multiply-resistant *Acinetobacter baumannii* around London," Int J Antimicrob Agents 35:19-24 (2010).
Luo et al., "*Candida albicans* Hyr1p confers resistance to neutrophil killing and is a potential vaccine target," J Infect Dis 201:1718-1728 (2010).
Maass et al., "Alpaca (Lama Pacos) as a convenient source of recombinant camelid heavy chain antibodies," J Immunol Methods, 324:13-25 (2007).
McConnell et al., "Vaccination with outer membrane complexes elicits rapid protective immunity to multidrug-resistant *Acinetobacter baumannii*," Infect Immun 79(1):518-526 (2010).
McConnell et al., "Active and passive immunization against *Acinetobacter baumannii* using an inactivated whole cell vaccine," Vaccine 29:1-5 (2010).
McConnell et al., "Expression, purification, and refolding of biologically active *Acinetobacter baumannii* OmpA from *Escherichia coli* inclusion bodies," Protein Expr Purif 77(1):98-103 (2011).
Mera et al., "*Acinetobacter baumannii* 2002-2008: Increase of Carbapenem-Associated Multiclass Resistance in the United States," Microb Drug Resist 16:209-215 (2010).
Metan et al., "Factors influencing survival in patients with multidrug-resistant *Acinetobacter bacteraemia*,"Eur J Intern Med 20:540-544 (2009).
Molloy et al., "Proteomic analysis of the *Escherichia coli* outer membrane," Eur J Biochem 267:2871-2881 (2000).
Munoz-Price et al., "Clinical Outcomes of Carbapenem-Resistant *Acinetobacter baumannii* Bloodstream Infections: Study of a 2-State Monoclonal Outbreak," Infect Control Hosp Epidemiol 1(10):1057-1062 (2010).
Muyldermans et al., "Recognition of antigens by single-domain antibody fragments: the superfluous luxury of paired domains," TIBS 26:230-235 (2001).
Park et al., "Independent emergence of colistin-resistant *Acinetobacter* spp. isolates from Korea," Diagn Microbiol Infect Dis 64:43-51 (2009).
Perez et al., "Global challenge of multidrug-resistant *Acinetobacter baumannii*," Antimicrob Agents Chemother 51:3471-3484 (2007).
Perez et al., "Antibiotic resistance determinants in *Acinetobacter* spp and clinical outcomes in patients from a major military treatment facility," Am J Infect Control 38:63-65 (2010).
Piechaud et al., "Studies of 26 strains of *Moraxella iwoffi*," Ann Inst Pasteur (Paris) 80:97-99 (1951).
Pitarch et al., "Decoding serological response to *Candida* cell wall immunome into novel diagnostic, prognostic, and therapeutic candidates for systemic candidiasis by proteomic and bioinformatic analyses," Mol Cell Proteomics 5:79-96 (2006).
Pitarch et al., "Two-dimensional gel electrophoresis as analytical tool for identifying *Candida albicans* immunogenic proteins," Electrophoresis 20:1001-1010 (1999).
Poljak et al., "Production and structure of diabodies," Structure 2:1121-1123 (1994).
Qiu et al., "Role of NADPH phagocyte oxidase in host defense against acute respiratory *Acinetobacter baumannii* infection in mice," Infect Immun 77:1015-1021 (2009).
Rosenthal et al., "International Nosocomial Infection Control Consortium (INICC) report, data summary for 2003-2008, issued Jun. 2009," Am J Infect Control 38:95-104 (2010).
Russo et al., "Rat pneumonia and soft-tissue infection models for the study of *Acinetobacter baumannii* biology," Infect Immun 76(8):3577-3586 (2008).
Russo et al., "Penicillin-binding protein 7/8 contributes to the survival of *Acinetobacter baumannii* in vitro and in vivo," J Infect Dis 199:513-521 (2009).
Shevchenko et al., "Linking genome and proteome by mass spectrometry: large-scale indentification of yeast proteins from two dimensional gels," Proc Natl Acad Sci U S A 93:14440-14445 (1996).
Shevchenko et al., "Mass spectrometric sequencing of proteins silver-strained polyacrylamide gels," Anal Chem 68:850-858 (1996).
Soares et al., "2-DE analysis indicates that *Acinetobacter baumannii* displays a robust and versatile metabolism," Proteome Sci 7:37 (2009).
Spellberg et al., "Combating Antimicrobial Resistance: Policy Recommendations to Save Lives," Clin Infect Dis 52(S5):397-428 (2011).
Spellberg et al., "Combination therapy with amphotericin B lipid complex and caspofungin acetate of disseminated zygomycosis in diabetic ketoacidotic mice," Antimicrob Agents Chemother 49:830-832 (2005).
Spellberg et al., "The epidemic of antibiotic-resistant infections: a call to action for the medical community from the Infectious Diseases Society of America," Clin Infect Dis 46:155-164 (2008).
Spellberg et al., "The anti-fungal rAls3p-N vaccine protects mice against the bacterium *Staphylococcus aureus*," Infect Immun 76:4574-4580 (2008).
Spellberg et al., "Efficacy of the anti-*Candida* rAls3p-N or rAls1p-N vaccines against disseminated and mucosal candidiasis," J Infect Dis 194:256-260 (2006).
Spellberg et al., "The anti-*Candida albicans* vaccine composed of the recombinant N terminus of Als1p reduces fungal burden and

(56) References Cited

OTHER PUBLICATIONS improves survival in both immunocompetent and immunocompromised mice," Infect Immun 73(9):6191-6193 (2005).

Sunenshine et al., "Multidrug-resistant *Acinetobacter* infection morality rate and length of hospitalization," Emerg Infect Dis 13:97-103 (2007).

Taylor et al., "A transgenic mouse that expresses a diversity of human sequence heavy and light chain immunoglobulins," Nucl Acids Res. 20:6287-6295 (1992).

Tian et al., "Identification of diverse OXA-40 group carbapenemases, including a novel variant, OXA-160, from *Acinetobacter baumannii* in Pennsylvania," Antimicrob Agents Chemother 55:429-432 (2011).

Tseng et al, "Prognosis of adult patients with bacteremia caused by extensively resistant *Acinetobacter baumannii*," Diagn Microbiol Infect Dis 59:181-190 (2007).

Valencia et al., "Nosocomial outbreak of infection with pan-drug-resistant *Acinetobacter baumannii* in a tertiary care university hospital," Infect Control Hosp Epidemiol 30:257-263 (2009).

Von Faassen et al., "Neutrophils play an important role in host resistance to respiratory infection with *Acinetobacter baumannii* in mice," Infect Immun 75:5597-5608 (2007).

Walker et al., "Environment. Looming global-scale failures and missing institutions," Science 325:1345-1346 (2009).

Wang et al., "In vitro activity of tigecycline and comparators on *Acinetobacter* spp. isolates collected from patients with bacteremia and MIC change during the Tigecycline Evaluation and Surveillance Trial, 2004 to 2008," Diagn Microbiol Infect Dis 68:73-79 (2010).

Ward et al., "Binding activities of a repertoire of single immunoglobulin variable domains secreated from *Escherichia coli*," Nature 341:544-546 (1989).

Yau et al., "Selection of hapten-specific single-domain antibodies from a non-immunized llama ribosome display library," J Immunol Methods, 281:161-175 (2003).

\* cited by examiner

```
ATCC17978    MLVAAPLAAANAGVTVTPLLLGYTFQDSQHNNGGKDGNLTNSPELQDDLFVGAALGIELT
HUMC1        MLVAAPLAAANAGVTVTPLLLGYTFQDSQHNNGGKDGNLTNSPELQDDLFVGAALGIELT
HUMC4        MLVAAPLAAANAGVTVTPLLLGYTFQDSQHNNGGKDGNLTNSPELQDDLFVGAALGIELT
HUMC6        MLVAAPLAAANAGVTVTPLLLGYTFQDSQHNNGGKDGNLTNSPELQDDLFVGAALGIELT
HUMC12       MLVAAPLAAANAGVTVTPLLLGYTFQDSQHNNGGKDGNLTNSPELQDDLFVGAALGIELT
HUMC5        MLVAAPLAAAKAGVTVTPLLLGYTFQDSQHNNGGKDGNLTNSPELQDDLFVGAALGIELT
             *********:******************************.******************

ATCC17978    PWLGFEAEYNQVKGDVDGASAGAEYKQKQINGNFYVTSDLITKNYDSKIKPYVLLGAGHY
HUMC1        PWLGFEAEYNQVKGDVDGASAGAEYKQKQINGNFYVTSDLITKNYDSKIKPYVLLGAGHY
HUMC4        PWLGFEAEYNQVKGDVDGASAGAEYKQKQINGNFYVTSDLITKNYDSKIKPYVLLGAGHY
HUMC6        PWLGFEAEYNQVKGDVDGASAGAEYKQKQINGNFYVTSDLITKNYDSKIKPYVLLGAGHY
HUMC12       PWLGFEAEYNQVKGDVDGASAGAEYKQKQINGNFYVTSDLITKNYDSKIKPYVLLGAGHY
HUMC5        PWLGFEAEYNQVKGDVDGASAGAEYKQKQINGNFYVTSDLITKNYDSKIKPYVLLGAGHY
             ************************************************************

ATCC17978    KYDFDGVNRGTRGTSEEGTLGNAGVGAFWRLNDALSLRTEARATYNADEEFWNYTALAGL
HUMC1        KYDFDGVNRGTRGTSEEGTLGNAGVGAFWRLNDALSLRTEARATYNADEEFWNYTALAGL
HUMC4        KYDFDGVNRGTRGTSEEGTLGNAGVGAFWRLNDALSLRTEARATYNADEEFWNYTALAGL
HUMC6        KYDFDGVNRGTRGTSEEGTLGNAGVGAFWRLNDALSLRTEARATYNADEEFWNYTALAGL
HUMC12       KYDFDGVNRGTRGTSEEGTLGNAGVGAFWRLNDALSLRTEARATYNADEEFWNYTALAGL
HUMC5        KYDFDGVNRGTRGTSEEGTLGNAGVGAFWRLNDALSLRTEARATYNADEEFWNYTALAGL
             ************************************************************

ATCC17978    NVVLGGHLKPAAPVVEVAPVEPTPVTPQPQELTEDLNMELRVFFDTNKSNIKDQYKPEIA
HUMC1        NVVLGGHLKPAAPVVEVAPVEPTPVAPQPQELTEDLNMELRVFFDTNKSNIKDQYKPEIA
HUMC4        NVVLGGHLKPAAPVVEVAPVEPTPVAPQPQELTEDLNMELRVFFDTNKSNIKDQYKPEIA
HUMC6        NVVLGGHLKPAAPVVEVAPVEPTPVAPQPQELTEDLNMELRVFFDTNKSNIKDQYKPEIA
HUMC12       NVVLGGHLKPAAPVVEVAPVEPTPVAPQPQELTEDLNMELRVFFDTNKSNIKDQYKPEIA
HUMC5        NVVLGGHLKPAAPVVEVAPVEPTPVAPQPQELTEDLNMELRVFFDTNKSNIKDQYKPEIA
             *************************.**********************************

ATCC17978    KVAEKLSEYPNATARIEGHTDNTGPRKLNERLSLARANSVKSALVNEYNVDASRLSTQGF
HUMC1        KVAEKLSEYPNATARIEGHTDNTGPRKLNERLSLARANSVKSALVNEYNVDASRLSTQGF
HUMC4        KVAEKLSEYPNATARIEGHTDNTGPRKLNERLSLARANSVKSALVNEYNVDASRLSTQGF
HUMC6        KVAEKLSEYPNATARIEGHTDNTGPRKLNERLSLARANSVKSALVNEYNVDASRLSTQGF
HUMC12       KVAEKLSEYPNATARIEGHTDNTGPRKLNERLSLARANSVKSALVNEYNVDASRLSTQGF
HUMC5        KVAEKLSEYPNATARIEGHTDNTGPRKLNERLSLARANSVKSALVNEYNVDASRLSTQGF
             ************************************************************

ATCC17978    AWDQPIADNKTKEGRAMNRRVFATITGSRTVVVQPGQEAAAPAAAQ
HUMC1        AWDQPIADNKTKEGRAMNRRVFATITGSRTVVVQPGQEAAAPAAAQ
HUMC4        AWDQPIADNKTKEGRAMNRRVFATITGSRTVVVQPGQEAAAPAAAQ
HUMC6        AWDQPIADNKTKEGRAMNRRVFATITGSRTVVVQPGQEAAAPAAAQ
HUMC12       AWDQPIADNKTKEGRAMNRRVFATITGSRTVVVQPGQEAAAPAAAQ
HUMC5        AWDQPIADNKTKEGRAMNRRVFATITGSRTVVVQPGQEAAAPAAAQ
             **********************************************
```

Figure 4

OmpA Immunogenic Epitope Mapping Analysis

Major Immunogenic Epitopes

1. SPOTs 86-92    aa   265PRKLNERLSLARANSV280
2. SPOTs 102-105  aa   307ADNKTKEGRAMNR319
3. SPOTs 107-108  aa   319RRVFATITGSRTV331
4. SPOTs 40-41    aa   121KYDFDGVNRGTRG133

```
CLUSTAL format alignment by MAFFT (v6.821b)

ATCC17978   ------------------------------MLVAAPLAAANAGVTVTP
HUMC1       ------------------------------MLVAAPLAAANAGVTVTP
HUMC4       ------------------------------MLVAAPLAAANAGVTVTP
HUMC6       ------------------------------MLVAAPLAAANAGVTVTP
HUMC12      ------------------------------MLVAAPLAAANAGVTVTP
HUMC5       ------------------------------MLVAAPLAAAKAGVTVTP
Prior art   MAYCGLELEQQFLSLEDKSMKMSRIALAMLVAAPAAANAGVTVTPLMLGYTFQDTQHNN
                                          *****   *******  .    .  .

ATCC17978   GGKDGNLTNGPELQDDLFVGAALGIELTPWLGFEAEYNQVKGDVDGASAGAEYKQKQI
HUMC1       GGKDGNLTNSPELQDDLFVGAALGIELTPWLGFEAEYNQVKGDVDGASAGAEYKQKQI
HUMC4       GGKDGNLTNSPELQDDLFVGAALGIELTPWLGFEAEYNQVKGDVDGASAGAEYKQKQI
HUMC6       GGKDGNLTNSPELQDDLFVGAALGIELTPWLGFEAEYNQVKGDVDGASAGAEYKQKQI
HUMC12      GGKDGNLTNSPELQDDLFVGAALGIELTPWLGFEAEYNQVKGDVDGASAGAEYKQKQI
HUMC5       GGKDGNLTNSPELQDDLFVGAALGIELTPWLGFEAEYNQVKGDVDGASAGAEYKQKQI
Prior art   NGNDGELTSSPELQDDLFVGAAIGVELTPWLGFEAEYSQVKGDVDGAAEGAEYKGQNIAG
              .:**:**..*********** *:************.**********: ****  :  *

ATCC17978                                           TRGTSEEGTLGNAGVGAFWRLN
HUMC1                                               TRGTSEEGTLGNAGVGAFWRLN
HUMC4                                               TRGTSEEGTLGNAGVGAFWRLN
HUMC6                                               TRGTSEEGTLGNAGVGAFWRLN
HUMC12                                              TRGTSEEGTLGNAGVGAFWRLN
HUMC5                                               TRGTSEEGTLGNAGVGAFWRLN
Prior art   NFYATSDYTGNYDSKYKPYMLLGAGHYKYSFRGVRRGTRGNEEEGTLGNAGVGAFWHEN
                                                      ****.********** :*

ATCC17978   ADEEFWNYTALAGLNVVLGGHLKPAAPVVEVAPVEP-TPVTPQPQE
HUMC1       ADEEFWNYTALAGLNVVLGGHLKPAAPVVEVAPVEP-TPVAPQPQE
HUMC4       ADEEFWNYTALAGLNVVLGGHLKPAAPVVEVAPVEP-TPVAPQPQE
HUMC6       ADEEFWNYTALAGLNVVLGGHLKPAAPVVEVAPVEP-TPVAPQPQE
HUMC12      ADEEFWNYTALAGLNVVLGGHLKPAAPVVEVAPVEP-TPVAPQPQE
HUMC5       ADEEFWNYTALAGLNVVLGGHLKPAAPVVEVAPVEP-TPVAPQPQE
Prior art   DALALRTEARETYHFDEKFWNYTALAGLNVVLGGRLKPAAPVVEVAPVEFVTPVAPPPQE
                *:******.**:  ***:***********************  ***.* ***

ATCC17978   LTEDLNMELRVFFDTNKSNIKDQYKPEIAKVAEKLSEYPNATARIEGHTDNTG
HUMC1       LTEDLNMELRVFFDTNKSNIKDQYKPEIAKVAEKLSEYPNATARIEGHTDNTG
HUMC4       LTEDLNMELRVFFDTNKSNIKDQYKPEIAKVAEKLSEYPNATARIEGHTDNTG
HUMC6       LTEDLNMELRVFFDTNKSNIKDQYKPEIAKVAEKLSEYPNATARIEGHTDNTG
HUMC12      LTEDLNMELRVFFDTNKSNIKDQYKPEIAKVAEKLSEYPNATARIEGHTDNTG
HUMC5       LTEDLNMELRVFFDTNKSNIKDQYKPEIAKVAEKLSEYPNATARIEGHTDNTG
Prior art   LTEDLNMELRVFFDTNKSNIKDQYKPEIAKVAEKLVEYPNATARIEGHTDNTGPRALNER
            **********************************  ****************   ****

ATCC17978   KSALVNEYNVDASRLSTQGFAWDQPI
HUMC1       KSALVNEYNVDASRLSTQGFAWDQPI
HUMC4       KSALVNEYNVDASRLSTQGFAWDQPI
HUMC6       KSALVNEYNVDASRLSTQGFAWDQPI
HUMC12      KSALVNEYNVDASRLSTQGFAWDQPI
HUMC5       KSALVNEYNVDASRLSTQGFAWDQPI
Prior art   LSLARANSVKSSLVNEYNVDASRLSTQGFAWDQPIADNNTKEGRAMNRRVFATITGSRTV
                       .:**************************

ATCC17978   VVQPGQEAAAPAAAQ
HUMC1       VVQPGQEAAAPAAAQ
HUMC4       VVQPGQEAAAPAAAQ
HUMC6       VVQPGQEAAAPAAAQ
HUMC12      VVQPGQEAAAPAAAQ
HUMC5       VVQPGQEAAAPAAAQ
Prior art   LAE-------QPVAQ
            :.:       ..**
```

Figure 13

SEQUENCE LISTING

```
<160> NUMBER OF SEQ ID NOS: 29

<210> SEQ ID NO 1
<211> LENGTH: 346
<212> TYPE: PRT
<213> ORGANISM: Acinetobacter baumannii

<400> SEQUENCE: 1

Met Leu Val Ala Ala Pro Leu Ala Ala Ala Asn Ala Gly Val Thr Val
1               5                   10                  15

Thr Pro Leu Leu Leu Gly Tyr Thr Phe Gln Asp Ser Gln His Asn Asn
            20                  25                  30

Gly Gly Lys Asp Gly Asn Leu Thr Asn Gly Pro Glu Leu Gln Asp Asp
        35                  40                  45

Leu Phe Val Gly Ala Ala Leu Gly Ile Glu Leu Thr Pro Trp Leu Gly
    50                  55                  60

Phe Glu Ala Glu Tyr Asn Gln Val Lys Gly Asp Val Asp Gly Ala Ser
65                  70                  75                  80

Ala Gly Ala Glu Tyr Lys Gln Lys Gln Ile Asn Gly Asn Phe Tyr Val
                85                  90                  95

Thr Ser Asp Leu Ile Thr Lys Asn Tyr Asp Ser Lys Ile Lys Pro Tyr
            100                 105                 110

Val Leu Leu Gly Ala Gly His Tyr Lys Tyr Asp Phe Asp Gly Val Asn
        115                 120                 125

Arg Gly Thr Arg Gly Thr Ser Glu Glu Gly Thr Leu Gly Asn Ala Gly
    130                 135                 140

Val Gly Ala Phe Trp Arg Leu Asn Asp Ala Leu Ser Leu Arg Thr Glu
145                 150                 155                 160

Ala Arg Ala Thr Tyr Asn Ala Asp Glu Glu Phe Trp Asn Tyr Thr Ala
                165                 170                 175

Leu Ala Gly Leu Asn Val Val Leu Gly Gly His Leu Lys Pro Ala Ala
            180                 185                 190

Pro Val Val Glu Val Ala Pro Val Glu Pro Thr Pro Val Thr Pro Gln
        195                 200                 205

Pro Gln Glu Leu Thr Glu Asp Leu Asn Met Glu Leu Arg Val Phe Phe
```

```
               210                 215                 220
Asp Thr Asn Lys Ser Asn Ile Lys Asp Gln Tyr Lys Pro Glu Ile Ala
225                 230                 235                 240

Lys Val Ala Glu Lys Leu Ser Glu Tyr Pro Asn Ala Thr Ala Arg Ile
                245                 250                 255

Glu Gly His Thr Asp Asn Thr Gly Pro Arg Lys Leu Asn Glu Arg Leu
                260                 265                 270

Ser Leu Ala Arg Ala Asn Ser Val Lys Ser Ala Leu Val Asn Glu Tyr
                275                 280                 285

Asn Val Asp Ala Ser Arg Leu Ser Thr Gln Gly Phe Ala Trp Asp Gln
                290                 295                 300

Pro Ile Ala Asp Asn Lys Thr Lys Glu Gly Arg Ala Met Asn Arg Arg
305                 310                 315                 320

Val Phe Ala Thr Ile Thr Gly Ser Arg Thr Val Val Gln Pro Gly
                325                 330                 335

Gln Glu Ala Ala Ala Pro Ala Ala Ala Gln
                340                 345
```

<210> SEQ ID NO 2
<211> LENGTH: 346
<212> TYPE: PRT
<213> ORGANISM: Acinetobacter baumannii

<400> SEQUENCE: 2

```
Met Leu Val Ala Ala Pro Leu Ala Ala Ala Asn Ala Gly Val Thr Val
1               5                   10                  15

Thr Pro Leu Leu Leu Gly Tyr Thr Phe Gln Asp Ser Gln His Asn Asn
                20                  25                  30

Gly Gly Lys Asp Gly Asn Leu Thr Asn Ser Pro Glu Leu Gln Asp Asp
            35                  40                  45

Leu Phe Val Gly Ala Ala Leu Gly Ile Glu Leu Thr Pro Trp Leu Gly
        50                  55                  60

Phe Glu Ala Glu Tyr Asn Gln Val Lys Gly Asp Val Asp Gly Ala Ser
65                  70                  75                  80

Ala Gly Ala Glu Tyr Lys Gln Lys Gln Ile Asn Gly Asn Phe Tyr Val
                85                  90                  95

Thr Ser Asp Leu Ile Thr Lys Asn Tyr Asp Ser Lys Ile Lys Pro Tyr
                100                 105                 110

Val Leu Leu Gly Ala Gly His Tyr Lys Tyr Asp Phe Asp Gly Val Asn
                115                 120                 125

Arg Gly Thr Arg Gly Thr Ser Glu Glu Gly Thr Leu Gly Asn Ala Gly
                130                 135                 140

Val Gly Ala Phe Trp Arg Leu Asn Asp Ala Leu Ser Leu Arg Thr Glu
145                 150                 155                 160

Ala Arg Ala Thr Tyr Asn Ala Asp Glu Glu Phe Trp Asn Tyr Thr Ala
                165                 170                 175

Leu Ala Gly Leu Asn Val Val Leu Gly Gly His Leu Lys Pro Ala Ala
                180                 185                 190

Pro Val Val Glu Val Ala Pro Val Glu Pro Thr Pro Val Ala Pro Gln
                195                 200                 205

Pro Gln Glu Leu Thr Glu Asp Leu Asn Met Glu Leu Arg Val Phe Phe
                210                 215                 220

Asp Thr Asn Lys Ser Asn Ile Lys Asp Gln Tyr Lys Pro Glu Ile Ala
225                 230                 235                 240

Lys Val Ala Glu Lys Leu Ser Glu Tyr Pro Asn Ala Thr Ala Arg Ile
```

```
                       245                 250                 255
Glu Gly His Thr Asp Asn Thr Gly Pro Arg Lys Leu Asn Glu Arg Leu
                260                 265                 270

Ser Leu Ala Arg Ala Asn Ser Val Lys Ser Ala Leu Val Asn Glu Tyr
            275                 280                 285

Asn Val Asp Ala Ser Arg Leu Ser Thr Gln Gly Phe Ala Trp Asp Gln
        290                 295                 300

Pro Ile Ala Asp Asn Lys Thr Lys Glu Gly Arg Ala Met Asn Arg Arg
305                 310                 315                 320

Val Phe Ala Thr Ile Thr Gly Ser Arg Thr Val Val Gln Pro Gly
                325                 330                 335

Gln Glu Ala Ala Ala Pro Ala Ala Ala Gln
                340                 345

<210> SEQ ID NO 3
<211> LENGTH: 346
<212> TYPE: PRT
<213> ORGANISM: Acinetobacter baumannii

<400> SEQUENCE: 3

Met Leu Val Ala Ala Pro Leu Ala Ala Asn Ala Gly Val Thr Val
1               5                   10                  15

Thr Pro Leu Leu Leu Gly Tyr Thr Phe Gln Asp Ser Gln His Asn Asn
            20                  25                  30

Gly Gly Lys Asp Gly Asn Leu Thr Asn Ser Pro Glu Leu Gln Asp Asp
        35                  40                  45

Leu Phe Val Gly Ala Ala Leu Gly Ile Glu Leu Thr Pro Trp Leu Gly
    50                  55                  60

Phe Glu Ala Glu Tyr Asn Gln Val Lys Gly Asp Val Asp Gly Ala Ser
65                  70                  75                  80

Ala Gly Ala Glu Tyr Lys Gln Lys Gln Ile Asn Gly Asn Phe Tyr Val
                85                  90                  95

Thr Ser Asp Leu Ile Thr Lys Asn Tyr Asp Ser Lys Ile Lys Pro Tyr
            100                 105                 110

Val Leu Leu Gly Ala Gly His Tyr Lys Tyr Asp Phe Asp Gly Val Asn
        115                 120                 125

Arg Gly Thr Arg Gly Thr Ser Glu Glu Gly Thr Leu Gly Asn Ala Gly
    130                 135                 140

Val Gly Ala Phe Trp Arg Leu Asn Asp Ala Leu Ser Leu Arg Thr Glu
145                 150                 155                 160

Ala Arg Ala Thr Tyr Asn Ala Asp Glu Glu Phe Trp Asn Tyr Thr Ala
                165                 170                 175

Leu Ala Gly Leu Asn Val Val Leu Gly Gly His Leu Lys Pro Ala Ala
            180                 185                 190

Pro Val Val Glu Val Ala Pro Val Glu Pro Thr Pro Val Ala Pro Gln
        195                 200                 205

Pro Gln Glu Leu Thr Glu Asp Leu Asn Met Glu Leu Arg Val Phe Phe
    210                 215                 220

Asp Thr Asn Lys Ser Asn Ile Lys Asp Gln Tyr Lys Pro Glu Ile Ala
225                 230                 235                 240

Lys Val Ala Glu Lys Leu Ser Glu Tyr Pro Asn Ala Thr Ala Arg Ile
                245                 250                 255

Glu Gly His Thr Asp Asn Thr Gly Pro Arg Lys Leu Asn Glu Arg Leu
            260                 265                 270

Ser Leu Ala Arg Ala Asn Ser Val Lys Ser Ala Leu Val Asn Glu Tyr
```

```
                275                 280                 285
Asn Val Asp Ala Ser Arg Leu Ser Thr Gln Gly Phe Ala Trp Asp Gln
            290                 295                 300

Pro Ile Ala Asp Asn Lys Thr Lys Glu Gly Arg Ala Met Asn Arg Arg
305                 310                 315                 320

Val Phe Ala Thr Ile Thr Gly Ser Arg Thr Val Val Gln Pro Gly
                325                 330                 335

Gln Glu Ala Ala Ala Pro Ala Ala Gln
            340                 345

<210> SEQ ID NO 4
<211> LENGTH: 346
<212> TYPE: PRT
<213> ORGANISM: Acinetobacter baumannii

<400> SEQUENCE: 4

Met Leu Val Ala Ala Pro Leu Ala Ala Asn Ala Gly Val Thr Val
1               5                   10                  15

Thr Pro Leu Leu Leu Gly Tyr Thr Phe Gln Asp Ser Gln His Asn Asn
                20                  25                  30

Gly Gly Lys Asp Gly Asn Leu Thr Asn Ser Pro Glu Leu Gln Asp Asp
            35                  40                  45

Leu Phe Val Gly Ala Ala Leu Gly Ile Glu Leu Thr Pro Trp Leu Gly
50                  55                  60

Phe Glu Ala Glu Tyr Asn Gln Val Lys Gly Asp Val Asp Gly Ala Ser
65                  70                  75                  80

Ala Gly Ala Glu Tyr Lys Gln Lys Gln Ile Asn Gly Asn Phe Tyr Val
                85                  90                  95

Thr Ser Asp Leu Ile Thr Lys Asn Tyr Asp Ser Lys Ile Lys Pro Tyr
                100                 105                 110

Val Leu Leu Gly Ala Gly His Tyr Lys Tyr Asp Phe Asp Gly Val Asn
                115                 120                 125

Arg Gly Thr Arg Gly Thr Ser Glu Glu Gly Thr Leu Gly Asn Ala Gly
            130                 135                 140

Val Gly Ala Phe Trp Arg Leu Asn Asp Ala Leu Ser Leu Arg Thr Glu
145                 150                 155                 160

Ala Arg Ala Thr Tyr Asn Ala Asp Glu Glu Phe Trp Asn Tyr Thr Ala
                165                 170                 175

Leu Ala Gly Leu Asn Val Val Leu Gly Gly His Leu Lys Pro Ala Ala
            180                 185                 190

Pro Val Val Glu Val Ala Pro Val Glu Pro Thr Pro Val Ala Pro Gln
        195                 200                 205

Pro Gln Glu Leu Thr Glu Asp Leu Asn Met Glu Leu Arg Val Phe Phe
        210                 215                 220

Asp Thr Asn Lys Ser Asn Ile Lys Asp Gln Tyr Lys Pro Glu Ile Ala
225                 230                 235                 240

Lys Val Ala Glu Lys Leu Ser Glu Tyr Pro Asn Ala Thr Ala Arg Ile
                245                 250                 255

Glu Gly His Thr Asp Asn Thr Gly Pro Arg Lys Leu Asn Glu Arg Leu
                260                 265                 270

Ser Leu Ala Arg Ala Asn Ser Val Lys Ser Ala Leu Val Asn Glu Tyr
            275                 280                 285

Asn Val Asp Ala Ser Arg Leu Ser Thr Gln Gly Phe Ala Trp Asp Gln
            290                 295                 300

Pro Ile Ala Asp Asn Lys Thr Lys Glu Gly Arg Ala Met Asn Arg Arg
```

```
                305                 310                 315                 320
Val Phe Ala Thr Ile Thr Gly Ser Arg Thr Val Val Gln Pro Gly
                325                 330                 335

Gln Glu Ala Ala Ala Pro Ala Ala Ala Gln
                340                 345

<210> SEQ ID NO 5
<211> LENGTH: 346
<212> TYPE: PRT
<213> ORGANISM: Acinetobacter baumannii

<400> SEQUENCE: 5

Met Leu Val Ala Ala Pro Leu Ala Ala Asn Ala Gly Val Thr Val
1               5                   10                  15

Thr Pro Leu Leu Leu Gly Tyr Thr Phe Gln Asp Ser Gln His Asn Asn
                20                  25                  30

Gly Gly Lys Asp Gly Asn Leu Thr Asn Ser Pro Glu Leu Gln Asp Asp
                35                  40                  45

Leu Phe Val Gly Ala Ala Leu Gly Ile Glu Leu Thr Pro Trp Leu Gly
50                  55                  60

Phe Glu Ala Glu Tyr Asn Gln Val Lys Gly Asp Val Asp Gly Ala Ser
65                  70                  75                  80

Ala Gly Ala Glu Tyr Lys Gln Lys Gln Ile Asn Gly Asn Phe Tyr Val
                85                  90                  95

Thr Ser Asp Leu Ile Thr Lys Asn Tyr Asp Ser Lys Ile Lys Pro Tyr
                100                 105                 110

Val Leu Leu Gly Ala Gly His Tyr Lys Tyr Asp Phe Asp Gly Val Asn
                115                 120                 125

Arg Gly Thr Arg Gly Thr Ser Glu Glu Gly Thr Leu Gly Asn Ala Gly
                130                 135                 140

Val Gly Ala Phe Trp Arg Leu Asn Asp Ala Leu Ser Leu Arg Thr Glu
145                 150                 155                 160

Ala Arg Ala Thr Tyr Asn Ala Asp Glu Glu Phe Trp Asn Tyr Thr Ala
                165                 170                 175

Leu Ala Gly Leu Asn Val Val Leu Gly Gly His Leu Lys Pro Ala Ala
                180                 185                 190

Pro Val Val Glu Val Ala Pro Val Glu Thr Pro Val Ala Pro Gln
                195                 200                 205

Pro Gln Glu Leu Thr Glu Asp Leu Asn Met Glu Leu Arg Val Phe Phe
                210                 215                 220

Asp Thr Asn Lys Ser Asn Ile Lys Asp Gln Tyr Lys Pro Glu Ile Ala
225                 230                 235                 240

Lys Val Ala Glu Lys Leu Ser Glu Tyr Pro Asn Ala Thr Ala Arg Ile
                245                 250                 255

Glu Gly His Thr Asp Asn Thr Gly Pro Arg Lys Leu Asn Glu Arg Leu
                260                 265                 270

Ser Leu Ala Arg Ala Asn Ser Val Lys Ser Ala Leu Val Asn Glu Tyr
                275                 280                 285

Asn Val Asp Ala Ser Arg Leu Ser Thr Gln Gly Phe Ala Trp Asp Gln
                290                 295                 300

Pro Ile Ala Asp Asn Lys Thr Lys Glu Gly Arg Ala Met Asn Arg Arg
305                 310                 315                 320

Val Phe Ala Thr Ile Thr Gly Ser Arg Thr Val Val Gln Pro Gly
                325                 330                 335

Gln Glu Ala Ala Ala Pro Ala Ala Ala Gln
```

-continued

```
                        340                 345

<210> SEQ ID NO 6
<211> LENGTH: 346
<212> TYPE: PRT
<213> ORGANISM: Acinetobacter baumannii

<400> SEQUENCE: 6

Met Leu Val Ala Ala Pro Leu Ala Ala Lys Ala Gly Val Thr Val
1               5                   10                  15

Thr Pro Leu Leu Leu Gly Tyr Thr Phe Gln Asp Ser Gln His Asn Asn
            20                  25                  30

Gly Gly Lys Asp Gly Asn Leu Thr Asn Ser Pro Glu Leu Gln Asp Asp
        35                  40                  45

Leu Phe Val Gly Ala Ala Leu Gly Ile Glu Leu Thr Pro Trp Leu Gly
    50                  55                  60

Phe Glu Ala Glu Tyr Asn Gln Val Lys Gly Asp Val Asp Gly Ala Ser
65                  70                  75                  80

Ala Gly Ala Glu Tyr Lys Gln Lys Gln Ile Asn Gly Asn Phe Tyr Val
                85                  90                  95

Thr Ser Asp Leu Ile Thr Lys Asn Tyr Asp Ser Lys Ile Lys Pro Tyr
            100                 105                 110

Val Leu Leu Gly Ala Gly His Tyr Lys Tyr Asp Phe Asp Gly Val Asn
        115                 120                 125

Arg Gly Thr Arg Gly Thr Ser Glu Glu Gly Thr Leu Gly Asn Ala Gly
    130                 135                 140

Val Gly Ala Phe Trp Arg Leu Asn Asp Ala Leu Ser Leu Arg Thr Glu
145                 150                 155                 160

Ala Arg Ala Thr Tyr Asn Ala Asp Glu Glu Phe Trp Asn Tyr Thr Ala
                165                 170                 175

Leu Ala Gly Leu Asn Val Val Leu Gly Gly His Leu Lys Pro Ala Ala
            180                 185                 190

Pro Val Val Glu Val Ala Pro Val Glu Pro Thr Pro Val Thr Pro Gln
        195                 200                 205

Pro Gln Glu Leu Thr Glu Asp Leu Asn Met Glu Leu Arg Val Phe Phe
    210                 215                 220

Asp Thr Asn Lys Ser Asn Ile Lys Asp Gln Tyr Lys Pro Glu Ile Ala
225                 230                 235                 240

Lys Val Ala Glu Lys Leu Ser Glu Tyr Pro Asn Ala Thr Ala Arg Ile
                245                 250                 255

Glu Gly His Thr Asp Asn Thr Gly Pro Arg Lys Leu Asn Glu Arg Leu
            260                 265                 270

Ser Leu Ala Arg Ala Asn Ser Val Lys Ser Ala Leu Val Asn Glu Tyr
        275                 280                 285

Asn Val Asp Ala Ser Arg Leu Ser Thr Gln Gly Phe Ala Trp Asp Gln
    290                 295                 300

Pro Ile Ala Asp Asn Lys Thr Lys Glu Gly Arg Ala Met Asn Arg Arg
305                 310                 315                 320

Val Phe Ala Thr Ile Thr Gly Ser Arg Thr Val Val Gln Pro Gly
                325                 330                 335

Gln Glu Ala Ala Pro Ala Ala Ala Gln
            340                 345

<210> SEQ ID NO 7
<211> LENGTH: 16
<212> TYPE: PRT
```

<213> ORGANISM: Acinetobacter baumannii

<400> SEQUENCE: 7

Pro Arg Lys Leu Asn Glu Arg Leu Ser Leu Ala Arg Ala Asn Ser Val
1               5                   10                  15

<210> SEQ ID NO 8
<211> LENGTH: 13
<212> TYPE: PRT
<213> ORGANISM: Acinetobacter baumannii

<400> SEQUENCE: 8

Ala Asp Asn Lys Thr Lys Glu Gly Arg Ala Met Asn Arg
1               5                   10

<210> SEQ ID NO 9
<211> LENGTH: 13
<212> TYPE: PRT
<213> ORGANISM: Acinetobacter baumannii

<400> SEQUENCE: 9

Arg Arg Val Phe Ala Thr Ile Thr Gly Ser Arg Thr Val
1               5                   10

<210> SEQ ID NO 10
<211> LENGTH: 13
<212> TYPE: PRT
<213> ORGANISM: Acinetobacter baumannii

<400> SEQUENCE: 10

Lys Tyr Asp Phe Asp Gly Val Asn Arg Gly Thr Arg Gly
1               5                   10

<210> SEQ ID NO 11
<211> LENGTH: 368
<212> TYPE: PRT
<213> ORGANISM: Acinetobacter baumannii

<400> SEQUENCE: 11

Met Ala Tyr Cys Gly Leu Glu Leu Glu Gln Gln Phe Leu Ser Leu Glu
1               5                   10                  15

Asp Lys Ser Met Lys Met Ser Arg Ile Ala Leu Ala Met Leu Val Ala
                20                  25                  30

Ala Pro Phe Ala Ala Ala Asn Ala Gly Val Thr Val Thr Pro Leu Met
            35                  40                  45

Leu Gly Tyr Thr Phe Gln Asp Thr Gln His Asn Asn Asn Gly Asn Asp
        50                  55                  60

Gly Glu Leu Thr Ser Ser Pro Glu Leu Gln Asp Asp Leu Phe Val Gly
65                  70                  75                  80

Ala Ala Ile Gly Val Glu Leu Thr Pro Trp Leu Gly Phe Glu Ala Glu
                85                  90                  95

Tyr Ser Gln Val Lys Gly Asp Val Asp Gly Ala Ala Glu Gly Ala Glu
                100                 105                 110

Tyr Lys Gly Gln Asn Ile Ala Gly Asn Phe Tyr Ala Thr Ser Asp Val
            115                 120                 125

Phe Thr Gly Asn Tyr Asp Ser Lys Val Lys Pro Tyr Met Leu Leu Gly
        130                 135                 140

Ala Gly His Tyr Lys Tyr Glu Phe Glu Gly Val Pro Arg Gly Thr Arg
145                 150                 155                 160

Gly Asn Glu Glu Glu Gly Thr Leu Gly Asn Ala Gly Val Gly Ala Phe
                165                 170                 175

-continued

```
Trp His Ile Asn Asp Ala Leu Ala Leu Arg Thr Glu Ala Arg Gly Thr
            180                 185                 190

Tyr His Phe Asp Glu Lys Phe Trp Asn Tyr Thr Ala Leu Ala Gly Leu
        195                 200                 205

Asn Val Val Leu Gly Gly Arg Leu Lys Pro Ala Ala Pro Val Val Glu
    210                 215                 220

Val Ala Pro Val Glu Pro Val Thr Pro Val Ala Pro Pro Gln Glu
225                 230                 235                 240

Leu Thr Glu Asp Leu Asn Met Glu Leu Arg Val Phe Phe Asp Thr Asn
                245                 250                 255

Lys Ser Asn Ile Lys Asp Gln Tyr Lys Pro Glu Ile Ala Lys Val Ala
            260                 265                 270

Glu Lys Leu Val Glu Tyr Pro Asn Ala Thr Ala Arg Ile Glu Gly His
        275                 280                 285

Thr Asp Asn Thr Gly Pro Arg Ala Leu Asn Glu Arg Leu Ser Leu Ala
    290                 295                 300

Arg Ala Asn Ser Val Lys Ser Ser Leu Val Asn Glu Tyr Asn Val Asp
305                 310                 315                 320

Ala Ser Arg Leu Ser Thr Gln Gly Phe Ala Trp Asp Gln Pro Ile Ala
                325                 330                 335

Asp Asn Asn Thr Lys Glu Gly Arg Ala Met Asn Arg Val Phe Ala
            340                 345                 350

Thr Ile Thr Gly Ser Arg Thr Val Leu Ala Glu Gln Pro Val Ala Gln
        355                 360                 365
```

<210> SEQ ID NO 12
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
catcaccatg ggatccttgt tgctgctcca ttagct     36

<210> SEQ ID NO 13
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
ctaattaagc ttggctgcag ttattgagct gctgcagga     39

<210> SEQ ID NO 14
<211> LENGTH: 356
<212> TYPE: PRT
<213> ORGANISM: Acinetobacter baumannii

<400> SEQUENCE: 14

```
Met Lys Leu Ser Arg Ile Ala Leu Ala Thr Met Leu Val Ala Ala Pro
1               5                   10                  15

Leu Ala Ala Ala Asn Ala Gly Val Thr Val Thr Pro Leu Leu Leu Gly
            20                  25                  30

Tyr Thr Phe Gln Asp Ser Gln His Asn Asn Gly Gly Lys Asp Gly Asn
        35                  40                  45
```

```
Leu Thr Asn Gly Pro Glu Leu Gln Asp Asp Leu Phe Val Gly Ala Ala
 50                  55                  60

Leu Gly Ile Glu Leu Thr Pro Trp Leu Gly Phe Glu Ala Glu Tyr Asn
 65                  70                  75                  80

Gln Val Lys Gly Asp Val Asp Gly Ala Ser Ala Gly Ala Glu Tyr Lys
                 85                  90                  95

Gln Lys Gln Ile Asn Gly Asn Phe Tyr Val Thr Ser Asp Leu Ile Thr
            100                 105                 110

Lys Asn Tyr Asp Ser Lys Ile Lys Pro Tyr Val Leu Gly Ala Gly
            115                 120                 125

His Tyr Lys Tyr Asp Phe Asp Gly Val Asn Arg Gly Thr Arg Gly Thr
    130                 135                 140

Ser Glu Glu Gly Thr Leu Gly Asn Ala Gly Val Gly Ala Phe Trp Arg
145                 150                 155                 160

Leu Asn Asp Ala Leu Ser Leu Arg Thr Glu Ala Arg Ala Thr Tyr Asn
                165                 170                 175

Ala Asp Glu Glu Phe Trp Asn Tyr Thr Ala Leu Ala Gly Leu Asn Val
            180                 185                 190

Val Leu Gly Gly His Leu Lys Pro Ala Ala Pro Val Val Glu Val Ala
        195                 200                 205

Pro Val Glu Pro Thr Pro Val Thr Pro Gln Pro Gln Glu Leu Thr Glu
    210                 215                 220

Asp Leu Asn Met Glu Leu Arg Val Phe Phe Asp Thr Asn Lys Ser Asn
225                 230                 235                 240

Ile Lys Asp Gln Tyr Lys Pro Glu Ile Ala Lys Val Ala Glu Lys Leu
                245                 250                 255

Ser Glu Tyr Pro Asn Ala Thr Ala Arg Ile Glu Gly His Thr Asp Asn
            260                 265                 270

Thr Gly Pro Arg Lys Leu Asn Glu Arg Leu Ser Leu Ala Arg Ala Asn
        275                 280                 285

Ser Val Lys Ser Ala Leu Val Asn Glu Tyr Asn Val Asp Ala Ser Arg
    290                 295                 300

Leu Ser Thr Gln Gly Phe Ala Trp Asp Gln Pro Ile Ala Asp Asn Lys
305                 310                 315                 320

Thr Lys Glu Gly Arg Ala Met Asn Arg Arg Val Phe Ala Thr Ile Thr
                325                 330                 335

Gly Ser Arg Thr Val Val Val Gln Pro Gly Gln Glu Ala Ala Ala Pro
            340                 345                 350

Ala Ala Ala Gln
        355

<210> SEQ ID NO 15
<211> LENGTH: 356
<212> TYPE: PRT
<213> ORGANISM: Acinetobacter baumannii

<400> SEQUENCE: 15

Met Lys Leu Ser Arg Ile Ala Leu Ala Thr Met Leu Val Ala Ala Pro
1               5                   10                  15

Leu Ala Ala Ala Asn Ala Gly Val Thr Val Thr Pro Leu Leu Leu Gly
            20                  25                  30

Tyr Thr Phe Gln Asp Ser Gln His Asn Asn Gly Gly Lys Asp Gly Asn
        35                  40                  45

Leu Thr Asn Gly Pro Glu Leu Gln Asp Asp Leu Phe Val Gly Ala Ala
 50                  55                  60
```

```
Leu Gly Ile Glu Leu Thr Pro Trp Leu Gly Phe Ala Glu Tyr Asn
 65                  70                  75                  80

Gln Val Lys Gly Asp Val Asp Gly Ala Ser Ala Gly Ala Glu Tyr Lys
                 85                  90                  95

Gln Lys Gln Ile Asn Gly Asn Phe Tyr Val Thr Ser Asp Leu Ile Thr
                100                 105                 110

Lys Asn Tyr Asp Ser Lys Ile Lys Pro Tyr Val Leu Gly Ala Gly
                115                 120                 125

His Tyr Lys Tyr Asp Phe Asp Gly Val Asn Arg Gly Thr Arg Gly Thr
            130                 135                 140

Ser Glu Glu Gly Thr Leu Gly Asn Ala Gly Val Gly Ala Phe Trp Arg
145                 150                 155                 160

Leu Asn Asp Ala Leu Ser Leu Arg Thr Glu Ala Arg Ala Thr Tyr Asn
                165                 170                 175

Ala Asp Glu Glu Phe Trp Asn Tyr Thr Ala Leu Ala Gly Leu Asn Val
                180                 185                 190

Val Leu Gly Gly His Leu Lys Pro Ala Ala Pro Val Glu Val Ala
            195                 200                 205

Pro Val Glu Pro Thr Pro Val Ala Pro Gln Pro Gln Glu Leu Thr Glu
210                 215                 220

Asp Leu Asn Met Glu Leu Arg Val Phe Phe Asp Thr Asn Lys Ser Asn
225                 230                 235                 240

Ile Lys Asp Gln Tyr Lys Pro Glu Ile Ala Lys Val Ala Glu Lys Leu
                245                 250                 255

Ser Glu Tyr Pro Asn Ala Thr Ala Arg Ile Glu Gly His Thr Asp Asn
                260                 265                 270

Thr Gly Pro Arg Lys Leu Asn Glu Arg Leu Ser Leu Ala Arg Ala Asn
                275                 280                 285

Ser Val Lys Ser Ala Leu Val Asn Glu Tyr Asn Val Asp Ala Ser Arg
                290                 295                 300

Leu Ser Thr Gln Gly Phe Ala Trp Asp Gln Pro Ile Ala Asp Asn Lys
305                 310                 315                 320

Thr Lys Glu Gly Arg Ala Met Asn Arg Arg Val Phe Ala Thr Ile Thr
                325                 330                 335

Gly Ser Arg Thr Val Val Val Gln Pro Gly Gln Glu Ala Ala Ala Pro
                340                 345                 350

Ala Ala Ala Gln
            355

<210> SEQ ID NO 16
<211> LENGTH: 356
<212> TYPE: PRT
<213> ORGANISM: Acinetobacter baumannii

<400> SEQUENCE: 16

Met Lys Leu Ser Arg Ile Ala Leu Ala Thr Met Leu Val Ala Ala Pro
  1               5                  10                  15

Leu Ala Ala Ala Asn Ala Gly Val Thr Val Thr Pro Leu Leu Leu Gly
                 20                  25                  30

Tyr Thr Phe Gln Asp Ser Gln His Asn Asn Gly Gly Lys Asp Gly Asn
                 35                  40                  45

Leu Thr Asn Ser Pro Glu Leu Gln Asp Asp Leu Phe Val Gly Ala Ala
             50                  55                  60

Leu Gly Ile Glu Leu Thr Pro Trp Leu Gly Phe Glu Ala Glu Tyr Asn
 65                  70                  75                  80
```

```
Gln Val Lys Gly Asp Val Asp Gly Ala Ser Ala Gly Ala Glu Tyr Lys
                85                  90                  95

Gln Lys Gln Ile Asn Gly Asn Phe Tyr Val Thr Ser Asp Leu Ile Thr
            100                 105                 110

Lys Asn Tyr Asp Ser Lys Ile Lys Pro Tyr Val Leu Leu Gly Ala Gly
        115                 120                 125

His Tyr Lys Tyr Asp Phe Asp Gly Val Asn Arg Gly Thr Arg Gly Thr
    130                 135                 140

Ser Glu Glu Gly Thr Leu Gly Asn Ala Gly Val Gly Ala Phe Trp Arg
145                 150                 155                 160

Leu Asn Asp Ala Leu Ser Leu Arg Thr Glu Ala Arg Ala Thr Tyr Asn
                165                 170                 175

Ala Asp Glu Glu Phe Trp Asn Tyr Thr Ala Leu Ala Gly Leu Asn Val
            180                 185                 190

Val Leu Gly Gly His Leu Lys Pro Ala Ala Pro Val Glu Val Ala
        195                 200                 205

Pro Val Glu Pro Thr Pro Val Ala Pro Gln Pro Gln Glu Leu Thr Glu
210                 215                 220

Asp Leu Asn Met Glu Leu Arg Val Phe Phe Asp Thr Asn Lys Ser Asn
225                 230                 235                 240

Ile Lys Asp Gln Tyr Lys Pro Glu Ile Ala Lys Val Ala Glu Lys Leu
                245                 250                 255

Ser Glu Tyr Pro Asn Ala Thr Ala Arg Ile Glu Gly His Thr Asp Asn
            260                 265                 270

Thr Gly Pro Arg Lys Leu Asn Glu Arg Leu Ser Leu Ala Arg Ala Asn
        275                 280                 285

Ser Val Lys Ser Ala Leu Val Asn Glu Tyr Asn Val Asp Ala Ser Arg
290                 295                 300

Leu Ser Thr Gln Gly Phe Ala Trp Asp Gln Pro Ile Ala Asp Asn Lys
305                 310                 315                 320

Thr Lys Glu Gly Arg Ala Met Asn Arg Arg Val Phe Ala Thr Ile Thr
                325                 330                 335

Gly Ser Arg Thr Val Val Val Gln Pro Gly Gln Glu Ala Ala Ala Pro
            340                 345                 350

Ala Ala Ala Gln
        355

<210> SEQ ID NO 17
<211> LENGTH: 343
<212> TYPE: PRT
<213> ORGANISM: Acinetobacter baumannii

<400> SEQUENCE: 17

Met Lys Leu Ser Arg Ile Ala Leu Ala Thr Met Leu Val Ala Ala Pro
1               5                   10                  15

Leu Ala Ala Ala Asn Ala Gly Val Thr Val Thr Pro Leu Leu Leu Gly
                20                  25                  30

Tyr Thr Phe Gln Asp Ser Gln His Asn Asn Gly Gly Lys Asp Gly Asn
            35                  40                  45

Leu Thr Asn Ser Pro Glu Leu Gln Asp Asp Leu Phe Val Gly Ala Ala
        50                  55                  60

Leu Gly Ile Glu Leu Thr Pro Trp Leu Gly Phe Glu Ala Glu Tyr Asn
65                  70                  75                  80

Gln Val Lys Gly Asp Val Asp Gly Ala Ser Ala Gly Ala Glu Tyr Lys
                85                  90                  95
```

```
Gln Lys Gln Ile Asn Gly Asn Phe Tyr Val Thr Ser Asp Leu Ile Thr
            100                 105                 110

Lys Asn Tyr Asp Ser Lys Ile Lys Pro Tyr Val Leu Leu Gly Ala Gly
            115                 120                 125

His Tyr Lys Tyr Asp Phe Asp Gly Val Asn Arg Gly Thr Arg Gly Thr
            130                 135                 140

Ser Glu Glu Gly Thr Leu Gly Asn Ala Gly Val Gly Ala Phe Trp Arg
145                 150                 155                 160

Leu Asn Asp Ala Leu Ser Leu Arg Thr Glu Ala Arg Ala Thr Tyr Asn
                165                 170                 175

Ala Asp Glu Glu Phe Trp Asn Tyr Thr Ala Leu Ala Gly Leu Asn Val
            180                 185                 190

Val Leu Gly Gly His Leu Lys Pro Ala Ala Pro Val Val Glu Val Ala
            195                 200                 205

Pro Val Glu Pro Thr Pro Val Ala Pro Gln Pro Gln Glu Leu Thr Glu
            210                 215                 220

Asp Leu Asn Met Glu Leu Arg Val Phe Phe Asp Thr Asn Lys Ser Asn
225                 230                 235                 240

Ile Lys Asp Gln Tyr Lys Pro Glu Ile Ala Lys Val Ala Glu Lys Leu
                245                 250                 255

Ser Glu Tyr Pro Asn Ala Thr Ala Arg Ile Glu Gly His Thr Asp Asn
            260                 265                 270

Thr Gly Pro Arg Lys Leu Asn Glu Arg Leu Ser Leu Ala Arg Ala Asn
            275                 280                 285

Ser Val Lys Ser Ala Leu Val Asn Glu Tyr Asn Val Asp Ala Ser Arg
            290                 295                 300

Leu Ser Thr Gln Gly Phe Ala Trp Asp Gln Pro Ile Ala Asp Asn Lys
305                 310                 315                 320

Thr Lys Glu Gly Arg Ala Met Asn Arg Arg Val Phe Ala Thr Ile Thr
                325                 330                 335

Gly Ser Arg Thr Val Leu Ala
            340

<210> SEQ ID NO 18
<211> LENGTH: 340
<212> TYPE: PRT
<213> ORGANISM: Acinetobacter baumannii

<400> SEQUENCE: 18

Met Lys Leu Ser Arg Ile Ala Leu Ala Thr Met Leu Val Ala Ala Pro
1               5                   10                  15

Leu Ala Ala Ala Asn Ala Gly Val Thr Val Thr Pro Leu Leu Leu Gly
            20                  25                  30

Tyr Thr Phe Gln Asp Ser Gln His Asn Asn Gly Gly Lys Asp Gly Asn
            35                  40                  45

Leu Thr Asn Ser Pro Glu Leu Gln Asp Asp Leu Phe Val Gly Ala Ala
            50                  55                  60

Leu Gly Ile Glu Leu Thr Pro Trp Leu Gly Phe Glu Ala Glu Tyr Asn
65                  70                  75                  80

Gln Val Lys Gly Asp Val Asp Gly Ala Ser Ala Gly Ala Glu Tyr Lys
                85                  90                  95

Gln Lys Gln Ile Asn Gly Asn Phe Tyr Val Thr Ser Asp Leu Ile Thr
            100                 105                 110

Lys Asn Tyr Asp Ser Lys Ile Lys Pro Tyr Val Leu Leu Gly Ala Gly
            115                 120                 125
```

His Tyr Lys Tyr Asp Phe Asp Gly Val Asn Arg Gly Thr Arg Gly Thr
        130                 135                 140

Ser Glu Glu Gly Thr Leu Gly Asn Ala Gly Val Gly Ala Phe Trp Arg
145                 150                 155                 160

Leu Asn Asp Ala Leu Ser Leu Arg Thr Glu Ala Arg Ala Thr Tyr Asn
                165                 170                 175

Ala Asp Glu Glu Phe Trp Asn Tyr Thr Ala Leu Ala Gly Leu Asn Val
            180                 185                 190

Val Leu Gly Gly His Leu Lys Pro Ala Ala Pro Val Glu Val Ala
        195                 200                 205

Pro Val Glu Pro Thr Pro Val Ala Pro Gln Pro Gln Glu Leu Thr Glu
210                 215                 220

Asp Leu Asn Met Glu Leu Arg Val Phe Phe Asp Thr Asn Lys Ser Asn
225                 230                 235                 240

Ile Lys Asp Gln Tyr Lys Pro Glu Ile Ala Lys Val Ala Glu Lys Leu
                245                 250                 255

Ser Glu Tyr Pro Asn Ala Thr Ala Arg Ile Glu Gly His Thr Asp Asn
            260                 265                 270

Thr Gly Pro Arg Lys Leu Asn Glu Arg Leu Ser Leu Ala Arg Ala Asn
        275                 280                 285

Ser Val Lys Ser Ala Leu Val Asn Glu Tyr Asn Val Asp Ala Ser Arg
290                 295                 300

Leu Ser Thr Gln Gly Phe Ala Trp Asp Gln Pro Ile Ala Asp Asn Lys
305                 310                 315                 320

Thr Lys Glu Gly Arg Ala Met Asn Arg Arg Val Phe Ala Thr Ile Thr
                325                 330                 335

Gly Ser Arg Thr
            340

<210> SEQ ID NO 19
<211> LENGTH: 337
<212> TYPE: PRT
<213> ORGANISM: Acinetobacter baumannii

<400> SEQUENCE: 19

Met Lys Leu Ser Arg Ile Ala Leu Ala Thr Met Leu Val Ala Ala Pro
1               5                   10                  15

Leu Ala Ala Ala Asn Ala Gly Val Thr Val Thr Pro Leu Leu Leu Gly
                20                  25                  30

Tyr Thr Phe Gln Asp Ser Gln His Asn Asn Gly Gly Lys Asp Gly Asn
            35                  40                  45

Leu Thr Asn Ser Pro Glu Leu Gln Asp Asp Leu Phe Val Gly Ala Ala
50                  55                  60

Leu Gly Ile Glu Leu Thr Pro Trp Leu Gly Phe Glu Ala Glu Tyr Asn
65                  70                  75                  80

Gln Val Lys Gly Asp Val Asp Gly Ala Ser Ala Gly Ala Glu Tyr Lys
                85                  90                  95

Gln Lys Gln Ile Asn Gly Asn Phe Tyr Val Thr Ser Asp Leu Ile Thr
            100                 105                 110

Lys Asn Tyr Asp Ser Lys Ile Lys Pro Tyr Val Leu Leu Gly Ala Gly
        115                 120                 125

His Tyr Lys Tyr Asp Phe Asp Gly Val Asn Arg Gly Thr Arg Gly Thr
        130                 135                 140

Ser Glu Glu Gly Thr Leu Gly Asn Ala Gly Val Gly Ala Phe Trp Arg
145                 150                 155                 160

```
Leu Asn Asp Ala Leu Ser Leu Arg Thr Glu Ala Arg Ala Thr Tyr Asn
            165                 170                 175

Ala Asp Glu Glu Phe Trp Asn Tyr Thr Ala Leu Ala Gly Leu Asn Val
        180                 185                 190

Val Leu Gly Gly His Leu Lys Pro Ala Ala Pro Val Val Glu Val Ala
    195                 200                 205

Pro Val Glu Pro Thr Pro Val Ala Pro Gln Pro Gln Glu Leu Thr Glu
210                 215                 220

Asp Leu Asn Met Glu Leu Arg Val Phe Phe Asp Thr Asn Lys Ser Asn
225                 230                 235                 240

Ile Lys Asp Gln Tyr Lys Pro Glu Ile Ala Lys Val Ala Glu Lys Leu
            245                 250                 255

Ser Glu Tyr Pro Asn Ala Thr Ala Arg Ile Glu Gly His Thr Asp Asn
        260                 265                 270

Thr Gly Pro Arg Lys Leu Asn Glu Arg Leu Ser Leu Ala Arg Ala Asn
    275                 280                 285

Ser Val Lys Ser Ala Leu Val Asn Glu Tyr Asn Val Asp Ala Ser Arg
290                 295                 300

Leu Ser Thr Gln Gly Phe Ala Trp Asp Gln Pro Ile Ala Asp Asn Lys
305                 310                 315                 320

Thr Lys Glu Gly Arg Ala Met Asn Arg Arg Val Phe Pro Thr Ile Thr
            325                 330                 335

Gly

<210> SEQ ID NO 20
<211> LENGTH: 334
<212> TYPE: PRT
<213> ORGANISM: Acinetobacter baumannii

<400> SEQUENCE: 20

Met Lys Leu Ser Arg Ile Ala Leu Ala Thr Met Leu Val Ala Ala Pro
1               5                   10                  15

Leu Ala Ala Ala Asn Ala Gly Val Thr Val Thr Pro Leu Leu Leu Gly
            20                  25                  30

Tyr Thr Phe Gln Asp Ser Gln His Asn Asn Gly Gly Lys Asp Gly Asn
        35                  40                  45

Leu Thr Asn Gly Pro Glu Leu Gln Asp Asp Leu Phe Val Gly Ala Ala
    50                  55                  60

Leu Gly Ile Glu Leu Thr Pro Trp Leu Gly Phe Glu Ala Glu Tyr Asn
65                  70                  75                  80

Gln Val Lys Gly Asp Val Asp Gly Pro Val Ala Gly Ala Glu Tyr Lys
            85                  90                  95

Gln Lys Gln Ile Asn Gly Asn Phe Tyr Val Thr Ser Asp Leu Ile Thr
        100                 105                 110

Lys Asn Tyr Asp Ser Lys Ile Lys Pro Tyr Val Leu Leu Gly Ala Gly
    115                 120                 125

His Tyr Lys Tyr Asp Phe Asp Gly Val Asn Arg Gly Thr Arg Gly Asn
130                 135                 140

Ser Glu Glu Gly Thr Leu Gly Asn Ala Gly Val Gly Ala Phe Trp Arg
145                 150                 155                 160

Leu Asn Asp Ala Leu Ser Leu Arg Thr Glu Ala Arg Ala Thr Tyr Asn
            165                 170                 175

Ala Asp Glu Glu Phe Trp Asn Tyr Thr Ala Leu Ala Gly Leu Asn Val
        180                 185                 190

Val Leu Gly Gly His Leu Lys Pro Ala Ala Pro Val Val Glu Val Ala
```

```
                195                 200                 205
Pro Val Glu Pro Thr Pro Val Ala Pro Gln Pro Gln Glu Leu Thr Glu
    210                 215                 220

Asp Leu Asn Met Glu Leu Arg Val Phe Phe Asp Thr Asn Lys Ser Asn
225                 230                 235                 240

Ile Lys Asp Gln Tyr Lys Pro Glu Ile Ala Lys Val Ala Glu Lys Leu
            245                 250                 255

Ser Glu Tyr Pro Asn Ala Thr Ala Arg Ile Glu Gly His Thr Asp Asn
                260                 265                 270

Thr Gly Pro Arg Lys Leu Asn Glu Arg Leu Ser Leu Ala Arg Ala Asn
            275                 280                 285

Ser Val Lys Ser Ala Leu Val Asn Glu Tyr Asn Val Asp Ala Ser Arg
        290                 295                 300

Leu Ser Thr Gln Gly Phe Ala Trp Asp Gln Pro Ile Ala Asp Asn Lys
305                 310                 315                 320

Thr Lys Glu Gly Arg Ala Met Asn Arg Arg Val Phe Ala Thr
                325                 330

<210> SEQ ID NO 21
<211> LENGTH: 357
<212> TYPE: PRT
<213> ORGANISM: Acinetobacter baumannii

<400> SEQUENCE: 21

Met Lys Leu Ser Arg Ile Ala Leu Ala Thr Met Leu Val Ala Ala Pro
1               5                   10                  15

Leu Ala Ala Ala Asn Ala Gly Val Thr Val Thr Pro Leu Leu Leu Gly
            20                  25                  30

Tyr Thr Phe Gln Asp Ser Gln His Asn Asn Gly Gly Lys Asp Gly Asn
        35                  40                  45

Leu Thr Asn Ser Pro Glu Leu Gln Asp Asp Leu Phe Val Gly Ala Ala
50                  55                  60

Leu Gly Ile Glu Leu Thr Pro Trp Leu Gly Phe Glu Ala Glu Tyr Asn
65                  70                  75                  80

Gln Val Lys Gly Asp Val Asp Gly Ala Ser Ala Gly Ala Glu Tyr Lys
                85                  90                  95

Gln Lys Gln Ile Asn Gly Asn Phe Tyr Val Thr Ser Asp Leu Ile Thr
            100                 105                 110

Lys Asn Tyr Asp Ser Lys Ile Lys Pro Tyr Val Leu Leu Gly Ala Gly
        115                 120                 125

His Tyr Lys Tyr Asp Phe Asp Gly Val Asn Arg Gly Thr Arg Gly Asn
    130                 135                 140

Ser Glu Glu Gly Thr Leu Gly Asn Ala Gly Val Gly Ala Phe Trp Arg
145                 150                 155                 160

Leu Asn Asp Ala Leu Ser Leu Arg Thr Glu Ala Arg Ala Thr Tyr Asn
                165                 170                 175

Ala Asp Glu Glu Phe Trp Asn Tyr Thr Ala Leu Ala Gly Leu Asn Val
            180                 185                 190

Val Leu Gly Gly His Leu Lys Pro Ala Ala Pro Val Val Val Glu Val
        195                 200                 205

Ala Pro Val Glu Pro Thr Pro Val Ala Pro Gln Pro Gln Glu Leu Thr
    210                 215                 220

Glu Asp Leu Asn Met Glu Leu Arg Val Phe Phe Asp Thr Asn Lys Ser
225                 230                 235                 240

Asn Ile Lys Asp Gln Tyr Lys Pro Glu Ile Ala Lys Val Ala Glu Lys
```

```
                        245                 250                 255
Leu Ser Glu Tyr Pro Asn Ala Thr Ala Arg Ile Glu Gly His Thr Asp
                260                 265                 270

Asn Thr Gly Pro Arg Lys Leu Asn Glu Arg Leu Ser Leu Ala Arg Ala
            275                 280                 285

Asn Ser Val Lys Ser Ala Leu Val Asn Glu Tyr Asn Val Asp Ala Ser
        290                 295                 300

Arg Leu Ser Thr Gln Gly Phe Ala Trp Asp Gln Pro Ile Ala Asp Asn
305                 310                 315                 320

Lys Thr Lys Glu Gly Arg Ala Met Asn Arg Arg Val Phe Ala Thr Ile
                325                 330                 335

Thr Gly Ser Arg Thr Val Val Val Gln Pro Gly Gln Glu Ala Ala Ala
            340                 345                 350

Pro Ala Ala Ala Gln
            355

<210> SEQ ID NO 22
<211> LENGTH: 352
<212> TYPE: PRT
<213> ORGANISM: Acinetobacter baumannii

<400> SEQUENCE: 22

Met Lys Leu Ser Arg Ile Ala Leu Ala Thr Met Leu Val Ala Ala Pro
1               5                   10                  15

Leu Ala Ala Ala Asn Ala Gly Val Thr Val Thr Pro Leu Leu Leu Gly
            20                  25                  30

Tyr Thr Phe Gln Asp Thr Gln His Asn Asn Gly Gly Lys Asp Gly Glu
        35                  40                  45

Leu Thr Asn Gly Pro Glu Leu Gln Asp Asp Leu Phe Val Gly Ala Ala
    50                  55                  60

Leu Gly Ile Glu Leu Thr Pro Trp Leu Gly Phe Glu Ala Glu Tyr Asn
65                  70                  75                  80

Gln Val Lys Gly Asp Val Asp Gly Leu Ala Ala Gly Ala Glu Tyr Lys
                85                  90                  95

Gln Lys Gln Ile Asn Gly Asn Phe Tyr Val Thr Ser Asp Leu Ile Thr
            100                 105                 110

Lys Asn Tyr Asp Ser Lys Ile Lys Pro Tyr Val Leu Leu Gly Ala Gly
        115                 120                 125

His Tyr Lys Tyr Glu Ile Pro Asp Leu Ser Tyr His Asn Asp Glu Glu
    130                 135                 140

Gly Thr Leu Gly Asn Ala Gly Val Gly Ala Phe Trp Arg Leu Asn Asp
145                 150                 155                 160

Ala Leu Ser Leu Arg Thr Glu Ala Arg Gly Thr Tyr Asn Phe Asp Glu
                165                 170                 175

Lys Phe Trp Asn Tyr Thr Ala Leu Ala Gly Leu Asn Val Val Leu Gly
            180                 185                 190

Gly His Leu Lys Pro Ala Ala Pro Val Val Glu Val Ala Pro Val Glu
        195                 200                 205

Pro Thr Pro Val Ala Pro Gln Pro Gln Glu Leu Thr Glu Asp Leu Asn
    210                 215                 220

Met Glu Leu Arg Val Phe Phe Asp Thr Asn Lys Ser Asn Ile Lys Asp
225                 230                 235                 240

Gln Tyr Lys Pro Glu Ile Ala Lys Val Ala Glu Lys Leu Ser Glu Tyr
                245                 250                 255

Pro Asn Ala Thr Ala Arg Ile Glu Gly His Thr Asp Asn Thr Gly Pro
```

```
              260                 265                 270
Arg Lys Leu Asn Glu Arg Leu Ser Leu Ala Arg Ala Asn Ser Val Lys
        275                 280                 285

Ser Ala Leu Val Asn Glu Tyr Asn Val Asp Ala Ser Arg Leu Ser Thr
        290                 295                 300

Gln Gly Phe Ala Trp Asp Gln Pro Ile Ala Asp Asn Lys Thr Lys Glu
305                 310                 315                 320

Gly Arg Ala Met Asn Arg Arg Val Phe Ala Thr Ile Thr Gly Ser Arg
                325                 330                 335

Thr Val Val Gln Gly Gln Glu Ala Ala Pro Ala Ala Ala Gln
            340                 345                 350

<210> SEQ ID NO 23
<211> LENGTH: 352
<212> TYPE: PRT
<213> ORGANISM: Acinetobacter baumannii

<400> SEQUENCE: 23

Met Lys Leu Ser Arg Ile Ala Leu Ala Thr Met Leu Val Ala Ala Pro
1               5                   10                  15

Leu Ala Ala Ala Asn Ala Gly Val Thr Val Thr Pro Leu Leu Leu Gly
            20                  25                  30

Tyr Thr Phe Gln Asp Thr Gln His Asn Asn Gly Gly Lys Asp Gly Glu
        35                  40                  45

Leu Thr Asn Gly Pro Glu Leu Gln Asp Asp Leu Phe Val Gly Ala Ala
    50                  55                  60

Leu Gly Ile Glu Leu Thr Pro Trp Leu Gly Phe Glu Ala Glu Tyr Asn
65                  70                  75                  80

Gln Val Lys Gly Asp Val Asp Gly Leu Ala Ala Gly Ala Glu Tyr Lys
                85                  90                  95

Gln Lys Gln Ile Asn Gly Asn Phe Tyr Val Thr Ser Asp Leu Ile Thr
            100                 105                 110

Lys Asn Tyr Asp Ser Lys Ile Lys Pro Tyr Val Leu Leu Gly Ala Gly
        115                 120                 125

His Tyr Lys Tyr Glu Ile Pro Asp Leu Ser Tyr His Asn Asp Glu Glu
    130                 135                 140

Gly Thr Leu Gly Asn Ala Gly Val Gly Ala Phe Trp Arg Leu Asn Asp
145                 150                 155                 160

Ala Leu Ser Leu Arg Thr Glu Ala Arg Gly Thr Tyr Asn Phe Asp Glu
                165                 170                 175

Lys Phe Trp Asn Tyr Thr Ala Leu Ala Gly Leu Asn Val Val Leu Gly
            180                 185                 190

Gly His Leu Lys Pro Ala Ala Pro Val Val Glu Val Ala Pro Val Glu
        195                 200                 205

Pro Thr Pro Val Ala Pro Gln Pro Gln Glu Leu Thr Glu Asp Leu Asn
    210                 215                 220

Met Glu Leu Arg Val Phe Phe Asp Thr Asn Lys Ser Asn Ile Lys Asp
225                 230                 235                 240

Gln Tyr Lys Pro Glu Ile Ala Lys Val Ala Glu Lys Leu Ser Glu Tyr
                245                 250                 255

Pro Asn Ala Thr Ala Arg Ile Glu Gly His Thr Asp Asn Thr Gly Pro
            260                 265                 270

Arg Lys Leu Asn Glu Arg Leu Ser Leu Ala Arg Ala Asn Ser Val Lys
        275                 280                 285

Ser Ala Leu Val Asn Glu Tyr Asn Val Asp Ala Ser Arg Leu Ser Thr
```

```
            290                 295                 300
Gln Gly Phe Ala Trp Asp Gln Pro Ile Ala Asp Asn Lys Thr Lys Glu
305                 310                 315                 320

Gly Arg Ala Met Asn Arg Arg Val Phe Ala Thr Ile Thr Gly Ser Arg
                325                 330                 335

Thr Val Val Gln Gly Gln Glu Ala Ala Pro Ala Ala Ala Gln
                340                 345                 350

<210> SEQ ID NO 24
<211> LENGTH: 341
<212> TYPE: PRT
<213> ORGANISM: Acinetobacter baumannii

<400> SEQUENCE: 24

Met Lys Leu Gly Arg Ile Ala Leu Ala Thr Met Leu Val Ala Ala Pro
1               5                   10                  15

Leu Ala Ala Ala Asn Ala Gly Val Thr Val Thr Pro Leu Leu Leu Gly
                20                  25                  30

Tyr Thr Phe Gln Asp Thr Gln His Asn Asn Gly Gly Lys Asp Gly Glu
            35                  40                  45

Leu Thr Asn Gly Pro Glu Leu Gln Asp Asp Leu Phe Val Gly Ala Ala
        50                  55                  60

Leu Gly Ile Glu Leu Thr Pro Trp Leu Gly Phe Glu Ala Glu Tyr Asn
65                  70                  75                  80

Gln Val Lys Gly Asp Val Asp Gly Leu Ala Ala Gly Ala Glu Tyr Lys
                85                  90                  95

Gln Lys Gln Ile Asn Gly Asn Phe Tyr Val Thr Ser Asp Leu Ile Thr
            100                 105                 110

Lys Asn Tyr Asp Ser Lys Ile Lys Pro Tyr Val Leu Leu Gly Ala Gly
            115                 120                 125

His Tyr Lys Tyr Glu Ile Pro Asp Leu Ser Tyr His Asn Asp Glu Glu
        130                 135                 140

Gly Thr Leu Gly Asn Ala Gly Val Gly Ala Phe Trp Arg Leu Asn Asp
145                 150                 155                 160

Ala Leu Ser Leu Arg Thr Glu Ala Arg Gly Thr Tyr Asn Phe Asp Glu
                165                 170                 175

Lys Phe Trp Asn Tyr Thr Ala Leu Ala Gly Leu Asn Val Val Leu Gly
            180                 185                 190

Gly His Leu Lys Pro Ala Ala Pro Val Val Glu Val Ala Pro Val Glu
        195                 200                 205

Pro Thr Pro Val Ala Pro Gln Pro Gln Glu Leu Thr Glu Asp Leu Asn
210                 215                 220

Met Glu Leu Arg Val Phe Phe Asp Thr Asn Lys Ser Asn Ile Lys Asp
225                 230                 235                 240

Gln Tyr Lys Pro Glu Ile Ala Lys Val Ala Glu Lys Leu Ser Glu Tyr
                245                 250                 255

Pro Asn Ala Thr Ala Arg Ile Glu Gly His Thr Asp Asn Thr Gly Pro
            260                 265                 270

Arg Lys Leu Asn Glu Arg Leu Ser Leu Ala Arg Ala Asn Ser Val Lys
        275                 280                 285

Ser Ala Leu Val Asn Glu Tyr Asn Val Asp Ala Ser Arg Leu Ser Thr
        290                 295                 300

Gln Gly Phe Ala Trp Asp Gln Pro Ile Ala Asp Asn Lys Thr Lys Glu
305                 310                 315                 320

Gly Arg Ala Met Asn Arg Arg Val Phe Ala Thr Ile Thr Gly Ser Arg
```

Thr Val Leu Ala Glu
            340

<210> SEQ ID NO 25
<211> LENGTH: 337
<212> TYPE: PRT
<213> ORGANISM: Acinetobacter baumannii

<400> SEQUENCE: 25

Met Lys Leu Ser Arg Ile Ala Leu Ala Thr Met Leu Val Ala Ala Pro
1               5                   10                  15

Leu Ala Ala Ala Asn Ala Gly Val Thr Val Thr Pro Leu Leu Leu Gly
                20                  25                  30

Tyr Thr Phe Gln Asp Thr Gln His Asn Asn Gly Gly Lys Asp Gly Glu
            35                  40                  45

Leu Thr Asn Gly Pro Glu Leu Gln Asp Asp Leu Phe Val Gly Ala Ala
        50                  55                  60

Leu Gly Ile Glu Leu Thr Pro Trp Leu Gly Phe Glu Ala Glu Tyr Asn
65                  70                  75                  80

Gln Val Lys Gly Asp Val Asp Gly Leu Ala Gly Ala Glu Tyr Lys
                85                  90                  95

Gln Lys Gln Ile Asn Gly Asn Phe Tyr Val Thr Ser Asp Leu Ile Thr
            100                 105                 110

Lys Asn Tyr Asp Ser Lys Ile Lys Pro Tyr Val Leu Leu Gly Ala Gly
        115                 120                 125

His Tyr Lys Tyr Glu Ile Pro Asp Leu Ser Tyr His Asn Asp Glu Glu
130                 135                 140

Gly Thr Leu Gly Asn Ala Gly Val Gly Ala Phe Trp Arg Leu Asn Asp
145                 150                 155                 160

Ala Leu Ser Leu Arg Thr Glu Ala Arg Gly Thr Tyr Asn Phe Asp Glu
                165                 170                 175

Lys Phe Trp Asn Tyr Thr Ala Leu Ala Gly Leu Asn Val Val Leu Gly
            180                 185                 190

Gly His Leu Lys Pro Ala Ala Pro Val Val Glu Val Ala Pro Val Glu
        195                 200                 205

Pro Thr Pro Val Ala Pro Gln Pro Gln Glu Leu Thr Glu Asp Leu Asn
    210                 215                 220

Met Glu Leu Arg Val Phe Phe Asp Thr Asn Lys Ser Asn Ile Lys Asp
225                 230                 235                 240

Gln Tyr Lys Pro Glu Ile Ala Lys Val Ala Glu Lys Leu Ser Glu Tyr
                245                 250                 255

Pro Asn Ala Thr Ala Arg Ile Glu Gly His Thr Asp Asn Thr Gly Pro
            260                 265                 270

Arg Lys Leu Asn Glu Arg Leu Ser Leu Ala Arg Ala Asn Ser Val Lys
        275                 280                 285

Ser Ala Leu Val Asn Glu Tyr Asn Val Asp Ala Ser Arg Leu Ser Thr
    290                 295                 300

Gln Gly Phe Ala Trp Asp Gln Pro Ile Ala Asp Asn Lys Thr Lys Glu
305                 310                 315                 320

Gly Arg Ala Met Asn Arg Arg Val Phe Ala Thr Ile Thr Gly Ser Arg
                325                 330                 335

Thr

<210> SEQ ID NO 26

<211> LENGTH: 346
<212> TYPE: PRT
<213> ORGANISM: Acinetobacter baumannii

<400> SEQUENCE: 26

```
Met Lys Leu Ser Arg Ile Ala Leu Ala Thr Met Leu Val Ala Ala Pro
1               5                   10                  15
Leu Ala Ala Ala Asn Ala Gly Val Thr Val Thr Pro Leu Leu Leu Gly
                20                  25                  30
Tyr Thr Phe Gln Asp Thr Gln His Asn Asn Gly Gly Lys Asp Gly Glu
            35                  40                  45
Leu Thr Asn Gly Pro Glu Leu Gln Asp Asp Leu Phe Val Gly Ala Ala
        50                  55                  60
Leu Gly Ile Glu Leu Thr Pro Trp Leu Gly Phe Glu Ala Glu Tyr Asn
65                  70                  75                  80
Gln Val Lys Gly Asp Val Asp Gly Leu Ala Ala Gly Ala Glu Tyr Lys
                85                  90                  95
Gln Lys Gln Ile Asn Gly Asn Phe Tyr Val Thr Ser Asp Leu Ile Thr
            100                 105                 110
Lys Asn Tyr Asp Ser Lys Ile Lys Pro Tyr Val Leu Leu Gly Ala Gly
        115                 120                 125
His Tyr Lys Tyr Glu Ile Pro Asp Leu Ser Tyr His Asn Asp Glu Glu
130                 135                 140
Gly Thr Leu Gly Asn Ala Gly Val Gly Ala Phe Trp Arg Leu Asn Asp
145                 150                 155                 160
Ala Leu Ser Leu Arg Thr Glu Ala Arg Gly Asn Leu Tyr Phe Asp Glu
                165                 170                 175
Lys Phe Trp Asn Tyr Thr Ala Leu Ala Gly Leu Asn Val Val Leu Gly
            180                 185                 190
Gly His Leu Lys Pro Ala Ala Pro Val Val Glu Val Ala Pro Val Glu
        195                 200                 205
Pro Thr Pro Val Ala Pro Gln Pro Gln Glu Leu Thr Glu Asp Leu Asn
        210                 215                 220
Met Glu Leu Arg Val Phe Phe Asp Thr Asn Lys Ser Asn Ile Lys Asp
225                 230                 235                 240
Gln Tyr Lys Pro Glu Ile Ala Lys Val Ala Glu Lys Leu Ser Glu Tyr
                245                 250                 255
Pro Asn Ala Thr Ala Arg Ile Glu Gly His Thr Asp Asn Thr Gly Pro
            260                 265                 270
Arg Lys Leu Asn Glu Arg Leu Ser Leu Ala Arg Ala Asn Ser Val Lys
        275                 280                 285
Ser Ala Leu Val Asn Glu Tyr Asn Val Asp Ala Ser Arg Leu Ser Thr
        290                 295                 300
Gln Gly Phe Ala Trp Asp Gln Pro Ile Ala Asp Asn Lys Thr Lys Glu
305                 310                 315                 320
Gly Arg Ala Met Asn Arg Arg Val Phe Ala Thr Ile Thr Gly Ser Arg
                325                 330                 335
Thr Val Leu Ala Glu Gln Pro Val Ala Gln
            340                 345
```

<210> SEQ ID NO 27
<211> LENGTH: 333
<212> TYPE: PRT
<213> ORGANISM: Acinetobacter baumannii

<400> SEQUENCE: 27

Met Lys Leu Ser Arg Ile Ala Leu Ala Thr Met Leu Val Ala Ala Pro
1               5                   10                  15

Leu Ala Ala Ala Asn Ala Gly Val Thr Val Thr Pro Leu Leu Leu Gly
                20                  25                  30

Tyr Thr Phe Gln Asp Thr Gln His Asn Asn Gly Gly Lys Asp Gly Glu
            35                  40                  45

Leu Thr Asn Gly Pro Glu Leu Gln Asp Asp Leu Phe Val Gly Ala Ala
        50                  55                  60

Leu Gly Ile Glu Leu Thr Pro Trp Leu Gly Phe Glu Ala Glu Tyr Asn
65                  70                  75                  80

Gln Val Lys Gly Asp Val Asp Gly Leu Ala Ala Gly Ala Glu Tyr Lys
                85                  90                  95

Gln Lys Gln Ile Asn Gly Asn Phe Tyr Val Thr Ser Asp Leu Ile Thr
            100                 105                 110

Lys Asn Tyr Asp Ser Lys Ile Lys Pro Tyr Val Leu Leu Gly Ala Gly
        115                 120                 125

His Tyr Lys Tyr Glu Ile Pro Asp Leu Ser Tyr His Asn Asp Glu Glu
            130                 135                 140

Gly Thr Leu Gly Asn Ala Gly Val Gly Ala Phe Trp Arg Leu Asn Asp
145                 150                 155                 160

Ala Leu Ser Leu Arg Thr Glu Ala Arg Gly Thr Tyr Asn Phe Asp Glu
                165                 170                 175

Lys Phe Trp Asn Tyr Thr Ala Leu Ala Gly Leu Asn Val Val Leu Gly
            180                 185                 190

Gly His Leu Lys Pro Ala Ala Pro Val Glu Val Ala Pro Val Glu
        195                 200                 205

Pro Thr Pro Val Ala Pro Gln Pro Gln Glu Leu Thr Glu Asp Leu Asn
210                 215                 220

Met Glu Leu Arg Val Phe Phe Asp Thr Asn Lys Ser Asn Ile Lys Asp
225                 230                 235                 240

Gln Tyr Lys Pro Glu Ile Ala Lys Val Ala Glu Lys Leu Ser Glu Tyr
                245                 250                 255

Pro Asn Ala Thr Ala Arg Ile Glu Gly His Thr Asp Asn Thr Gly Pro
            260                 265                 270

Arg Lys Leu Asn Glu Arg Leu Ser Leu Ala Arg Ala Asn Ser Val Lys
        275                 280                 285

Ser Ala Leu Val Asn Glu Tyr Asn Val Asp Ala Ser Arg Leu Ser Thr
            290                 295                 300

Gln Gly Phe Ala Trp Asp Gln Pro Ile Ala Asp Asn Lys Thr Lys Glu
305                 310                 315                 320

Gly Arg Ala Met Asn Arg Val Phe Ala Thr Ile Thr
                325                 330

<210> SEQ ID NO 28
<211> LENGTH: 349
<212> TYPE: PRT
<213> ORGANISM: Acinetobacter baumannii

<400> SEQUENCE: 28

Met Lys Leu Ser Arg Ile Ala Leu Ala Thr Met Leu Val Ala Ala Pro
1               5                   10                  15

Leu Ala Ala Ala Asn Ala Gly Val Thr Val Thr Pro Leu Leu Leu Gly
                20                  25                  30

Tyr Thr Phe Gln Asp Ser Glu His Asn Asn His Lys Leu Thr Asp Ser
            35                  40                  45

```
Pro Glu Leu Gln Asp Asp Leu Phe Val Gly Ala Ala Leu Gly Ile Glu
     50                  55                  60

Leu Thr Pro Trp Leu Gly Phe Glu Ala Glu Tyr Asn Gln Val Lys Gly
 65                  70                  75                  80

Asp Val Asp Thr Asn Tyr Gly Tyr Lys Gln Lys Gln Ile Asn Gly
                 85                  90                  95

Asn Phe Tyr Val Thr Ser Asp Leu Ile Thr Lys Asn Tyr Asp Ser Lys
                100                 105                 110

Ile Lys Pro Tyr Val Leu Leu Gly Ala Gly His Tyr Lys Tyr Asp Phe
                115                 120                 125

Asp Asp Ala Arg Leu Ala Tyr His Asp Gly Glu Gly Thr Leu Gly
            130                 135                 140

Asn Ala Gly Val Gly Ala Phe Trp Arg Leu Asn Asp Ala Leu Ser Leu
145                 150                 155                 160

Arg Thr Glu Ala Arg Gly Thr Tyr Asn Phe Asp Glu Lys Phe Trp Asn
                165                 170                 175

Tyr Thr Ala Leu Ala Gly Leu Asn Val Val Leu Gly Gly His Leu Lys
                180                 185                 190

Pro Ala Ala Pro Val Val Glu Val Ala Pro Val Glu Pro Thr Pro Val
                195                 200                 205

Ala Pro Gln Pro Gln Glu Leu Thr Glu Asp Leu Asn Met Glu Leu Arg
            210                 215                 220

Val Phe Phe Asp Thr Asn Lys Ser Asn Ile Lys Asp Gln Tyr Lys Pro
225                 230                 235                 240

Glu Ile Ala Lys Val Ala Glu Lys Leu Ser Glu Tyr Pro Asn Ala Thr
                245                 250                 255

Ala Arg Ile Glu Gly His Thr Asp Asn Thr Gly Pro Arg Lys Leu Asn
                260                 265                 270

Glu Arg Leu Ser Leu Ala Arg Ala Asn Ser Val Lys Ser Ala Leu Val
            275                 280                 285

Asn Glu Tyr Asn Val Asp Ala Ser Arg Leu Ser Thr Gln Gly Phe Ala
            290                 295                 300

Trp Asp Gln Pro Ile Ala Asp Asn Lys Thr Lys Glu Gly Arg Ala Met
305                 310                 315                 320

Asn Arg Arg Val Phe Ala Thr Ile Thr Gly Ser Arg Thr Val Val Val
                325                 330                 335

Gln Pro Gly Gln Glu Ala Ala Pro Ala Ala Gln
            340                 345

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Synthetic
      6x His tag

<400> SEQUENCE: 29

His His His His His His
1               5
```

COMPOSITIONS AND METHODS FOR IMMUNIZATION AGAINST DRUG RESISTANT *ACINETOBACTER BAUMANNII*

This application claims the benefit of priority of U.S. Provisional application Ser. No. 61/486,177 filed May 13, 2011, the entire contents of which are incorporated herein by reference.

This invention was made with government support under grant number PHS R01 AI081719, AI077681, and AI072052 awarded by NIH/NIAID. The government has certain rights in the invention.

Incorporated herein by reference is the Sequence Listing being submitted via EFS-Web as an ASCII text file named 12959-048-999SequenceListing.TXT, created Jul. 10, 2012, and being 68,413 bytes in size.

BACKGROUND OF THE INVENTION

Antibiotic resistance is recognized as one of the greatest threats to human health on the planet (2009; Choffnes et al., *Antibiotic Resistance: Implications for Global Health and Novel Intervention Strategies*, The National Academic Press, Washington, D.C., (2010); Smolinski et al., *Microbial Threats to Health: Emergence, Detection, and Response*, The Institute of Medicine, Washington D.C., (2003); Spellberg et al., *Clin Infect Dis* 52(55):397-428 (2011); Spellberg et al., *Clin Infect Dis* 46:155-164 (2008); Walker et al., *Science* 325-1345-1346 (2009). In the last decade, *Acinetobacter baumannii* has emerged as one of the most common and highly antibiotic-resistant pathogens in the United States (US) and throughout the world (Doi et al., *Emerg Infect Dis* 15:980-982 (2009); Higgins et al., *J Antimicrob Chemother* 65-233-238 (2010); Perez et al., *Antimicrob Agents Chemother* 51:3471-3484 (2007). Indeed, 50-70% of *A. baumannii* clinical isolates are now extensively drug resistant (XDR; i.e. resistant to carbapenems and all other antibiotics except colistin or tigecycline), reflecting a >15-fold increase in just the past 10 years (Dizbay et al., *Scand J Infect Dis* (2010); Hidron et al., *Infect Control Hosp Epidemiol* 29:996-1011 (2008); Hoffmann et al., *Infect Control Hosp Epidemiol* 31:196-197 (2010); Kallen et al., *Infect Control Hosp Epidemiol* 31:528-531 (2010); Lautenbach et al., *Infect Control Hosp Epidemiol* 30:1186-1192 (2009); Mera et al., *Drug Resist* 16:209-215 (2010); Perez et al., *Am J Infect Control* 38:63-65 (2010); Rosenthal et al., *Am J Infect Control* 38:95-104 e102 (2010). Infections caused by carbapenem-resistant, XDR *A. baumannii* are associated with prolonged hospitalization, tremendous health care costs, and high rates of death despite treatment (Doi et al., *Emerg Infect Dis* 15:980-982 (2009); Falagas et al., *Int J Antimicrob Agents* 32:450-454 (2008); Gordon and Wareham, *J Antimicrob Chemother* 63:775-780 (2009); Lautenbach et al., *Infect Control Hosp Epidemiol* 30:1186-1192 (2009); Metan et al., *Eur J Intern Med* 20:540-544 (2009); Park et al., *Diagn Microbiol Infect Dis* 64:43-51 (2009); Perez et al., *Am J Infect Control* 38:63-65 (2007); Sunenshine et al., *Emerg Infect Dis* 13:97-103 (2007). Indeed, bloodstream infections caused by XDR *A. baumannii* cause >50-60% mortality rates despite antibiotic therapy (Gordon and Wareham, *J Antimicrob Chemother* 63:775-780 (2009); Metan et al., *Eur J Intern Med* 20:540-544 (2009); Munoz-Price et al., *Infect Control Hosp Epidemiol* 1(10):1057-62 (2010); Park et al., *Diagn Microbiol Infect Dis* 64:43-51 (2009); Tseng et al., *Diagn Microbiol Infect Dis* 59:181-190 (2007). A major reason for these high mortality rates is that XDR *A. baumannii* infections are treatable only with suboptimal second-line antibacterial agents, such as tigecycline and colistin. Even more concerning is the increasing resistance of *A. baumannii* to both colistin and tigecycline (Adams et al., *Antimicrob Agents Chemother* 53:3628-3634 (2009); Doi et al., *Emerg Infect Dis* 15:980-982 (2009); Falagas et al., *Int J Antimicrob Agents* 32:450-454 (2008); Hernan et al., *Diagn Microbiol Infect Dis* 65:188-191 (2009); Livermore et al., *Int J Antimicrob Agents* 35:19-24 (2010); Park et al., *Diagn Microbiol Infect Dis* 64:43-51 (2009); Valencia et al., *Infect Control Hosp Epidemiol* 30:257-263 (2009); Wang and Dowzicky, *Diagn Microbiol Infect Dis* 68:73-79 (2010). Such pan-drug resistant (PDR) *A. baumannii* infections are resistant to every FDA approved antibiotic, and are hence untreatable.

New methods to prevent such XDR/PDR *A. baumannii* infections are critically needed, especially since no new drugs to treat these infections are in the antibacterial pipeline for the coming decade (Boucher et al., *Clin Infect Dis* 48:1-12 (2009); Spellberg et al., *Clin Infect Dis* 46:155-164 (2008). Since risk factors for *A. baumannii* infections are understood (Beavers et al., 2009; Caricato et al., *Intensive Care Med* 35:1964-1969 (2009); D'Agata et al., *Infect Control Hosp Epidemiol* 21:588-591 (2000); Furniss et al., *J Burn Care Rehabil* 26:405-408 (2005); Metan et al., *Eur J Intern Med* 20:540-544 (2009); Zakuan et al., *Trop Biomed* 26:123-129 (2009), vaccination of acutely at-risk patients is a promising method to prevent such infections, and antibody-based immunotherapy has promise to improve outcomes from infection.

SUMMARY OF INVENTION

The present invention provides vaccine compositions comprising OmpA, or antigenic fragments thereof, and related methods of active immunization against *A. baumannii* infection. The invention also provides antibodies and antigen-binding fragments thereof that specifically bind to OmpA, and related methods of passive immunization against *A. baumannii* infection. The compositions and methods of the invention are useful for preventing or treating *A. baumannii* infections, including those caused by strains resistant to carbapenems and all other antibiotics except colistin or tigecycline, also referred to as extreme drug resistant (XDR) *A. baumannii* infections, and those resistant to every FDA approved antibiotic, also referred to as pan-drug resistant (PDR) *A. baumannii* infections.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 4. OmpA sequence alignment across clinical isolates used in the current study. OmpA is >99% homologous at the amino acid level across six clinical isolates of *A. baumannii* harvested 58 years (1951-2009) apart (SEQ ID NOS:1-6), including carbapenem-susceptible and carbapenem-resistant strains.

FIG. 13. Comparison of sequences of known B and T cell epitopes to *A. baumannii* OmpA sequences from ATCC17978 and HUMC strains used to infect mice. CLUSTAL format alignment by MAFFT (v6.821b)(SEQ ID NOS:1-6 and 11, respectively). Yellow highlight=T cell epitopes (amino acids 1-18, 51-65, 151-153 and 221-235), Blue=B cell epitopes (amino acids 26-32, 91-130, 166, 265-280 and 307-331), Green=T and B cell epitopes (amino acids 19-25 and 154-165), Gray=mutation present in the prior art in the midst of B or T cell epitopes (amino acids 35F, 39N, 48M, 56T, 83I, 85V, 119A, 124A, 128V, 129F, 131G, 137V, 141M, 151E, 153E, 156P, 179I, 184A, 191G, 194H, 296A and 339N of SEQ ID NO:11).

DETAILED DESCRIPTION OF THE INVENTION

Figure 1:
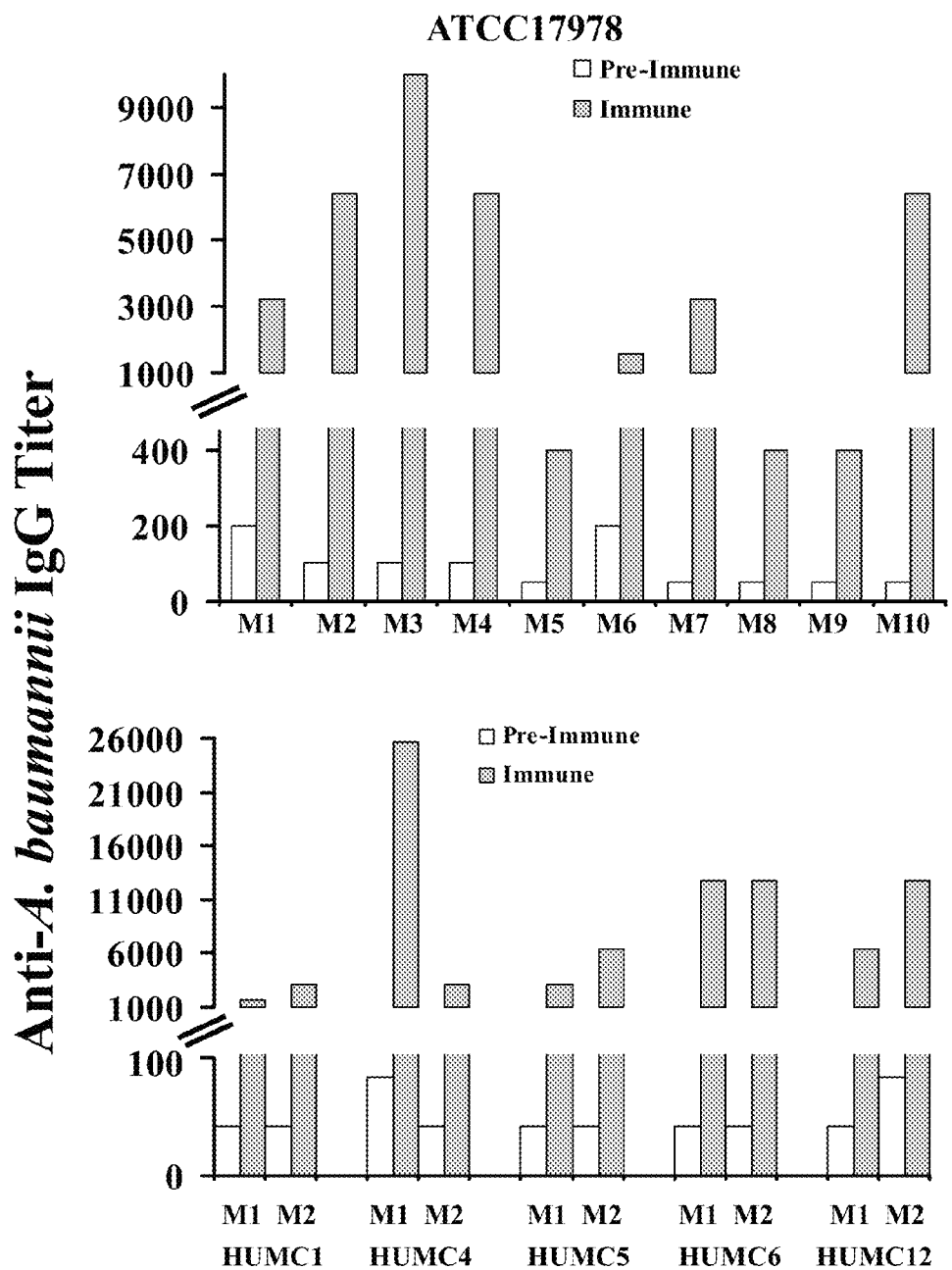
FIG. 1. *A. baumannii* infection induces specific humoral immune response. Ten mice were infected with ATCC 17978 (top) and 2 mice each were infected with clinical isolates from Harbor-UCLA Medical Center (HUMC) (bottom). Paired pre-immune & immune serum IgG anti-*A. baumannii* cell membrane protein titers are shown.

The present invention is based, in part, on the discovery of *A. baumannii* OmpA as an antigen target for an *A. baumannii*-targeted vaccine. The present invention provides vaccine compositions comprising OmpA, or antigenic fragments thereof, and related methods of active immunization against *A. baumannii* infection. The invention also provides antibodies and antigen-binding parts thereof that specifically bind to OmpA, and related methods of passive immunization against *A. baumannii* infection. The compositions and methods of the invention are useful for preventing or treating *A. baumannii* infections, including those caused by strains resistant to carbapenems and all other antibiotics except colistin or tigecycline, also referred to as extreme drug resistant (XDR) *A. baumannii* infections, and those resistant to every FDA approved antibiotic, also referred to as pan-drug resistant (PDR) *A. baumannii* infections.

As described herein, OmpA provides an antigen for an *A. baumannii*-targeted vaccine. As described in the examples, OmpA was identified as a vaccine based on humoral immunodominance during infection in mice. OmpA was highly conserved across multiple clinical isolates, and shared minimal homology with the human proteome.

Over the past decade *A. baumannii* has emerged to become one of the most antibiotic-resistant causes of infections all over the world, with unacceptably high resulting mortality rates. No new treatments capable of treating XDR/PDR *A. baumannii* are likely to become available during the coming decade and this invention provides novel strategies to prevent and treat such infections based on discovery of an antigen for an *A. baumannii*-targeted vaccine. rOmpA was identified as a vaccine based on humoral immunodominance during infection in mice. OmpA was highly conserved across multiple clinical isolates, and shared minimal homology with the human proteome. Substantial efficacy was seen in highly and rapidly lethal murine models in immunocompromised, DKA mice when administered with Al(OH)3 adjuvant, and will also be observed in a rat model of aspiration pneumonia. Efficacy in two distinct models with Al(OH)3 demonstrates translatability of the vaccine candidate, since Al(OH)3 is one of the most widely used adjuvants in the world, and has an established safety and efficacy record after dosing in millions of patients over more than a half century (Lindblad, *Vaccine* 22:3658-3668 (2004); Lindblad, *Immunol Cell Biol* 82:497-505 (2004).

As exemplified herein, individual mouse antibody titers correlated with survival, and IgG titer cut-offs of ≥1:102,400 or 1:204,800 were highly accurate at predicting which mice survived. Furthermore, immune sera was the effector of vaccine-mediated protection, and was effective during passive immunization. It has been previously reported that *A. baumannii* is resistant to complement-mediated killing (Kim et al., *FEMS Microbiol Lett* 301:224-231 (2009); King et al., *FEMS Microbiol Lett* 301:224-231 (2009) which is concordant with the current study results. Immunization-induced protection against *A. baumannii* was mediated by enhancing opsonophagocytic killing of the organism. These results are concordant with the fact that neutropenic mice are susceptible to *A. baumannii* infection (van Faassen et al., *Infect Immun* 75:5597-5608 (2007) and the fact that superoxide-deficient, gp91phox–/– mice were hypersusceptible to *A. baumannii* intranasal infection (Qiu et al., *Infect Immun* 75:5597-5608 (2009). Collectively, these results confirm that enhanced uptake and killing of *A. baumannii* by antibody-based opsonophagocytosis lead to more effective clearance of *A. baumannii* from tissue.

*A. baumannii* OmpA has been found to have a variety of interesting biological properties in model systems. For example, OmpA has been shown to bind to eukaryotic cells, translocate to the nucleus, and induce cell death (Choi et al., *Cell Microbiol* 10:309-319 (2008); McConnell and Pachon, *Protein Expr Purif* 77(1):98-103 (2010).

OmpA is a novel vaccine that can prevent XDR/PDR *A. baumannii* infections. As exemplified herein, efficacy has been established at feasible doses with a translatable adjuvant.

The present invention provides a method of prophylactic or therapeutic treatment of *A. baumannii* infection in a mammalian subject, preferably human, comprising administering to the subject an immunologically effective amount of a *A. baumannii* OmpA vaccine composition, antibody composition or antiserum of the invention as described herein. In one embodiment, the invention provides a method of prophylactic or therapeutic treatment of *A. baumannii* infection in a subject, comprising administering to the subject an immunologically effective amount of a vaccine composition comprising an *A. baumannii* outer membrane protein A (OmpA), or an antigenic fragment thereof. In a particular embodiment, the subject is a human.

The term "OmpA" or "*A. baumannii* OmpA" as used herein, means an outer membrane protein A of *A. baumannii* that corresponds to any of the amino acid sequences shown in FIG. 4. The term also includes art-known OmpA amino acid sequences that are substantially similar in sequence, immunogenicity and function, including, for example, one or more of the OmpA sequences set forth in Table 1, which are incorporated herein by reference to their NCBI Accession.Version and gi sequence identifiers. An OmpA sequence of the invention can be, for example, at least 80 percent, at least 85 percent, at least 87 percent, at least 88 percent, at least 89 percent, at least 90 percent, at least 91 percent, at least 92 percent, at least 93 percent, at least 94 percent, at least 95 percent, at least 96 percent, at least 97 percent, at least 98 percent, at least 99 percent, identical to a sequence set forth in FIG. 4. An OmpA of the invention can, for example, be less than 360 amino acids in length, less than 359 amino acids in length, less than 358 amino acids in length, less than 357 amino acids in length, less than 356 amino acids in length, less than 355 amino acids in length, less than 354 amino acids in length, less than 353 amino acids in length, less than 352 amino acids in length, less than 350 amino acids in length, less than 349 amino acids in length, less than 348 amino acids in length, less than 347 amino acids in length, less than 346 amino acids in length, less than 345 amino acids in length. An OmpA protein can be 346 amino acids in length. An *A. baumannii* OmpA amino acid sequence useful in the compositions and methods of the invention is substantially similar to the sequences set forth in Table 4 and can either be isolated or recombinantly prepared (rOmpA). An OmpA of the present invention can have unexpectedly high immunogenicity when compared to an OmpA that is not, for example, at least 80 percent, at least 85 percent, at least 87 percent, at least 88 percent, at least 89 percent, at least 90 percent, at least 91 percent, at least 92 percent, at least 93 percent, at least 94 percent, at least 95 percent identical in amino acid sequence.

TABLE 1

*A. baumannii* OmpA Sequences

| NCBI OmpA Accession.Version Number | NCBI OmpA gi Number |
|---|---|
| AAR83911.1 | 40287452 |
| Q6RYW5.1 | 75438841 |
| CAP01862.1 | 169152833 |
| CAP01565.1 | 169152583 |
| CAP00823.1 | 169151962 |
| CAO99984.1 | 169151288 |
| AAM73654.1 | 21666310 |
| CAP16950.1 | 261599880 |
| CAP16951.1 | 261599781 |
| ACA13273.1 | 167966448 |
| ACA13272.1 | 167966446 |
| ABY47586.1 | 163866832 |
| ABY47585.1 | 163866830 |
| ABY47584.1 | 163866828 |
| ABY47583.1 | 163866826 |
| ABY47582.1 | 163866824 |
| ACB12042.1 | 170280279 |
| ABG77310.1 | 110589616 |
| ABG77309.1 | 110589614 |
| ABG37059.1 | 109675220 |
| ABG37058.1 | 109675218 |
| ABO30516.1 | 129307156 |
| ABO30515.1 | 129307154 |
| ADX93822.1 | 323519441 |
| ADX93729.1 | 323519348 |

TABLE 1-continued

*A. baumannii* OmpA Sequences

| NCBI OmpA Accession.Version Number | NCBI OmpA gi Number |
|---|---|
| ADX91906.1 | 323517525 |
| ADX91788.1 | 323517407 |
| ADX91300.1 | 323516919 |
| YP_001847847.1 | 184159508 |
| YP_001847748.1 | 184159409 |
| YP_001845964.1 | 184157625 |
| YP_001845831.1 | 184157492 |
| YP_001845494.1 | 184157155 |
| ZP_07242161.1 | 301597153 |
| ACJ58603.1 | 213988304 |
| ACJ58458.1 | 213988159 |
| ACJ58275.1 | 213987976 |
| ACJ58171.1 | 213987872 |
| ACJ56927.1 | 213986628 |
| ADX04874.1 | 322509420 |
| ADX04775.1 | 322509321 |
| ADX03387.1 | 322507933 |
| ADX03261.1 | 322507807 |
| ADX02506.1 | 322507052 |
| ZP_07242881.1 | 301597873 |
| ZP_07240024.1 | 301595016 |
| ZP_07238125.1 | 301512888 |
| ZP_07237966.1 | 301512729 |
| ZP_07237394.1 | 301512157 |
| ZP_07227965.1 | 301347224 |
| ZP_07226657.1 | 301345916 |
| ZP_07226582.1 | 301345841 |
| ZP_07226176.1 | 301345435 |
| ZP_06798301.1 | 294860532 |
| ZP_06797604.1 | 294859835 |
| ZP_06796576.1 | 294858807 |
| ZP_06795340.1 | 294857571 |
| ZP_06794866.1 | 294857097 |
| ZP_06787675.1 | 294842992 |
| ZP_06786321.1 | 294841638 |
| ZP_06785798.1 | 294841115 |
| ZP_06785735.1 | 294841052 |
| ZP_06785088.1 | 294840405 |
| ZP_06784877.1 | 294840194 |
| ZP_06784301.1 | 294839618 |
| ZP_06783732.1 | 294839049 |
| ZP_06783190.1 | 294838507 |
| ZP_06781529.1 | 294836846 |
| ZP_04663447.1 | 239504137 |
| ZP_04662491.1 | 239503181 |
| ACC58500.1 | 183211102 |
| ACC58401.1 | 183211003 |
| ACC56617.1 | 183209219 |
| ACC56484.1 | 183209086 |
| ACC56147.1 | 183208749 |
| A3M8K2.2 | 148839593 |
| YP_001714728.1 | 169796935 |
| YP_001714391.1 | 169796598 |
| YP_001714238.1 | 169796445 |
| YP_001712610.1 | 169794817 |
| YP_001712475.1 | 169794682 |
| YP_001707777.1 | 169634041 |
| YP_001707527.1 | 169633791 |
| YP_001706906.1 | 169633170 |
| YP_001706232.1 | 169632496 |
| ABO13390.2 | 193078408 |
| ABO13246.2 | 193078282 |
| ABO11733.2 | 193076988 |
| ABO11623.2 | 193076900 |
| ABO11316.1 | 126386818 |
| CAM87753.1 | 169149862 |
| CAM87414.1 | 169149525 |
| CAM87256.1 | 169149372 |
| CAM85607.1 | 169147744 |
| CAM85470.1 | 169147609 |
| ZP_07237827.1 | 301512590 |
| YP_002326628.1 | 215484397 |
| YP_002326284.1 | 215484059 |
| YP_002326132.1 | 215483907 |
| YP_002324545.1 | 215482363 |
| YP_002324452.1 | 215482270 |
| YP_002320744.1 | 213157946 |
| YP_002320655.1 | 213157857 |
| YP_002318323.1 | 213156662 |
| YP_002318864.1 | 213156444 |
| YP_001085992.1 | 126643008 |
| YP_001085848.1 | 126642864 |
| YP_001084335.1 | 126641351 |
| YP_001084225.1 | 126641241 |
| YP_001083918.1 | 126640934 |
| ACJ42008.1 | 213057106 |
| ACJ41919.1 | 213057017 |
| ACJ40724.1 | 213055822 |
| ACJ40506.1 | 213055604 |
| ZP_07240179.1 | 301595171 |
| ZP_07235999.1 | 301510762 |
| ZP_07225482.1 | 301344741 |
| ZP_05830321.1 | 260558111 |
| ZP_05829775.1 | 260557560 |
| ZP_05829399.1 | 260557183 |
| ZP_05827995.1 | 260555775 |
| ZP_05827733.1 | 260555512 |
| ACA09703.1 | 167888787 |
| EEX05351.1 | 260412054 |
| EEX03984.1 | 260410686 |
| EEX02591.1 | 260409289 |
| EEX02489.1 | 260409186 |
| EEX01692.1 | 260408384 |

The present invention provides an antigenic composition comprising at least one antigen, wherein said at least one antigen comprises at least part of a protein or polypeptide of *A. baumannii* OmpA and comprises at least one antigenic epitope or antigenic determinant of *A. baumannii* OmpA. In one embodiment of the invention, the antigenic composition comprises at least one antigen that is recombinantly produced. It is further contemplated that the antigenic composition comprises at least one antigen that is an isolated or purified antigen. In a further embodiment of the invention, the antigenic composition comprises at least one recombinant vector and at least one polynucleotide inserted therein that encodes said at least one protein or polypeptide, wherein the vector is able to express said polypeptide in vivo in a mammalian subject susceptible to infection with *A. baumannii*. The antigenic *A. baumannii* OmpA composition of the invention can be an immunogenic composition.

In a particular embodiment, the invention provides an isolated polypeptide comprising an amino acid sequence selected from SEQ ID NOS:1-6. Such polypeptides are useful in compositions of the invention, for example, pharmaceutical compositions and/or vaccine compositions. Such a vaccine composition can further comprise an adjuvant.

In another embodiment, the invention provides a composition comprising an antigenic fragment of an amino acid sequence selected from SEQ ID NOS:1-6, wherein the antigenic fragment comprises an amino acid sequence that differs from at least one amino acid of the amino acid sequence of SEQ ID NO:11, or wherein the antigenic fragment comprises an amino acid sequence selected from SEQ ID NOS:7-10 and amino acids 1-18, 19-25, 26-32, 51-65, 91-130, 151-153, 154-165, 166, 221-235, 265-280 and 307-331 of SEQ ID NOS:1-6 (see Examples and FIG. 13). In a further embodiment, the composition contains an antigenic fragment that has at least one amino acid that differs from the sequence of SEQ ID NO:11 at amino acids 35F, 39N, 48M, 56T, 83I, 85V, 119A, 124A, 128V, 129F, 131G, 137V, 141M, 151E, 153E, 156P, 179I, 184A, 191G, 194H, 296A and 339N (see FIG. 13). Such antigenic fragments can be, for example, less than 360 amino acids in length less than 359 amino acids in length, less than 358 amino acids in length, less than 357 amino acids in length, less than 356 amino acids in length, less than 355 amino acids in length, less than 354 amino acids in length, less than 353 amino acids in length, less than 352 amino acids in length, less than 350 amino acids in length, less than 349 amino acids in length, less than 348 amino acids in length, less than 347 amino acids in length, less than 346 amino acids in length, less than 345 amino acids in length. In addition, the antigenic fragments can be, for example, less than 340 amino acids in length, less than 335 amino acids in length, less than 330 amino acids in length, less than 325 amino acids in length, less than 320 amino acids in length, less than 315 amino acids in length, less than 310 amino acids in length, less than 305 amino acids in length, less than 300 amino acids in length, less than 295 amino acids in length, less than 290 amino acids in length, less than 285 amino acids in length, less than 280 amino acids in length, less than 275 amino acids in length, less than 270 amino acids in length, less than 265 amino acids in length, less than 260 amino acids in length, less than 255 amino acids in length, less than 250 amino acids in length, less than 245 amino acids in length, less than 240 amino acids in length, less than 235 amino acids in length, less than 230 amino acids in length, less than 225 amino acids in length, less than 220 amino acids in length, less than 215 amino acids in length, less than 210 amino acids in length, less than 205 amino acids in length, less than 200 amino acids in length, less than 195 amino acids in length, less than 190 amino acids in length, less than 185 amino acids in length, less than 180 amino acids in length, less than 175 amino acids in length, less than 170 amino acids in length, less than 165 amino acids in length, less than 160 amino acids in length, less than 155 amino acids in length, less than 150 amino acids in length, less than 145 amino acids in length, less than 140 amino acids in length, less than 135 amino acids in length, less than 130 amino acids in length, less than 125 amino acids in length, less than 120 amino acids in length, less than 115 amino acids in length, less than 110 amino acids in length, less than 105 amino acids in length, less than 100 amino acids in length, less than 95 amino acids in length, less than 90 amino acids in length, less than 85 amino acids in length, less than 80 amino acids in length, less than 75 amino acids in length, less than 70 amino acids in length, less than 65 amino acids in length, less than 60 amino acids in length, less than 55 amino acids in length, less than 50 amino acids in length, less than 45 amino acids in length, less than 40 amino acids in length, less than 35 amino acids in length, less than 30 amino acids in length, less than 25 amino acids in length, less than 20 amino acids in length, or less than 15 amino acids in length.

The invention further provides an isolated nucleic acid molecule encoding an amino acid sequence selected from SEQ ID NOS:1-6 as well as compositions comprising such nucleic acid molecules. The invention additionally provides a vector comprising the isolated nucleic acid molecules of the invention. The invention also provides vaccine composition comprising the nucleic acid composition of the invention or a vector containing the nucleic acid molecules of the invention.

The invention further provides a composition comprising a nucleic acid molecule encoding an antigenic fragment of an amino acid sequence selected from SEQ ID NOS:1-6, wherein the antigenic fragment comprises an amino acid sequence that differs from at least one amino acid of the amino acid sequence of SEQ ID NO:11, or wherein the antigenic fragment comprises an amino acid sequence selected from SEQ ID NOS:7-10 and amino acids 1-18, 19-25, 26-32, 51-65, 91-130, 151-153, 154-165, 166, 221-235, 265-280 and 307-331 of SEQ ID NOS:1-6. In a particular embodiment, such a nucleic acid composition can encode an amino acid sequence, wherein the at least one amino acid differs from the sequence of SEQ ID NO:11 at amino acids 35F, 39N, 48M, 56T, 83I, 85V, 119A, 124A, 128V, 129F, 131G, 137V, 141M, 151E, 153E, 156P, 179I, 184A, 191G, 194H, 296A and 339N.

An "antigenic fragment," "antigenic epitope" or "antigenic determinant" of A. baumannii OmpA refers to a portion of A. baumannii OmpA that either includes or corresponds to a sequential or conformational immunologically active region that is recognized and bound by lymphocytes or secreted antibodies. An antigenic fragment can be any portion up to full length of A. baumannii OmpA, for example, at least between 300 to 350 amino acids, at least between 250 to 300 amino acids, at least between 200 to 250 amino acids, at least between 150 to 200 amino acids, at least between 100 to 150 amino acids, at least between 50 to 100 amino acids, at least between 20 to 50 amino acids, at least between 10 to 20 amino acids, at least between 2 to 10 amino acids, at least between 4 to 8 amino acids, at least between 5 to 7 amino acids.

In a further embodiment, the invention provides a vaccine composition for protecting a mammalian subject against infection of A. baumannii OmpA that comprises an A. baumannii OmpA or antigenic fragment thereof, as described herein as immunizing component, and a pharmaceutically acceptable carrier. The vaccine compositions of the invention comprise detoxified A. baumannii OmpA or antigenic fragment thereof that are substantially free of endotoxin. In certain embodiments, the vaccine composition can further include an adjuvant, for example, aluminium hydroxide (AL(OH)$_3$) or other aluminum-containing adjuvant. Hem, S. L. and HogenEsch, H. (2006) Aluminum-Containing Adjuvants: Properties, Formulation, and Use, in Vaccine Adjuvants and Delivery Systems (ed M. Singh), John Wiley & Sons, Inc., Hoboken, N.J., USA. doi: 10.1002/9780470134931.ch4. Methods for selecting an appropriate adjuvant are well known in the art and described, for example, in Vaccine Adjuvants and Delivery Systems (ed M. Singh), John Wiley & Sons, Inc., Hoboken, N.J., USA. doi: 10.1002/9780470134931.

The vaccine composition provided by the invention protects susceptible mammals, preferably human subjects, against one or more manifestations of A. baumannii infection, for example, blood stream infection, hospital and community-acquired pneumonia, kidney infection, urinary tract infection, bladder infection, wound infection, meningitis, endocarditis, endopthalmitis, and keratitis caused by A. baumannii. In some embodiments, the susceptible human subject is afflicted with diabetes, hypertension, liver cirrhosis, renal insufficiency, human immunovirus infection, neutropenia (absolute neutrophil count more than 500 cells/mm), malignancy, decubitus ulcers, septic shock, and anoxic encephalopathy; undergoing dialysis or immunosuppressive treatment; is a transplant recipient or tracheostomy patient, uses a mechanical ventilator. The vaccine composition of the invention can be particularly indicated for active vaccination of hospital patients to prevent infections and military personnel as A. baumannii is one of the most common causes for wound infection.

The vaccine composition of the invention can be provided in a physiologically administrable form, and suitably is administrable by subcutaneous or intranasal inoculation.

The present invention, in additional embodiments, also provides a method for producing an antigen or an immunogen of an antigenic composition. The method comprises (a) providing a DNA fragment encoding said antigen and introducing said fragment into an expression vector; (b) introducing said vector, which contains said DNA fragment, into a compatible host cell; (c) culturing said host cell provided in step (b) under conditions required for expression of the product encoded by said DNA fragment; and (d) isolating the expressed product from the cultured host cell, and, optionally, (e) purifying the isolated product from step (d) by affinity chromatography or other chromatographic methods known in the art.

In a further embodiment, the invention provides a method for preparation of a vaccine composition that contains as immunizing component, an antigenic or immunogenic composition of the invention. The method comprises mixing an antigenic or immunogenic composition and a pharmaceutically acceptable carrier. Also provided is a method for the production of an antiserum that includes administering an antigenic preparation of the invention to a mammalian host to produce antibodies in the host and recovering antiserum containing the antibodies produced in the host. Also provided is a method of prophylactic or therapeutic treatment of *A. baumannii* infection in mammalian subject, suitably human, comprising administering to the subject an immunologically effective amount of a vaccine composition or antiserum of the invention as described herein. In a further embodiment, the invention provides a method for protecting a mammalian subject against *A. baumannii* infection, or reducing the severity of the infection, which comprises inoculating the subject subcutaneously or intranasally with a vaccine composition of the invention to induce an immune response against *A. baumannii* in the subject.

The invention also provides an antibody preparation for passive immunization comprising at least one antibody, or antigen-binding fragment hereof, specific for an *A. baumannii* OmpA protein or polypeptide of the invention. The antibody preparation can be used prophylactically or therapeutically against an *A. baumanni* infection and can further provide passive immunization when administered to a mammalian subject susceptible to infection by *A. baumannii*. The passive immunization can be an adjunct therapy to other treatments, including active immunization.

In a particular embodiment, the invention provides a composition comprising an antibody, or antigen binding fragment thereof, wherein the antibody or antigen binding fragment specifically binds to an epitope encoded by an amino acid sequence selected from SEQ ID NOS:1-6. In a further embodiment, the epitope can comprise an antigenic fragment comprising an amino acid sequence that differs from at least one amino acid of the amino acid sequence of SEQ ID NO:11, or wherein the antigenic fragment comprises an amino acid sequence selected from SEQ ID NOS:7-10 and amino acids 1-18, 19-25, 26-32, 51-65, 91-130, 151-153, 154-165, 166, 221-235, 265-280 and 307-331 of SEQ ID NOS:1-6. For example, the at least one amino acid can differ from the sequence of SEQ ID NO:11 at amino acids 35F, 39N, 48M, 56T, 83I, 85V, 119A, 124A, 128V, 129F, 131G, 137V, 141M, 151E, 153E, 156P, 179I, 184A, 191G, 194H, 296A and 339N.

The amount of vaccine of the invention to be administered a human or animal and the regime of administration can be determined in accordance with standard techniques well known to those of ordinary skill in the pharmaceutical and veterinary arts taking into consideration such factors as the particular antigen, the adjuvant (if present), the age, sex, weight, species and condition of the particular animal or patient, and the route of administration. In the present invention, the amount of polysaccharide-protein carrier to provide an efficacious dose for vaccination against *N. meningitidis* can be from between about 0.02 µg to about 5 µg per kg body weight. In a preferred composition and method of the present invention the dosage is between about 0.1 µg to 3 µg per kg of body weight. For example, an efficacious dosage will require less antibody if the post-infection time elapsed is less since there is less time for the bacteria to proliferate. In like manner an efficacious dosage will depend on the bacterial load at the time of diagnosis. Multiple injections administered over a period of days can be considered for therapeutic usage. The compositions of the present invention can be administered as a single dose or in a series (i.e., with a "booster" or "boosters"). In one embodiment of the invention, a preferred route of administration is intramuscular or subcutaneous, with intramuscular route preferred. Administration can be by injection or by an alternative delivery device.

In a preferred embodiment of the invention, the vaccine composition is formulated as a sterile liquid, pyrogen-free, phosphate-buffered physiological saline, with or without a preservative. The choice of suitable carriers and other additives will depend on the exact route of administration and the nature of the particular dosage form, e.g., liquid dosage for (e.g., whether the composition is to be formulated into a solution, a suspension, gel or another liquid form), or solid dosage form (e.g., whether the composition is to be formulated into a pill, tablet, capsule, caplet, time release form or liquid-filled form).

An antibody of the invention, or a fragment thereof, specifically binds to *A. baumannii* OmpA and is well tolerated by the human immune system.

An antibody refers to a full-length (i.e., naturally occurring or formed by normal immunoglobulin gene fragment recombinatorial processes) immunoglobulin molecule (e.g., an IgG antibody) or an immunologically active, antigen-binding portion of an immunoglobulin molecule, like an antibody fragment. As described in more detail below, an antibody fragment is a portion of an antibody such as $F(ab')_2$, $F(ab)_2$, Fab', Fab, Fv, scFv and the like. Regardless of structure, an antibody fragment binds with the same antigen that is recognized by the intact antibody. The term antibody fragment also includes isolated fragments consisting of the variable regions, such as the "Fv" fragments consisting of the variable regions of the heavy and light chains and recombinant single chain polypeptide molecules in which light and heavy variable regions are connected by a peptide linker ("scFv proteins"). As used herein, the term antibody fragment does not include portions of antibodies without antigen binding activity, such as Fc fragments or single amino acid residues. Other antibody fragments, for example single domain antibody fragments, are known in the art and can be used in the claimed constructs. (See, e.g., Muyldermans et al., *TIBS* 26:230-235, 2001; Yau et al., *J Immunol Methods* 281:161-75 (2003); Maass et al., *J Immunol Methods* 324:13-25 (2007); Harlow and Lane, *Antibodies: A Laboratory Manual*, Cold Spring Harbor Laboratory, Cold Spring Harbor N.Y. (1988)).

In one embodiment, the invention provides an antibody, or fragment thereof, that selectively binds to *A. baumannii* OmpA, or an antigenic fragment thereof and is humanized or fully human. The antibody, or fragment thereof, displays a high affinity for *A. baumannii* OmpA, or an antigenic fragment thereof. The present invention therefore relates to monoclonal or polyclonal antibodies, and fragments thereof, which bind specifically to an *A. baumannii* OmpA, or an antigenic fragment thereof.

The antibody of the invention, or fragment thereof, is preferably chosen so that it has particular binding kinetics (e.g. high affinity, little dissociation, low off rate, strong neutralizing activity) for the specific binding to *A. baumannii* OmpA, or an antigenic fragment thereof. The antibodies are preferably isolated antibodies. According to a further aspect, the antibodies are neutralizing antibodies. The antibodies of the invention include in particular monoclonal and recombinant antibodies. A monoclonal antibody of the invention is derived from a hybridoma (e.g. an antibody which is secreted by a hybridoma produced by means of hybridoma technology such as the standardized hybridoma methods of Miller and Milstein). An antibody of the invention can be derived from a hybridoma and have specificity for an *A. baumannii* OmpA, or an antigenic fragment thereof.

The antibodies of the invention can comprise an amino acid sequence that derives completely from a single species, and thus can be for example a human antibody or a mouse antibody. According to further embodiments, the antibody can be a chimeric antibody or a CDR graft antibody or another type of humanized antibody.

The term "antibody" is intended to refer to immunoglobulin molecules that are formed of four polypeptide chains, two heavy (H) chains and two light (L) chains. The chains are usually linked together by disulfide bonds. Every heavy chain is composed of a variable region of the heavy chain (abbreviated here to HCVR or VH) and a constant region of the heavy chain. The constant region of the heavy chain is formed from three domains CH1, CH2 and CH3. Each light chain is composed of a variable region of the light chain (abbreviated here to LCVR or VL) and a constant region of the light chain. The constant region of the light chain is formed from a CL domain. The VH and VL regions may be further divided into hypervariable regions which are referred to as complementarity-determining regions (CDR) and are interspersed with more conserved regions which are referred to as framework regions (FR). Each VH and VL region is formed from three CDRs and four FRs which are arranged from the N terminus to the C terminus in the following sequence: FR1, CDR1, FR2, CDR2, FR3, CDR3, FR4.

The term "fragment" or "antigen-binding fragment" or "binding fragment" used in reference to an antibody refers to one or more fragments of an antibody having specificity for an *A. baumannii* OmpA, the fragment(s) still having the ability to bind specifically the *A. baumannii* OmpA, or an antigenic fragment thereof. It has been shown that the antigen-binding function of an antibody can be undertaken by fragments of a complete antibody. Examples of binding fragments include an antibody (i) an Fab fragment, i.e. a monovalent fragment composed of the VL, VH, CL and CH1 domains; (ii) an F(ab).sub.2 fragment, i.e. a bivalent fragment which comprises two Fab fragments linked together by a disulfide bridge in the hinge region; (iii) an Fd fragment which is composed of the VH and CH1 domains; (iv) an Fv fragment which is composed of the VL and VH domains of a single arm of an antibody; (v) a dAb fragment (Ward et al., (1989) Nature 341:544-546) which consists of a VH domain or VH, CH1, CH2, DH3, or VH, CH2, CH3; and (vi) an isolated complementarity-determining region (CDR). Although the two domains of the Fv fragment, namely VL and VH, are encoded by separate genes they can furthermore be connected together by a synthetic linker by use of recombinant methods, whereby they can be produced as a single protein chain in which the VL and VH regions are present together in order to form monovalent molecules (known as single-chain Fv (ScFv), see, for example, Bird et al., Science 242:423-426 (1988); and Huston et al., *Proc. Natl. Acad. Sci. USA* 85:5879-5883 ((1988). Such single-chain antibodies are also intended to be encompassed by the term "antigenic fragment" of an antibody. Other types of single-chain antibodies such as diabodies likewise belong thereto. Diabodies are bivalent, bispecific antibodies in which VH and VL domains are expressed on a single polypeptide chain, but with use of a linker that is too short for the two domains to be present together on the same chain, the domains thus being forced to pair with complementary domains of another chain and to form two antigen-binding sites (see, for example, Holliger, P., et al., *Proc. Natl. Acad. Sci. USA* 90:6444-6448 (1993); Poljak, R. J., et al., *Structure* 2:1121-1123 (1994).

A further embodiment is for an antibody or antigen-binding fragment thereof to be part of a larger immunoadhesion molecule which is formed by covalent or non-covalent association of the antibody or antibody part with one or more further proteins or peptides. Such immunoadhesion molecules can involve the use of the streptavidin core region in order to produce a tetrameric scFv molecule (Kipriyanov, S. M., et al. *Human Antibodies and Hybridomas* 6:93-101 (1995) and the use of a cysteine residue, of a marker peptide and of a C-terminal polyhistidine tag in order to make bivalent and biotinylated scFv molecules (Kipriyanov, S. M., et al., *Mol Immunol* 31:1047-1058 (1994).

Antibody parts, such as Fab and $F(ab')_2$ fragments, can be produced from whole antibodies by using conventional techniques such as digestion with papain or pepsin. It is additionally possible to obtain antibodies, antibody parts and immunoadhesion molecules by using standardized recombinant DNA techniques.

An antibody specific to *A. baumannii* OmpA, or an antigen-binding fragment thereof can be produced, expressed, generated or isolated by using recombinant techniques, such as antibodies which are expressed by use of a recombinant expression vector transfected into a host cell; antibodies isolated from a recombinant combinatorial antibody library; antibodies isolated from an animal (e.g. a mouse) which is transgenic due to human immunoglobulin genes (see, for example, Taylor, L. D., et al., *Nucl Acids Res.* 20:6287-6295 (1992); or antibodies which are produced, expressed, generated or isolated in any other way in which particular immunglobulin gene sequences (such as human immunoglobulin gene sequences) are combined with other DNA sequences. Recombinant antibodies include, for example, chimeric, CDR graft and humanized antibodies.

A human antibody that has specificity for an *A. baumannii* OmpA has variable and constant regions corresponding to immunoglobulin sequences of the human germline, as described for example by Kabat et al. (see Kabat, et al. (1991) Sequences of Proteins of Immunological Interest, Fifth Edition, U.S. Department of Health and Human Services, NIH Publication No. 91-3242), or is derived therefrom. The human antibodies of the invention can, however, comprise amino acid residues which are not encoded by human germline immunglobulin sequences (e.g. mutations introduced by random or site-specific mutagenesis in vitro or by somatic mutation in vivo), for example in the CDRs, and especially in CDR3. Recombinant human antibodies of the invention have variable regions and can also comprise constant regions derived from immunoglobulin sequences of the human germline (see Kabat, E. A., et al. (1991) Sequences of Proteins of Immunological Interest, Fifth Edition, U.S. Department of Health and Human Services, NIH Publication No. 91-3242). According to particular embodiments, such recombinant human antibodies are, however, subjected to an in vitro mutagenesis (or to a somatic in vivo mutagenesis if an animal which is transgenic due to human Ig sequences is used), so that the amino acid sequences of the VH and VL regions of the recombinant antibodies are sequences which, although they are related to VH and VL sequences of the human germline or are derived therefrom, do not naturally exist within the human antibody germline repertoire in vivo. According to particular embodiments, such recombinant antibodies are the result of a selective mutagenesis or back-mutation, or both.

In a further embodiment, the invention provides methods of diagnosis of *A. baumannii* infection comprising obtaining a tissue sample from a subject suspected of *A. baumannii* infection, contacting the tissue sample suspected of comprising *A. baumannii* with an OmpA fragment, primer, antibody or antigen-binding fragment thereof and detecting the presence of *A. baumannii* OmpA in the sample by methods known in the art.

The invention will be further described by reference to the following illustrative, non-limiting examples setting forth in detail several preferred embodiments of the inventive concept. Other examples of this invention will be apparent to those skilled in the art without departing from the spirit of the invention.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

EXAMPLE I

Specific Anti-*A. baumannii* Antibodies are Generated During Infection in Mice Six clinical isolates of *A. baumannii* were used (Table 2). These isolates were harvested from various body sites of infection. Five of the strains were resistant to all antibiotics except for colistin (Table 5). Strain typing was performed by multi-locus sequence typing as previously described (Bartual et al., *J Clin Microbiol* 43:4382-4390 (2005); Tian et al., *Antimicrob Agents Chemother* 55:429-432 (2011). Balb/c mice were used for all experiments. For some experiments, retired breeder mice (>6 mo old) were used, whereas for other experiments juvenile (6-10 weeks old) Balb/c mice were used. Diabetes was induced by intraperitoneal injection of 200 mg/kg streptozotocin in 0.2 ml citrate buffer 10 days prior to infection. Glycosuria and ketonuria were confirmed in all mice 7 days after streptozotocin treatment, as previously described (Ibrahim et al., *J Antimicrob Chemother* 58:1070-1073 (2006); Ibrahim et al., *J Clin Invest* 117:2649-2657 (2007); Spellberg et al., *Antimicrob Agents Chemother* 49:830-832 (2005). Bacterial strains used are described in Table 2.

*A. baumannii* cell membrane preparations were produced by a modification of a standard, published method (Molloy et al., *Eur J Biochem* 267:2871-2881 (2000); Soares et al., *Proteome Sci* 7:37 2009). In brief, *A. baumannii* strains were grown overnight at 37° C. with shaking in tryptic soy broth (TSB). The bacteria were passaged to mid-log-growth at 37° C. with shaking. The cells were harvested by centrifugation at 3,500 g for 15 min at 4° C. and washed twice with 10 mL 0.9% (w/v) NaCl. The resultant pellet was resuspended in disintegration buffer (7.8 g/L $NaH_2PO_4$, 7.1 g/L $Na_2HPO_4$, 0.247 g/L MgSO4 7.$H_2$O+protease inhibitor mix (GE Healthcare, USA)+nuclease mix (GE Healthcare, USA)) and sonicated on ice for 3 periods of 5 min. The unbroken cells were separated by centrifugation at 1,500 g. The supernatant was centrifuged for 30 min at 4° C. at 4,500 rpm and was passed through a 0.45 µM filter (Milipore, USA) to remove cell debris. An equal volume of ice-cold 0.1 M sodium carbonate (pH 11) was added to the resulting supernatant and the mixture was stirred slowly overnight, on ice. The carbonate treated membrane proteins were collected by ultracentrifugation at 100,000 g for 45 min at 4° C., and the membranes were re-suspended in 500 µl $H_2O$. Finally, the protein extract was processed with a 2-DE Cleanup Kit (Bio-Rad, USA).

Two dimensional SDS/10%-PAGE gels of *A. baumannii* cell membrane preparations were used to separate proteins by size and isoelectric focusing (IEF), as described by Pitarch et al (Pitarch et al., *Mol Cell Proteomics* 5:79-96 (2006); Pitarch et al., *Electrophoresis* 20:1001-1010 (1999). For isoelectric focusing (IEF), the Bio-Rad-PROTEIN IEF system was used (Bio-Rad, USA) with 4-7 pH gradient strips (ReadyStrip IPG strips, Bio-Rad, USA). Proteins were solubilized in 8 M urea, 2% (w/v) CHAPS, 40 mM DTT and 0.5% (v/v) corresponding rehydrated buffer (Bio-Rad, USA). The strips were rehydrated overnight and underwent electrophoresis at 250 V for 20 min, 4000 V for 2 h, and 4,000 V for 10,000 V-h, all at room temperature. Prior to the second dimension (SDS-PAGE), the focused IPG strips were equilibrated with buffer I and II for 10 min (ReadyPrep 2-D Starter Kit, Bio-Rad, USA). The proteins were separated on 8-16% Criterion Pre-cast Gel (Bio-Rad, USA) and transferred to immune-Blot PVDF membranes (Bio-Rad, USA). Membranes were treated with Western Blocking Reagent (Roche) overnight and probed with pre-immune or immune *A. baumannii* infected-mice serum. Membranes were washed and incubated with secondary, HRP-conjugated goat anti-mouse IgG (Santa Cruz Biotech, USA). After incubation with SuperSignal West Dura Extended Duration Substrate (Pierce, USA), signals were detected using a CCD camera.

Protein spots of interest were excised and sent to the UCLA W. M. Keck Proteomic Center for identification on a Thermo LTQ-Orbitrap XL mass spectrometer (San Jose, Calif.) equipped with an Eksigent (Dublin, Calif.) NanoLiquid chromatography-1D plus system and an Eksigent autosampler. Proteins within the spots were in-gel tryptic digested as described by Shevchenko et al. (Shevchenko et al., *Proc Natl Acad Sci USA* 93:14440-14445 (1996); Shevchenko et al., *Anal Chem* 68:850-858 (1996). The eluted peptides were loaded onto a CVC Microtech (Fontana, Calif.) 35 mm length, 100 µm ID C18 pre-Trap column and washed for 10 min with 100% Buffer A (2% acetonitrile containing 0.1% formic acid) at a flow rate of 5 µl/min. The peptides were separated on a 15 cm New Objective ProteoPep IntegraFrit column (Woburn, Mass.) using a flow rate of 300 nl/min. The following elution gradient was used: 0-15 min 0-30% Buffer B (98% acetonitrile containing 0.1% formic acid), 15-20 min 30-80% Buffer B and 20-22 min 80% Buffer B. The column was then re-equilibrated for 13 min with Buffer A. The eluting analytes were sprayed in positive mode into the LTQ-Orbitrap MS using electrospray ionization voltage of 2300 V, capillary voltage of 45 V, tube lens of 130 V, and capillary temperature of 200° C. Information dependent acquisition was performed where the 6 most intense ions were selected in the m/z range of 300-1600 using a 60 K resolution FTMS scan and subjecting them to MS-MS using broadband collision induced disassociation of normalized collision energy of 35 and LTQ detection. Peaks were excluded from further MS-MS for a period of 60 sec.

The resulting MS/MS spectra was searched against the *Acinetobacter baumannii* strain ATCC 17978 database (gib.genes.nig.ac.jp/single/blast2/main.php?spid=Abau ATCC17978) using the Matrix Science MASCOT Daemon search engine (Boston, Mass.). The following search parameters were used: peptide tolerance: ±10 ppm, MS/MS tolerance ±0.3 Da, maximum missed cleavages: 2, fixed modifications: carboxymethyl (C) and variable modifications:

deamidization (ND) and oxidation (M). Proteins identified within a particular included those with a minimum of two unique peptides that are ranked as number 1 and with an ion scores with a p<0.05.

His-tagged rOmpA (amino acids 2 to 347) was produced in an *Escherichia coli* pQE-32 expression system (Qiagen) as previous described (Luo et al., *J Infect Dis* 201:1718-1728 (2010); Spellberg et al., *Infect Immun* 76:4574-4580 (2008). Briefly, ompA was amplified from *A. baumannii* 17978 genomic DNA with primers:

```
OmpA-F
                                         (SEQ ID NO: 12)
CATCACCATGGGATCCTTGTTGCTGCTCCATTAGCT
and OmpA-R
                                         (SEQ ID NO: 13)
CTAATTAAGCTTGGCTGCAGTTATTGAGCTGCTGCAGGA
``` and cloned into BamHII and Pst I sites of QE-32 by using In-Fusion 2.0 Dry-Down PCR Cloning Kit, per the manufacturer's instructions (Clontech Laboratories). The 6×-His (SEQ ID NO: 29) tagged protein was purified over a Ni-agarose affinity column according to the manufacturer instructions (Qiagen). Endotoxin was removed from rOmpA by using Detoxin Gel Endotoxin Removing Columns (Norgen Biotek, Canada), and the endotoxin level was determined with *Limulus Amebocyte* Lysate endochrome (Charles River) per manufacturer's instruction. Using this procedure, endotoxin was reduced to <1 EU per dose used for vaccination. Mice were immunized by subcutaneous injection of rOmpA in 0.1% Al(OH)$_3$ (Alhydrogel, Brenntag Biosector, Frederikssund, Denmark) in phosphate buffered saline (PBS). Control mice received adjuvant alone on the same schedule. Mice were immunized 5 weeks prior to infection and again 2 weeks prior to infection. Four days after the boost (10 days prior to infection), mice were rendered diabetic as described above.

*A. baumannii* strains were grown overnight at 37° C. with shaking in TSB broth. The bacteria were passaged to mid-log-growth at 37° C. with shaking Cells were washed twice with PBS and resuspended at the appropriate concentration for infection. The final concentration was confirmed by quantitative culturing of the inocula. Mice were infected iv via the tail-vein with sublethal ($10^6$) or lethal (targeted $2\times10^7$) inocula in PBS. All animal experiments were approved by the Institutional Committee on the Use and Care of Animals at the Los Angeles Biomedical Research Institute.

Two days after infection (the day on which control mice were anticipated to begin dying), organs were harvested and homogenized in sterile PBS with 1% triton with protease inhibitor cocktail (Sigma-Aldrich Corp. St. Louis, Mo., USA). Homogenized organs from individually marked mice were quantitatively cultured to determine tissue bacterial burden.

A previously published ELISA assay (Ibrahim et al., *Infect Immun* 74:3039-3041 (2006); Ibrahim et al., *Infect Immun* 73:999-1005 (2005); Spellberg et al., *J Infect Dis* 194:256-260 (2006); Spellberg et al., *Infect Immun* 73:6191-6193 (2005) was adapted for detection of antibodies against *A. baumannii* cell membrane preparations and rOmpA. In brief, ELISA plates were coated with 100 µl per well of 5 µg/ml of rOmpA or cell membrane preparation. Coated wells were blocked with bovine serum albumin, incubated with mouse sera, washed, and stained with goat anti-mouse secondary antibody conjugated with horseradish peroxidase. Wells were washed again and incubated with o-phenylenediamine substrate with $H_2O_2$. The color was allowed to develop for 20 min after which the reaction was terminated by adding equal volume of 3N HCl and the optical density (OD) was determined at 490 nm in a microtiter plate reader. Negative control wells received an irrelevant isotype control monoclonal antibody rather than mouse serum. The ELISA titer was taken as the reciprocal of the last serum dilution with an OD reading≥ (mean OD of negative control samples+(standard deviation*2)).

*A. baumannii* HUMC1 was cultured overnight in tryptic soy broth (TSB) at 37° C., passaged to mid-log growth, rinsed, and aliquoted into 96 well microtiter plates. For complement studies, non-immune or immune sera were added to the wells for 1 hour. Well contents were quantitatively cultured at baseline and again at 1 h. The opsonophagocytic kill assay was based on a modification of a previously used method [25-26]. Murine RAW 264.7 macrophage cells (both from American Type Culture Collection, Rockville, Md.) were tested because they are known to be capable of killing microbes after differentiation [15-17]. The cells were cultured at 37° C. in 5% $CO_2$ in RPMI 1640 (Irvine Scientific, Santa Ana, Calif.) with 10% fetal bovine serum (FBS), 1% penicillin, streptomycin, and glutamine (Gemini BioProducts), and 50 µM (3-mercaptoethanol (Sigma-Aldrich, St. Louis, Mo.). RAW 274.7 cells were activated by 3 days of exposure to 100 nM PMA (Sigma-Aldrich). Activated RAW 264.7 macrophages were harvested after scraping with BD Falcon cell scrapers (Fischer Scientific) and added to the microtiter wells at a 20:1 ratio of macrophages to bacteria. After a 1 hour incubation with gentle shaking, aliquots from the wells were quantitatively plated in tryptic soy agar (TSA). Colony forming units (CFU) of the co-cultured tubes were compared to CFUs of growth control tubes containing only microbes with no macrophages. Percent killing was calculated as 1—(CFUs from co-culture wells/CFUs from growth control wells without macrophages).

Survival was compared by the non-parametric Log Rank test. Antibody titers, bacterial burden, MPO levels, and cytokine levels were compared with the Wilcoxon Rank Sum test for unpaired comparisons or the Wilcoxon Signed Rank test for paired comparisons, as appropriate. Correlations were determined by the Spearman Rank test. All statistics were run using Kyplot. Differences were considered significant if the p value was <0.05.

As a basis for identifying lead antigenic candidates for vaccine development, the humoral immune response to surface proteins from *A. baumannii* was determined after natural infection. Since diabetes is a risk factor for acquisition of and worse outcomes from *A. baumannii* infection (Alsultan et al., *J Chemother* 21:290-295 (2009); Furniss et al., *J Burn Care Rehabil* 26:405-408 (2005); Metan et al., *Eur J Intern Med* 20:540-544 (2009), a diabetic ketoacidosis (DKA) mouse model of mucormycosis (Ibrahim et al., *J Antimicrob Chemother* 58:1070-1073 (2006); Ibrahim et al., *J Clin Invest* 117:2649-2657 (2007); Spellberg et al., *Antimicrob Agents Chemother* 49:830-832 (2005) was adapted for in vivo study of *A. baumannii* infections. Individually marked mice in DKA were bled via tail-vein nicking to determine baseline, pre-immune anti-*A. baumannii* cell membrane protein antibody titers. Mice were then infected via the tail-vein with survivable inocula of six clinical isolates of *A. baumannii* (Table 2 and Table 5). Two weeks post-infection, paired immune sera were obtained from the mice. ELISA of paired pre-immune vs. immune sera confirmed that mice infected with all of the strains generated substantial increases (10-100-fold) in anti-*A. baumannii* cell membrane IgG-antibody titers by 2 weeks post-infection (FIG. 1).

Figure 2A:
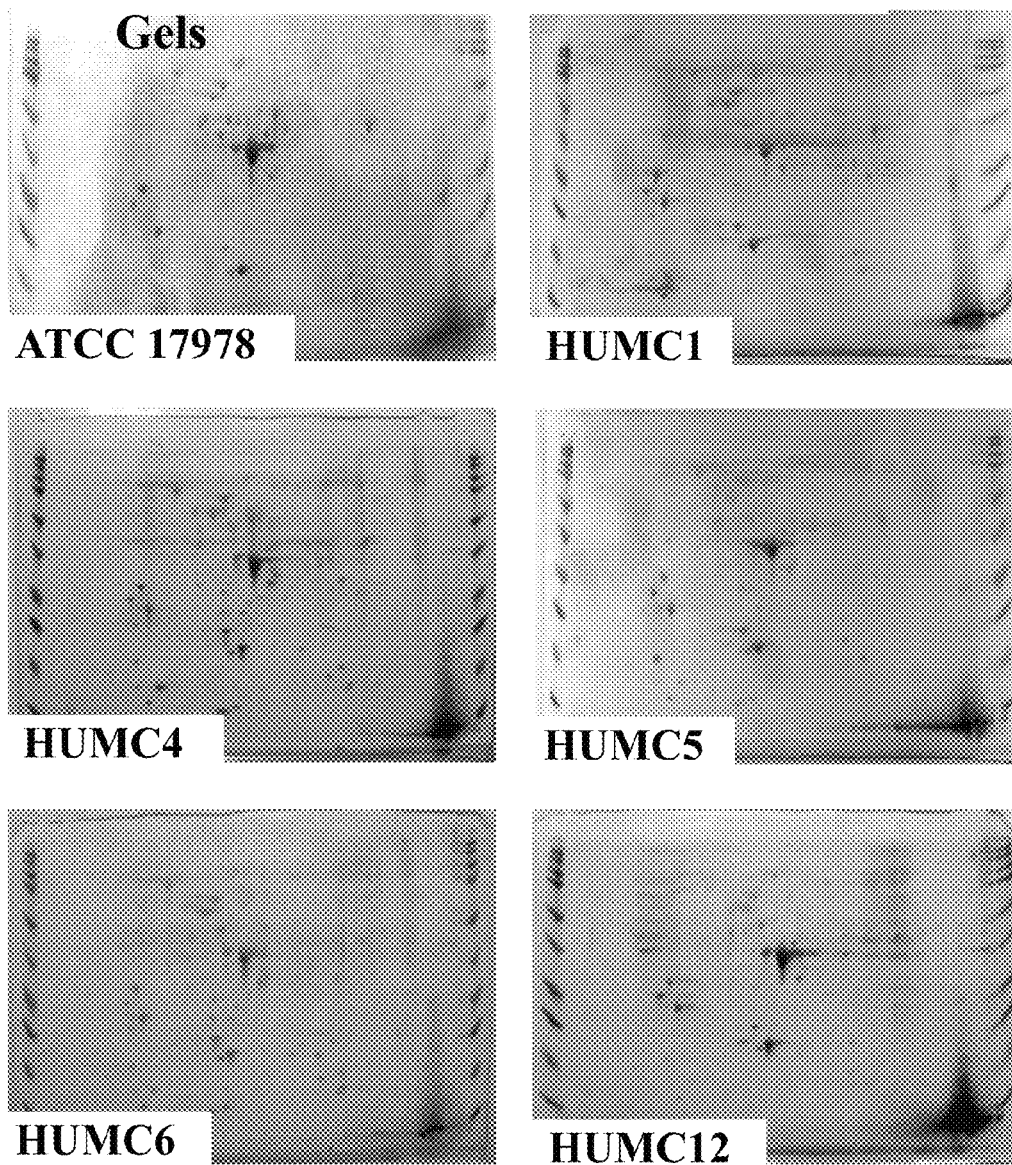
FIG. 2. 2 Dimensional PAGE-IEF gels and western blots of cell membrane protein extracts of *A. baumannii* clinical isolates. (A) Membrane protein preparations from *A. baumanni* clinical strains (ATCC 17978 & HUMC1, 4, 5, 6, & 12) were run on 2 D gels stained with Coomassie Blue. (B) Western blots of those 2D gels were stained with paired sera obtained from mice before infection (pre-serum) and after recovery from non-lethal iv infection (post-serum) with *A. baumannii*. Spots uniquely identified by post-immune serum were seen at conserved locations. Spots selected for protein identification by MALDI-TOF analysis are marked with white arrows.
Figure 2B:
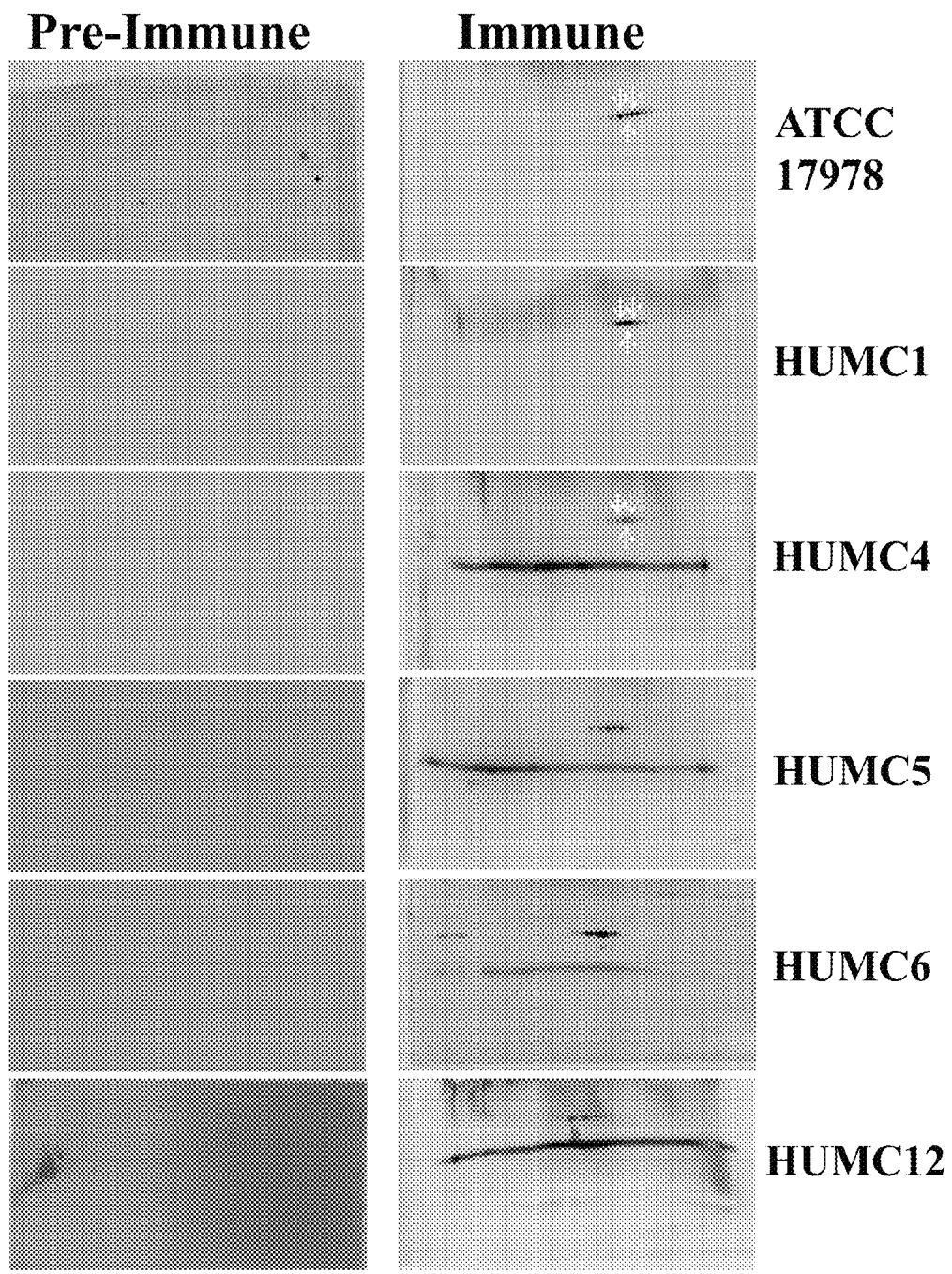

Having demonstrated a specific humoral immune response to the organism, the immunodominant antigenic target of that response was sought. *A. baumannii* cell membrane protein preparations from all six strains used to infect mice were separated by two dimensional gel electrophoresis and stained by western blot using paired pre-immune and immune sera from the above infected mice. The two dimensional gels demonstrated effective separation by size and isoelectric focusing (IEF) of membrane proteins from all six clinical isolates (FIG. 2A). In all cases, post-immune serum identified a limited number of unique spots not recognized by pre-immune serum (FIG. 2B).

Figure 3:
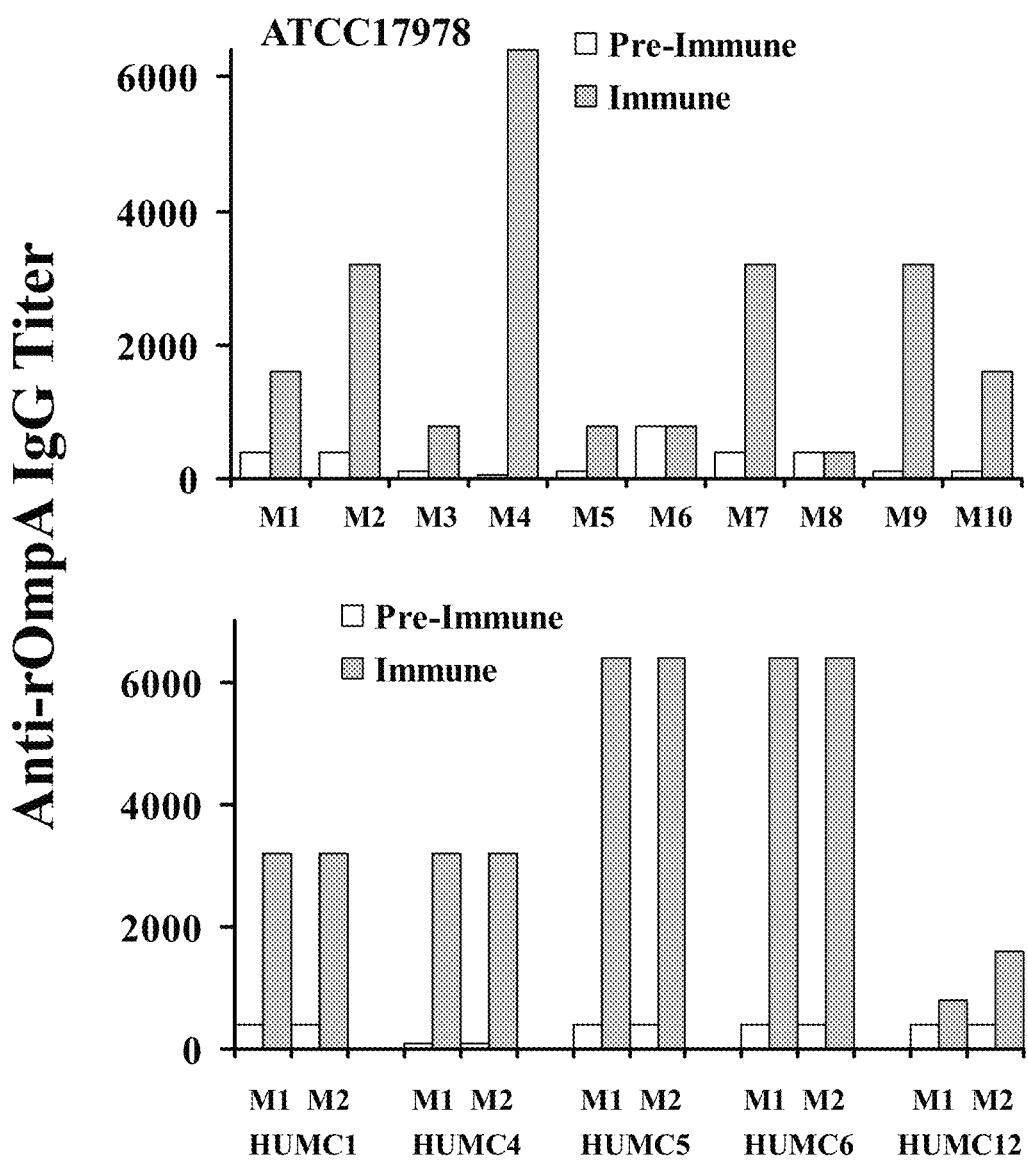
FIG. 3. *A. baumannii* infection induces specific anti-rOmpA antibody response. Ten mice were infected with ATCC 17978 (top) and 2 mice each were infected with clinical isolates from Harbor-UCLA Medical Center (HUMC) (bottom). Paired pre-immune & immune serum IgG anti-rOmpA cell membrane protein titers are shown.

The same three spots (FIG. 2B) were selected for identification by MALDI-TOF analysis across blots from three different *A. baumannii* isolates representing different strain types (Table 2). The protein found in all spots was identified as OmpA, which is known to be a predominant component of the outer cell membrane of *A. baumannii* (Choi et al., Cell Microbiol 10:309-319 (2008). Anti-OmpA antibody titers were determined in paired pre-immune vs. immune sera from mice infected with *A. baumannii*. As for total anti-*A. baumannii* antibodies, anti-rOmpA IgG titers increased in all mice infected with *A. baumannii* (FIG. 3), confirming that OmpA is a target of adaptive humoral immunity post-infection.

EXAMPLE II

OmpA as a Vaccine Antigen

Figure 5:
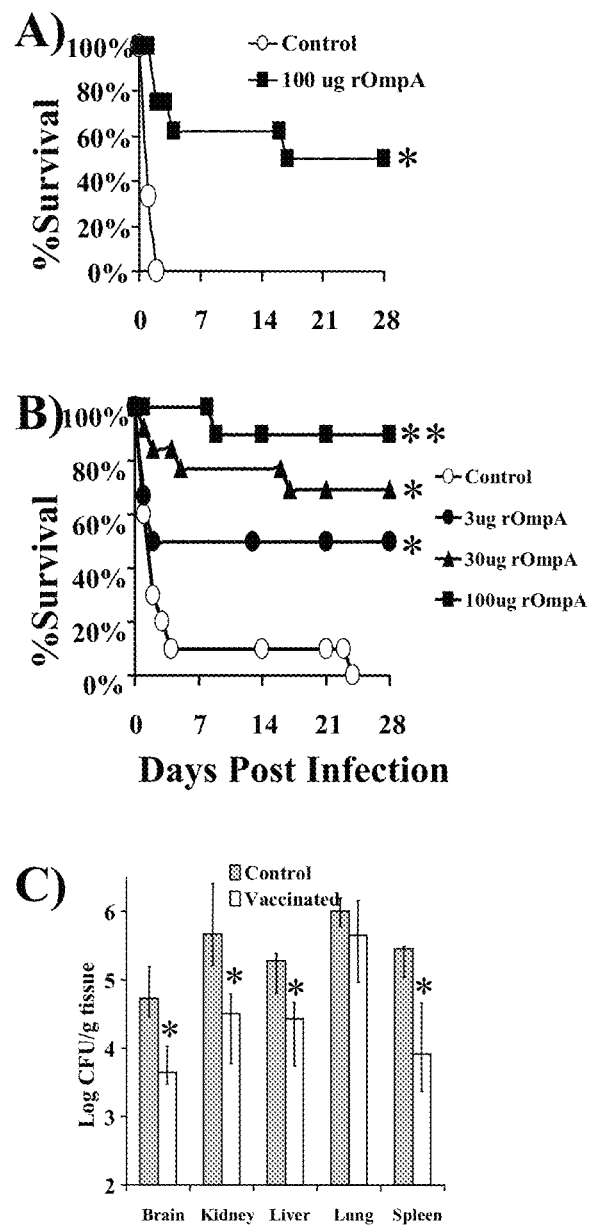
FIG. 5. Vaccination with rOmpA protected mice from lethal *A. baumannii* infection in a disseminated sepsis model. A) Survival of retired breeder (>6 mo) diabetic Balb/c mice vaccinated with 100 μg of rOmpA or aluminum hydroxide (AlOH$_3$) adjuvant alone (n=6 adjuvant control and 8 vaccinated) and infected with $2 \times 10^7$ *A. baumannii* HUMC1. B) Survival of juvenile (8-10 weeks) diabetic Balb/c mice vaccinated with 3, 30, or 100 μg of rOmpA or adjuvant alone (n=10 adjuvant, 12 mice in the 3 μg group, 13 mice in the 30 μg group, and 10 mice in the 100 μg group) and infected with $2 \times 10^7$ *A. baumannii* HUMC1. C) Tissue bacterial burden in diabetic mice (n=10 control and 13 vaccinated) infected with $10^7$ *A. baumannii* HUMC1. *$p<0.05$ vs. adjuvant control; **$p<0.05$ vs. adjuvant control and vs. 3 μg group.

Ideal antigens for vaccine development should be conserved across clinical isolates and should not be homologous to the human proteome. The OmpA gene was sequenced in the six clinical isolates used for infection. The protein sequence had 99% identity across all clinical isolates (FIG. 4), which were harvested 58 years apart (1951 to 2009) from varied clinical sources (cerebrospinal fluid, lung, blood, wound), and included both carbapenem-resistant and a carbapenem-susceptible strain (Table 2 and Table 5). Alignment against 14 other sequences from *A. baumannii* in PubMed revealed 89% identity across all sequences (Table 4). PubMed BLAST search of the human proteome using the ATCC 17978 OmpA sequence revealed only 7 sequences with minimal homology (E values ranging 0.53 to 6.2). Thus OmpA is conserved across a broad array of clinical isolates of *A. baumannii* but shares minimal homology with human proteins.

rOmpA was expressed in *E. coli* and purified by nickel-agarose binding to a His tag. Endoxotin levels were reduced to less than 1 EU per vaccine dose. In the initial experiment, retired breeder (>6 months old) mice were vaccinated and boosted with rOmpA in 0.1% aluminum hydroxide $(Al(OH)_3)$. Two weeks after the boost, the DKA mice were infected via the tail-vein with *A. baumannii* HUMC1. Vaccinated mice had significant improvements in survival compared to adjuvant control mice (FIG. 5A). The experiment was repeated using juvenile mice and with multiple vaccine doses. All vaccine doses improved survival compared to adjuvant control mice, and a dose response was found with 100 µg having the greatest efficacy, which was significantly superior to the 3 µg dose (FIG. 5B).

To determine the impact of vaccination on bacterial burden, juvenile mice were vaccinated, made diabetic, and infected as above. On day 2 post-infection (the day the control mice were predicted to die based on the previous experiment), mice were euthanized and organs harvested to determine tissue bacterial burden. Vaccination reduced by approximately 10-fold the tissue bacterial burden in all organs evaluated except for the lungs, which had a non-significant (p=0.08) 3-fold reduction in bacterial burden (p<0.01 bacterial burden in vaccinated vs. control mice for all other organs) (FIG. 5C).

To confirm efficacy in a second animal model, an established model of *A. baumannii* pneumonia in rats was used (Russo et al., Infect Immun 76:3577-3586 (2008); Russo et al., J Infect Dis 199:513-521 (2009). In brief, Long-Evans rats (250 to 300 g) were anesthetized with 3.5% halothane in 100% oxygen until unconscious and then maintained at 3.5% halothane. The trachea was exposed surgically, and a 4-in. piece of 1-0 silk was slipped under the trachea to facilitate instillation of the inoculum. The animals were suspended in a supine position on a 60°-incline board. Pulmonary instillation of bacteria in PBS was introduced intratracheally (1.2 ml/kg of body weight) via a 1-ml syringe and 26-gauge needle, and the incision was closed with surgical staples. Lungs were harvested at 24 and 48 hours, homogenized, and quantitatively cultured to determine bacterial burden. This model recapitulates aspiration via the upper airways, which is a common mode of *A. baumannii* clinical pneumonia in intensive care units, without requiring immune suppression (Russo et al., Infect Immun 76:3577-3586 (2008). Rats were vaccinated, boosted, and infected intratracheally two weeks after the boost. Lung bacterial burden was assessed at 24 and 48 hours. (FIG. 5D).

EXAMPLE III

Antibodies in Vaccine-Mediated Protection

Figure 6:
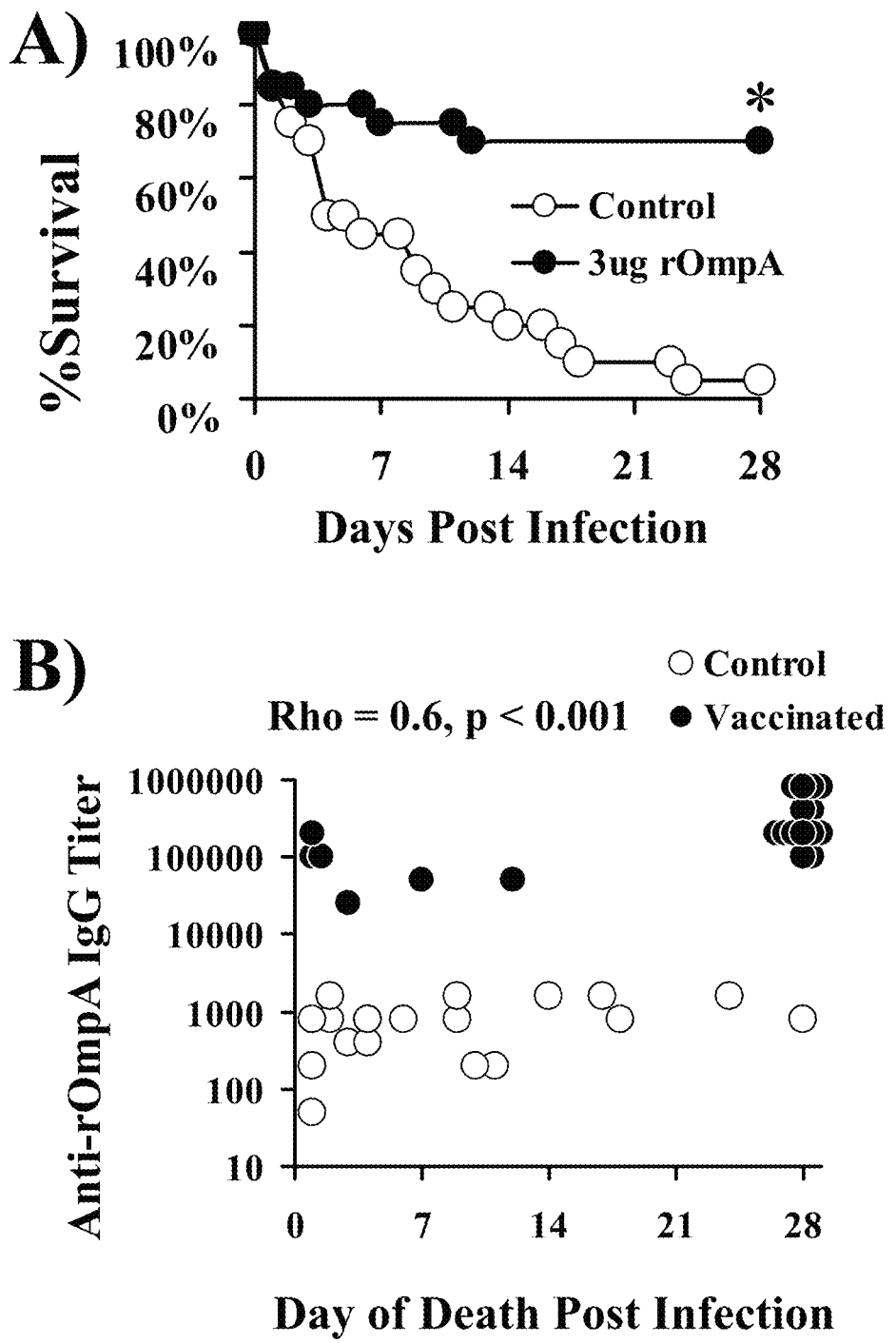
FIG. 6. Anti-rOmpA antibody titers correlated with survival in infected mice. A) Survival of juvenile diabetic Balb/c mice vaccinated with 3 μg of rOmpA or adjuvant alone (n=20 mice per group from 2 experiments) and infected with 1.4 or $1.6 \times 10^7$ *A. baumannii* HUMC1 in the sequential experiments. The experiments were terminated at 28 days with all remaining mice appearing clinically well. B) Antibody titers of individual vaccinated and control mice vs. day of death).

The relationship between antibody titers and survival in vaccinated mice was evaluated. Given the approximate 50% survival seen in mice vaccinated with 3 µg, this dose was chosen for antibody-survival analysis, to enable a mixture of vaccinated mice that survived or did not survive the infection. In two separate experiments, mice were vaccinated with 3 µg or adjuvant alone, boosted, and antibody titers determined pre-infection. Vaccination induced marked increases in anti-rOmpA IgG antibody titers (median [range] titers=204,800 [102,400-409,600] vs. 800 [400-1,000] for vaccinated vs. control mice, p<0.0001). Because the infectious inocula were somewhat lower in these experiments ($1.4\times10^7$ and $1.6\times10^7$) than in the previous ($2\times10^7$), more than 50% of vaccinated mice survived despite the use of the 3 µg vaccine dose (FIG. 6A). Antibody titers correlated with survival when analyzing both vaccinated and control mice combined (p<0.0001, rho=0.6) or just analyzing vaccinated mice without control mice (p=0.0009, rho=0.6 by Spearman Rank test, FIG. 6B). An IgG titer threshold of ≥204,800 was maximally accurate (98%) at distinguishing survivors from non-survivors when analyzing both vaccinated and control mice, whereas titers of either 102,400 or 204,800 both had the same maximal accuracy (85%) when just analyzing vaccinated mice (Table 3).

The correlation of antibody titer with survival suggested that antibodies were rOmpA vaccine effectors. B cell deficient mice were infected with *A. baumannii* HUMC1 to determine if mice deficient in these cell types were susceptible to infection, but no deaths occurred and the mice never appeared clinically ill. Furthermore, B cell deficient mice were resistant to diabetes induction, making comparisons problematic between B cell deficient and wild type mice. Therefore, rather than disrupting B lymphocyte function, donor mice were vaccinated with rOmpA or adjuvant alone and immune or control serum harvested by terminal bleed. rOmpA titers in immune serum were higher than in control serum (1:409,600 vs. 1:3200). DKA mice were treated ip with 0.5 ml of immune or control serum and infected 2 hours later with *A. baumannii*

Figure 7:
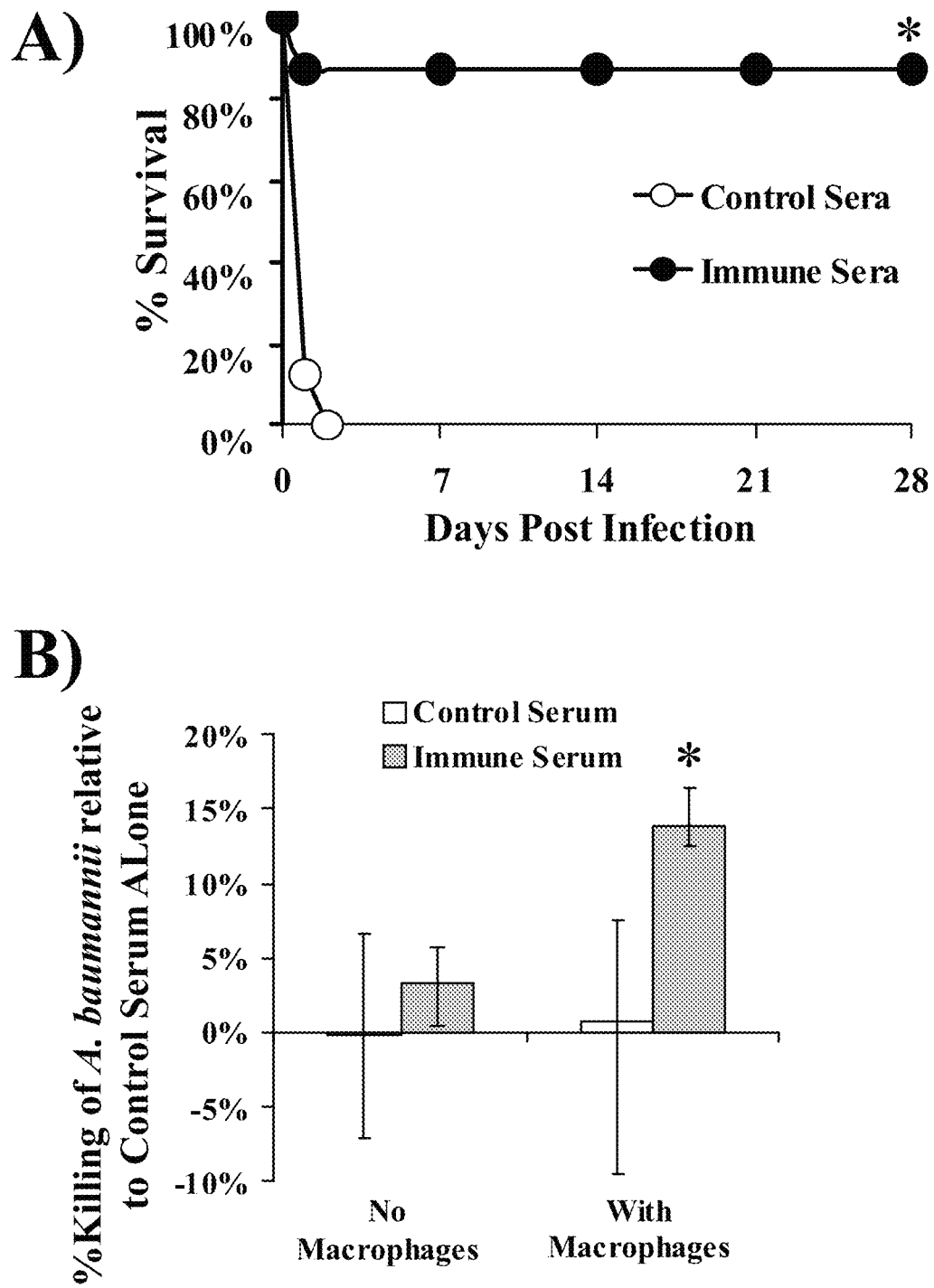
FIG. 7. Passive immunization with rOmpA immune serum protected recipient mice from lethal infection. Survival of mice (n=10 per group) treated ip with immune (from OmpA vaccinated) or adjuvant control serum before tail-vein infection with *A. baumannii* HUMC1. *$p=<0.0001$ vs. non-immune serum. B) Opsonophagocytic killing of *A. baumannii* HUMC1 during incubation of macrophages with immune (from OmpA vaccinated mice) or non-immune (from adjuvant treated mice) serum. *$p<$***vs. control.

HUMC 1. Mice treated with immune serum had markedly enhanced survival vs. mice treated with control serum (FIG. 7A).

To define the mechanism of antibody-induced protection, *A. baumannii* was cultured in the presence of immune vs. non-immune serum. *A. baumannii* numbers increased after 1 hour culture in both sera, excluding complement-mediated killing as a mechanism of protection. However, immune serum did enhance macrophage opsonophagocytic killing of *A. baumannii* (FIG. 7B).

TABLE 2

Bacterial Strains*

| Strain | Strain Type | Source | Carbapenem Resistant? | Comments |
|---|---|---|---|---|
| ATCC 17978 | ST112 | ATCC; cerebrospinal fluid isolate | No | Isolated in 1951 from a 4 month old with fatal meningitis (Piechaud and Second, 1951) |
| HUMC1 | ST206 | HUMC, blood and sputum isolate | Yes | Bacteremic VAP |
| HUMC4 | ST208 | HUMC, deep endotracheal aspirate | Yes | VAP |
| HUMC5 | ST208 | HUMC, bronchoalveolar lavage | Yes | VAP |
| HUMC6 | ST208 | HUMC, sputum | Yes | VAP |
| HUMC12 | ST208 | HUMC, wound infection | Yes | Infected diabetic stump wound |

*HUMC = clinical isolates from in-patients in 2009; VAP = ventilator associated pneumonia. Susceptibility results shown in Table 5.

TABLE 3

Accuracy of anti-rOmpA IgG Antibody Titer Cut Offs for Predicting Survival in Vaccinated and Control Mice Infected with *A. baumannii* HUMC1

| | Sensitivity* | Specificity* | PPV* | NPV* | Accuracy* |
|---|---|---|---|---|---|
| | | | IgG Titers | | |
| ≥25,600 | 100% (100%) | 76% (0%) | 71% (70%) | 100% (N/A)† | 85% (70%) |
| ≥51,200 | 100% (100%) | 80% (17%) | 75% (74%) | 100% (100%) | 88% (75%) |
| ≥102,400 | 100% (100%) | 88% (50%) | 83% (82%) | 100% (100%) | 93% (85%) |
| ≥204,800 | 43% (86%) | 96% (83%) | 86% (92%) | 76% (71%) | 98% (85%) |
| ≥409,600 | 43% (43%) | 96% (100%) | 86% (100%) | 76% (43%) | 78% (60%) |

Numbers shown are for all 40 vaccinated and control mice, or for just the 20 vaccinated mice (in parenthesis).

*Sensitivity = number of surviving mice with titers ≥ the cut-off/number of all surviving mice; Specificity = number of mice that died with titers < the cut-off/number of all mice that died; PPV = positive predictive value, which is the percentage of mice with titers ≥ the cut-off that survived; NPV = negative predictive value, which is the percentage of mice with titers < cut-off that died; Accuracy = [(number of mice with titers ≥ the cut-off that survived infection) + (number of mice with titers < the cut-off that died from infection)/(all mice)].

†No vaccinated mice had titers <25,600, so NPV cannot be calculated.

TABLE 4

```
Alignment of SEQ ID NOS 14-28, respectively, in order of appearance.

10         20         30         40         50         60
                 ....|....|....|....|....|....|....|....|....|....|....|....|
gi|148839593     MKLSRIALATMLVAAPLAAANAGVTVTPLLLGYTFQDSQHNNGGKDGNLTNGPELQDDLF
gi|260557183     ............................................................
gi|184159409     .......................................................S....
gi|163866826     .......................................................S....
gi|129307154     .......................................................S....
gi|163866824     .......................................................S....
gi|163866832     ............................................................
gi|169632496     .......................................................S....
gi|213057017     ...............................T.........E................
gi|169794817     .................................T.........E................
gi|163866830     ...G.............................T.........E................
gi|129307156     .................................T.........E................
gi|21666310      .................................T.........E................
gi|163866828     .................................T.........E................
gi|239501745     ............................................E...H----K..DS........
```

TABLE 4-continued

Alignment of SEQ ID NOS 14-28, respectively, in order of appearance.

```
                       70         80         90        100        110        120
                ....|....|....|....|....|....|....|....|....|....|....|....|
gi|148839593    VGAALGIELTPWLGFEAEYNQVKGDVDGASAGAEYKQKQINGNFYVTSDLITKNYDSKIK
gi|260557183    ............................................................
gi|184159409    ............................................................
gi|163866826    ............................................................
gi|129307154    ............................................................
gi|163866824    ............................................................
gi|163866832    ..........................PV................................
gi|169632496    ............................................................
gi|213057017    ..........................LA................................
gi|169794817    ..........................LA................................
gi|163866830    ..........................LA................................
gi|129307156    ..........................LA................................
gi|21666310     ..........................LA................................
gi|163866828    ..........................LA................................
gi|239501745    ........................--TNYG...............................

130        140        150        160        170        180
                ....|....|....|....|....|....|....|....|....|....|....|....|
gi|148839593    PYVLLGAGHYKYDFDGV--NRGTRGTSEEGTLGNAGVGAFWRLNDALSRTEARATYNAD
gi|260557183    ................--..........................................
gi|184159409    ................--..........................................
gi|163866826    ................--..........................................
gi|129307154    ................--..........................................
gi|163866824    ................--..........................................
gi|163866832    ................--......N....................................
gi|169632496    ................--......N....................................
gi|213057017    ............EIPDL--SYH---ND......................G...F.
gi|169794817    ............EIPDL--SYH---ND......................G...F.
gi|163866830    ............EIPDL--SYH---ND......................G...F.
gi|129307156    ............EIPDL--SYH---ND......................G...F.
gi|21666310     ............EIPDL--SYH---ND......................GNLYF.
gi|163866828    ............EIPDL--SYH---ND......................G...F.
gi|239501745    ............DARLAYH---DG.........................G...F.

190        200        210        220        230        240
                ....|....|....|....|....|....|....|....|....|....|....|....|
gi|148839593    EEFWNYTALAGLNVVLGGHLKPAAP-VVEVAPVEPTPVTPQPQELTEDLNMELRVFFDTN
gi|260557183    .........................-.......A...........................
gi|184159409    .........................-.......A...........................
gi|163866826    .........................-.......A...........................
gi|129307154    .........................-.......A...........................
gi|163866824    .........................-.......A...........................
gi|163866832    .........................-.......A...........................
gi|169632496    ...................V.....-.......A...........................
gi|213057017    .K.......................-.......A...........................
gi|169794817    .K.......................-.......A...........................
gi|163866830    .K.......................-.......A...........................
gi|129307156    .K.......................-.......A...........................
gi|21666310     .K.......................-.......A...........................
gi|163866828    .K.......................-.......A...........................
gi|239501745    .K.......................-.......A...........................

250        260        270        280        290        300
                ....|....|....|....|....|....|....|....|....|....|....|....|
gi|148839593    KSNIKDQYKPEIAKVAEKLSEYPNATARIEGHTDNTGPRKLNERLSLARANSVKSALVNE
gi|260557183    ............................................................
gi|184159409    ............................................................
gi|163866826    ............................................................
gi|129307154    ............................................................
gi|163866824    ............................................................
gi|163866832    ............................................................
gi|169632496    ............................................................
gi|213057017    ............................................................
gi|169794817    ............................................................
gi|163866830    ............................................................
gi|129307156    ............................................................
gi|21666310     ............................................................
gi|163866828    ............................................................
gi|239501745    ............................................................
```

TABLE 4-continued

Alignment of SEQ ID NOS 14-28, respectively, in order of appearance.

```
                       310        320        330        340        350
              ....|....|....|....|....|....|....|....|....|....|....|....|
gi|148839593  YNVDASRLSTQGFAWDQPIADNKTKEGRAMNRRVFATITGSRTVVVQPGQEAAAPAAAQ
gi|260557183  ............................................................
gi|184159409  ............................................................
gi|163866826  ..........................................LA------------
gi|129307154  ................................................----------------
gi|163866824  ..............................................P....--------------------
gi|163866832  ................................................--------------------
gi|169632496  ............................................................
gi|213057017  ..........................................GQEA..PA..Q
gi|169794817  ..........................................GQEA..PA..Q
gi|163866830  ..........................................LAE-----------
gi|129307156  ................................................----------------
gi|21666310   ..........................................LAEQPVAQ------
gi|163866828  ................................................--------------------
gi|239501745  ............................................................
``` gi|148839593: ATCC 17978, gi|260557183: ATCC 19606, gi|184159409: ACICU, gi|163866826: DM511 (PMID 18591275), gi|129307154: 16B, gi|163866824: IF501 (PMID 18591275) gi|163866832: LI311 (PMID 18591275), gi|169632496: SDF, gi|213057017: AB0057, gi|169794817: AYE, gi|163866830: BD335 (PMID 18591275), gi|129307156:, gi|21666310:, gi|163866828: KB167 (PMID 18591275), gi|239501745: AB900

TABLE 5

Antibacterial Minimum Inhibitory Concentrations (μg/ml) for Clinical Isolates Used in the Current Study.

| Strain | Amikacin | Gentamicin | Aztreonam | Ampicillin/ sulbactam | Pipercillin/ tazobactam | Cefepime | Meropenem |
|---|---|---|---|---|---|---|---|
| ATCC 17978 | 8 | 8 | 16 | 1/0.5 | 0.06/4 | 2 | 0.25 |
| HUMC1 | >128 | >128 | 64 | 16/8 | <128/4 | 16 | 32 |
| HUMC4 | >128 | >128 | 32 | 32/16 | <128/4 | 16 | 8 |
| HUMC5 | >128 | >128 | 32 | 32/16 | <128/4 | 16 | 8 |
| HUMC6 | >128 | >128 | 32 | 32/16 | <128/4 | 16 | 8 |
| HUMC12 | >128 | >128 | 32 | 32/16 | <128/4 | 16 | 4 |

| Strain | Imipenem | Ertapenem | Doripenem | Ciprofloxacin | Tigecycline | Colistin |
|---|---|---|---|---|---|---|
| ATCC 17978 | 0.25 | 4 | 0.5 | 0.125 | 0.25 | 2 |
| HUMC1 | 16 | 128 | 16 | >128 | 4 | 2 |
| HUMC4 | 4 | 32 | 4 | 64 | 4 | 2 |
| HUMC5 | 4 | 32 | 8 | 64 | 4 | 2 |
| HUMC6 | 4 | 32 | 4 | 64 | 4 | 2 |
| HUMC12 | 2 | 16 | 8 | 64 | 4 | 2 |

EXAMPLE IV

The Impact of Vaccine Dose on Immunogenicity

Figure 8:
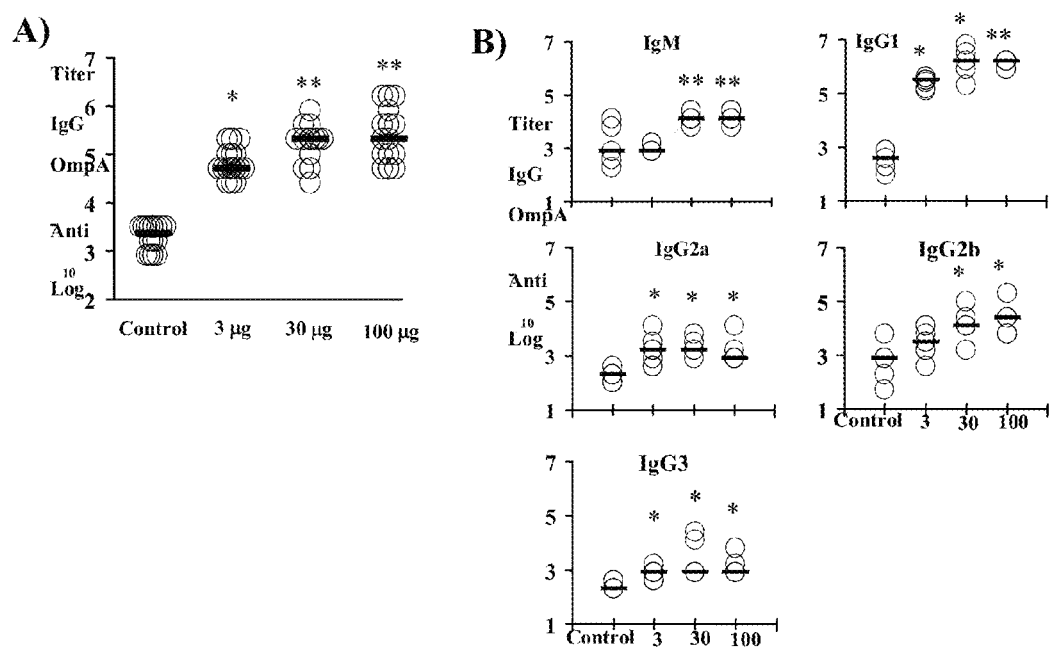
FIG. 8. Antibody titers induced by various doses of rOmpA or adjuvant alone. A) Balb/c mice (n=11 per group from 3 separate experiments) were vaccinated with one of 3 doses of vaccine or adjuvant alone. IgG titers from individual mice and the median titers (horizontal bars) for each group are shown. B) IgM and IgG subtype titers measured by ELISA from vaccinated or control mice. *$p<0.05$ vs. adjuvant alone; **$p<0.05$ vs. adjuvant alone and vs. 3 μg dose.

The impact of vaccine dose on the nature of the immune response to the rOmpA vaccine was explored. Mice were vaccinated as above. Two weeks after the boost, serum and splenocytes were harvested. Median [interquartile ranges] antibody titers for control, 3, 30, and 100 μg dose vaccinated mice were 2,400 [800-3,200], 51,200 [51,200-102,400], 204,800 [102,400-204,800], and 204,800 [89,600-512,000] ($p<0.001$ for all vaccinated doses vs. control and $<0.05$ for both 30 and 100 μg dose vs. 3 μg dose) (FIG. 8A).

IgM responses were substantially higher in response to the 30 and 100 μg doses than the 3 μg dose (median titer 1:12,000 for both higher doses vs. 1:800 for the 3 μg dose and adjuvant control mice, $p<0.05$) (FIG. 6B). IgG1 was the predominant Ig subtype found, with median titers of 1:320,000 to 1:1,600,000 for vaccinated mice vs. 1:400 for control mice ($p<0.05$ for all vs. control). IgG1 titers were significantly higher for mice vaccinated with 100 μg than 3 μg ($p=0.02$). Median IgG2a and 2b titers were substantially lower than IgG1 titers but still significantly above the titers in control mice (FIG. 8B). IgG3 titers were much lower, with median titers of 1:800 for all three vaccinated groups, but still significantly higher than control mice (median 1:200).

Figure 9:
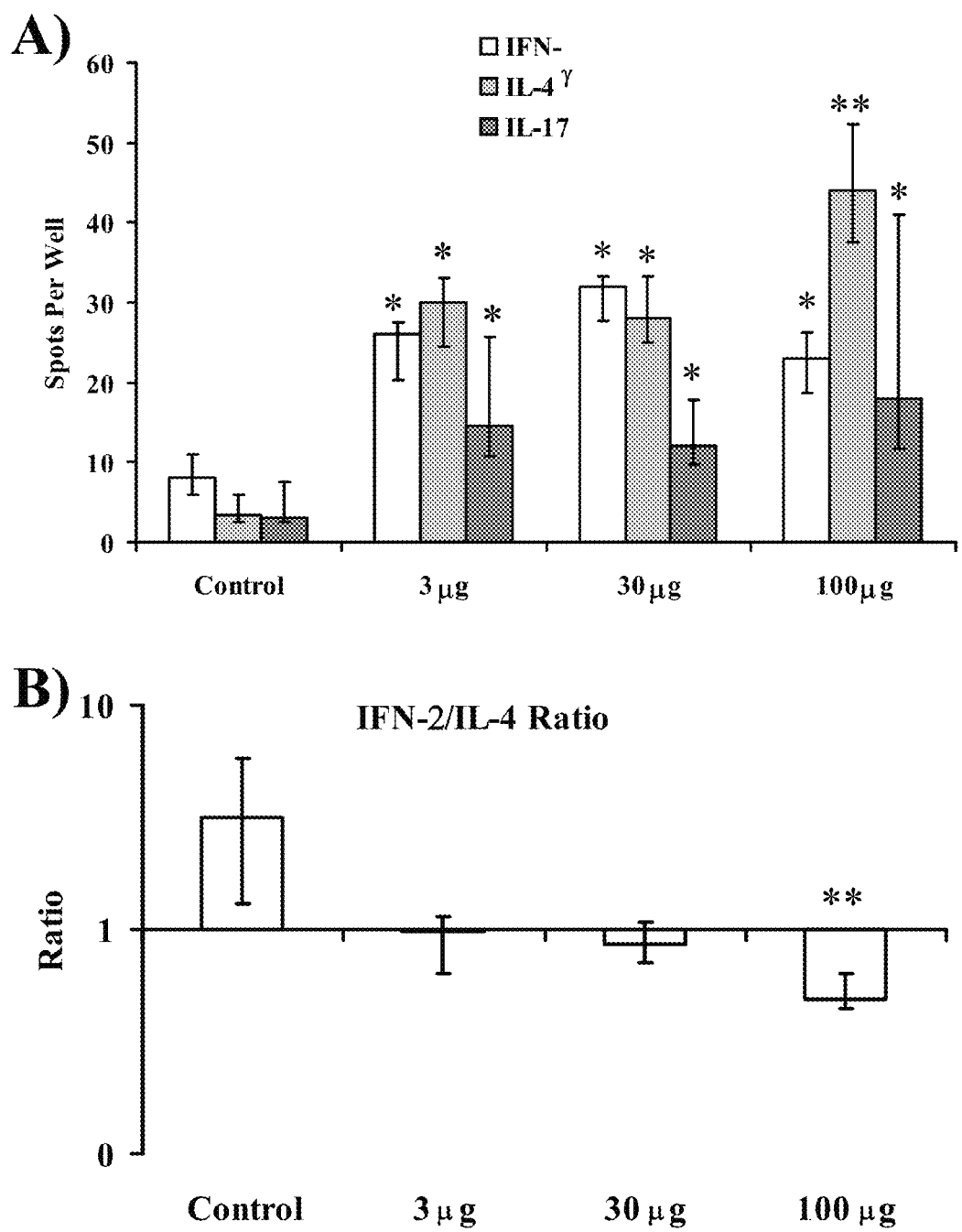
FIG. 9. Splenocyte cytokine production stimulated by rOmpA. A) IFN-γ, IL-4, or IL-17A production by splenocytes from vaccinated or control mice (n=8 per group from 2 experiments) stimulated for 48 h with rOmpA measured by ELISpot. B) Ratio of IFN-γ:IL-4 produced by splenocytes from individual mice. Median and interquartile ranges are shown. *$p<0.05$ vs. adjuvant control. **$p<0.05$ vs. 3 and 30 μg dose, and vs. adjuvant control.

Similarly to antibody responses, all doses of vaccine mediated significant increases in IFNγ, IL-4, and IL-17 production by splenocytes, versus splenocytes from control mice (FIG. 9A). IL-4 production was maximal at the highest (100 μg) dose of vaccine. Compared to the baseline IFNγ-predominant IFNγ:IL-4 ratio after stimulation with control (unvaccinated) splenocytes by rOmpA, all doses of vaccines mediated more balanced ratios (median [interquartile] ratios=3.2 [1.3-5.8] for control vs. 1.0 [0.8-1.3], 0.9 [0.7-1.1], and 0.5 [0.5-0.7] for control vs. 3, 30, and 100 μg doses, respectively). The Th1:Th2 ratio was significantly lower for the 100 μg dose than for all other groups ($p<0.02$ for all comparisons).

Figure 10:
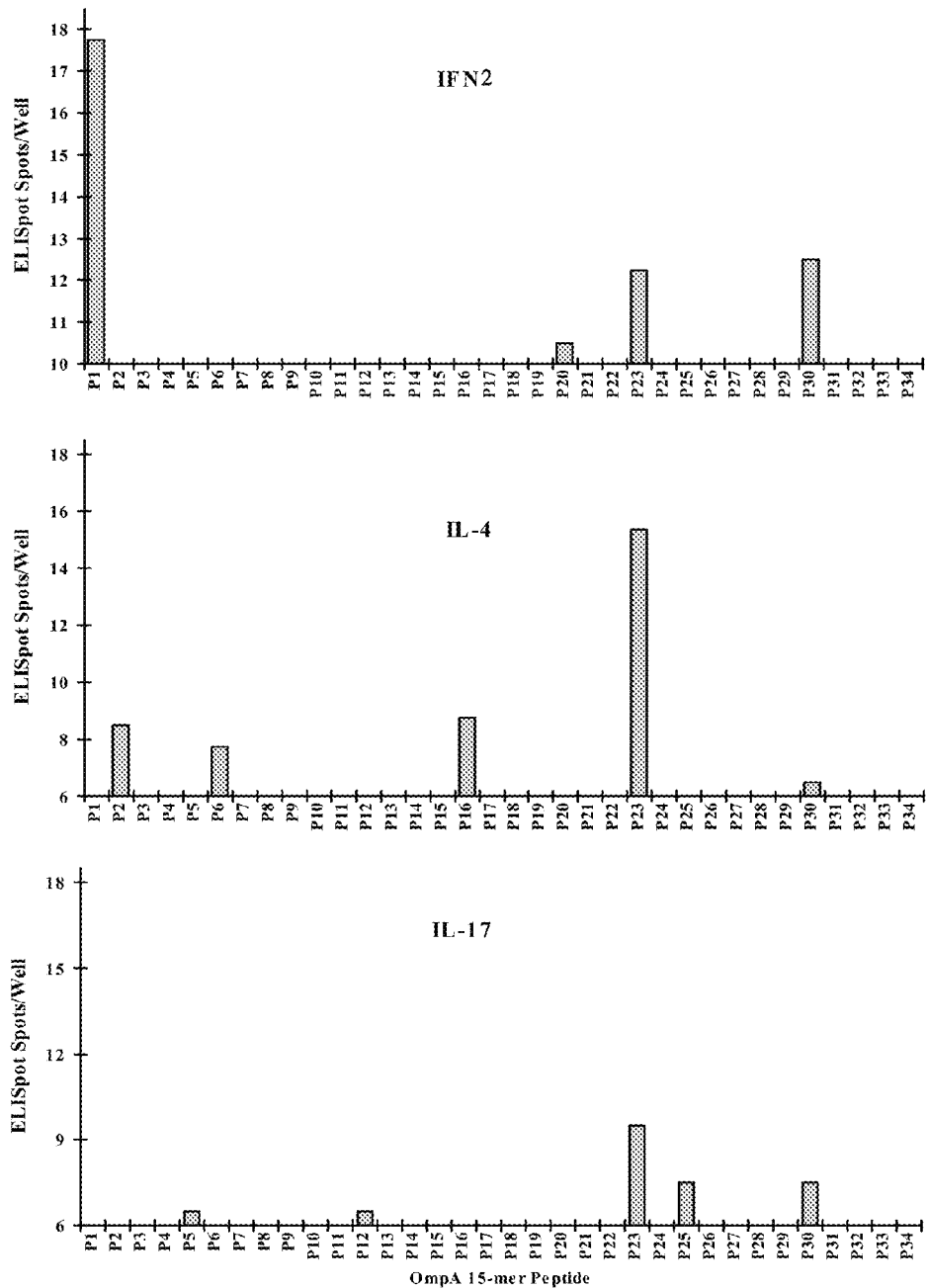
FIG. 10. T cell epitopes stimulate distinct cytokine profiles. Splenocytes were harvested from vaccinated Balb/c mice and stimulated with 5 μg/ml of individual, overlapping 15mer peptides for 48 hours in ELISpot plates. Graphed are the means of 2 mice per group each run in duplicate. The lower bound of the Y axis is set at the third quartile of responses across all peptides.

T cell and B cell immunodominant epitopes were defined using overlapping peptides. Immunodominant T cell epitopes were defined as those inducing cytokine responses above the 3rd quartile across all 15mers tested. In mice vaccinated with 3 μg, only 4, 5, and 5 peptides were found to meet this criteria for IFN-γ, IL-4, and IL-17, respectively (FIG. 10). Distinct peptides were found to induce the three cytokines from splenocytes. Of interest was that peptide 1 was by the far most potent inducer of IFN-γ production and peptide 2, which overlapped with peptide 1 by 5 amino acids, induced substantially more IL-4. Only 2 consensus epitopes were found to induce all three cytokines from splenocytes harvested from mice vaccinated with 3 µg (peptides 23 and 30).

EXAMPLE V

Epitope Mapping of Anti-OmpA Polyclonal Immune Serum

Figure 11:
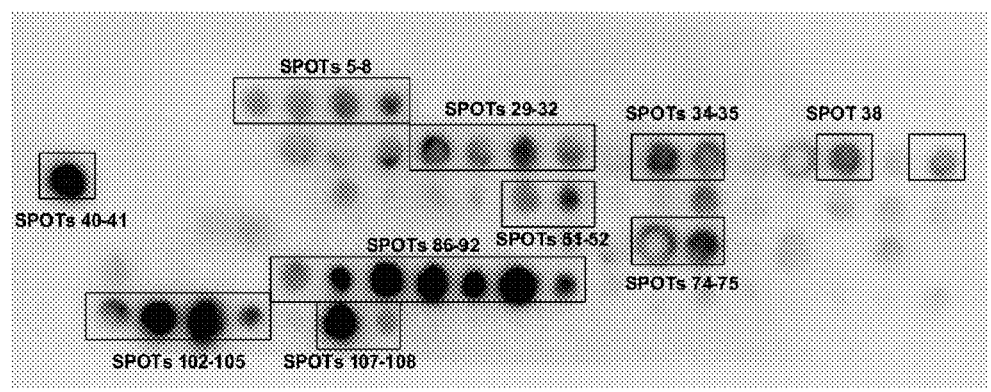
FIG. 11. Peptide epitope mapping of OmpA using polyclonal immune serum from OmpA-vaccinated mice. Each spot contains a peptide recognized by immune serum. The immunogenic epitopes shown are: 1. SPOTs 86-92, amino acids 265PRKLNERLSLARANSV280 (SEQ ID NO:7); 2. SPOTs 102-105, amino acids 307ADNKTKEGRAMNR319 (SEQ ID NO:8); 3. SPOTs 107-108, amino acids 319RRV-FATITGSRTV331 (SEQ ID NO:9); 4. SPOTs 40-41, amino acids 121KYDFDGVNRGTRG133 (SEQ ID NO:10).
Figure 12:
FIG. 12. In silico model of OmpA protein. The model was built using the Swiss-Model automated protein structure homology-modeling server accessible via the ExPASy web server, or from the program DeepView (Swiss Pdb-Viewer). Major immunogenic epitopes are color-coded (see adjacent text).

To identify B cell epitopes, immuno dot blots were conducted using immune serum and membranes containing overlapping peptides. In brief, overlapping 12-mer peptides, offset by five amino acids were synthesized, covalently bound at the C terminus to a Whatman 50 cellulose membrane, and directly probed with the immune serum. The membranes were counter-stained with secondary anti-mouse IgG antibody, washed four times in T-TBS (TBS containing 0.05% Tween 20), and incubated with a 1:3,000 dilution of horseradish peroxidase-conjugated Protein G (Bio-Rad, Hercules, Calif.) in blocking buffer. The membranes were processed for film development (chemiluminescent detection) with an Amersham Pharmacia Biotech ECL kit (Piscataway, N.J.). TIF images were generated with the Bio-Rad Gel Doc 2000 Imaging System and densitometry used to define quantitative reactivity. A number of specific B cell epitopes were identified (FIG. 11). Only 3 peptides were found to represent both B cell and T cell epitopes (2, 16, and 23). Homology modeling revealed that the predominant B cell epitopes were localized to surface exposed a helices and β sheets, although surprisingly there was also a dominant B cell epitope on the cytoplasmic face of the protein at a hairpin loop structure (FIG. 12).

rOmpA was modeled in silica by the SWISS-MODEL fully automated protein structure homology-modeling server accessible via the ExPASy web server. The model was optimized by energy minimization using Discovery Studio version 2.1 (Accelrys, San Diego, Calif.). The minimization was performed in several steps, using a steepest descendent and conjugate gradient algorithm to reach the minimum convergence (0.02 kcal mol-1 A-1). The epitope corresponding residues are color-coded (FIG. 11): Major Immunogenic Epitopes (SEQ ID NOS 7-10, respectively, in order of appearance):

```
1. SPOTs 86-92
aa 265PRKLNERLSLARANSV280-green

2. SPOTs 102-105
aa 307ADNKTKEGRAMNR319-dark blue

3. SPOTs 107-108
aa 319RRVFATITGSRTV331-yellow

4. SPOTs 40-41
aa 121KYDFDGVNRGTRG133-violet
(bottom right)
```

EXAMPLE VI

Comparison of the ORF Sequence, Epitope Sequences, and Immunogenicity of Previously Reported Sequences with the Vaccine Sequences Provided by the Invention a. Alignment of the Prior Art Sequence with 6 Clinical Isolates Harvested Between 1951 (ATCC17978) and 2009 (HUMC Strains)

The prior art sequence differs by 53/350 amino acids plus has an additional 28 amino acids at the beginning of the sequence which does not appear in any *A. baumannii* OmpA sequence. In total, therefore, the prior art sequence differs by 81 amino acids (23% sequence divergence) vs. all 6 clinical isolates of *A. baumannii* used to infect mice. Finally, when compared to the sequences of 12 other *A. baumannii* isolates in PubMed Genbank, the prior art sequence remains divergent (compare prior art sequence to the 12 aligned sequences in Table 4).

b. Sequences of Known B and T Cell Epitopes Vs. *A. baumannii* OmpA Sequences from ATCC 17978 and HUMC Strains Used to Infect Mice.

Comparing the amino acid sequences of the T and B cell epitopes identified as immunodominant in the OmpA vaccine reveals that virtually every immunodominant epitope has a different sequence than is present in the prior art. Thus, the mutations that are distinct between previously known sequences and the sequences of the present invention are specifically present in the immune-reactive T and B cell epitopes (FIG. 13).

c. Immunological Differences.

Figure 14:
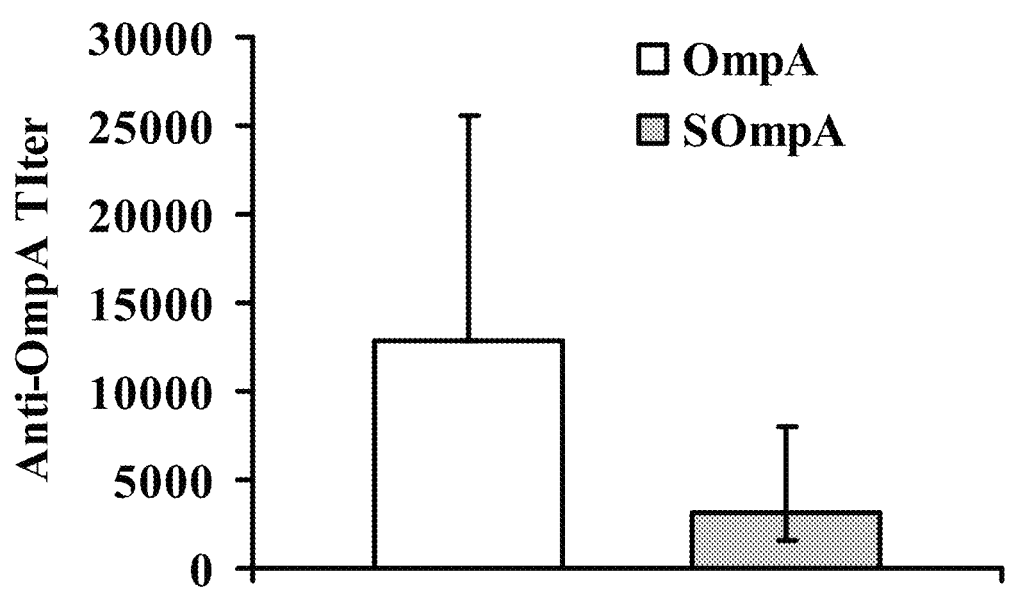
FIG. 14. Immune serum from mice infected with *A. baumannii* generate significantly higher antibody titers to our patented OmpA sequence than to protein made from a synthetic gene (SOmpA) based on the prior art sequence. Anti-OmpA ELISA was used to determine titers in immune serum directed against protein made with our sequence (OmpA) vs. the prior art sequence (SOmpA). P value for the difference=0.002.

To determine if the sequence difference between previously known sequences and the OmpA sequences of the invention result in immunological differences, we infected 10 mice with sublethal inocula of *A. baumannii* ATCC17978. Two weeks after infection, we harvested immune sera. ELISA plates were coated with OmpA that was either produced from a synthetic gene encoding a previously known sequence or produced from the OmpA sequence of the invention. The antibody titers of serum from infected/immune mice were compared when the ELISA was run against the claimed OmpA sequence versus the previously known sequence. Immune serum had significantly higher titers against the OmpA than the Patented OmpA (synthetic OmpA, or SOmpA, see FIG. 14). Median [IQ range] titers were 12,800 [12,800-25,600] vs. 3,300 [1,600-8,000], p=0.002.

EXAMPLE VII

Figure 15:
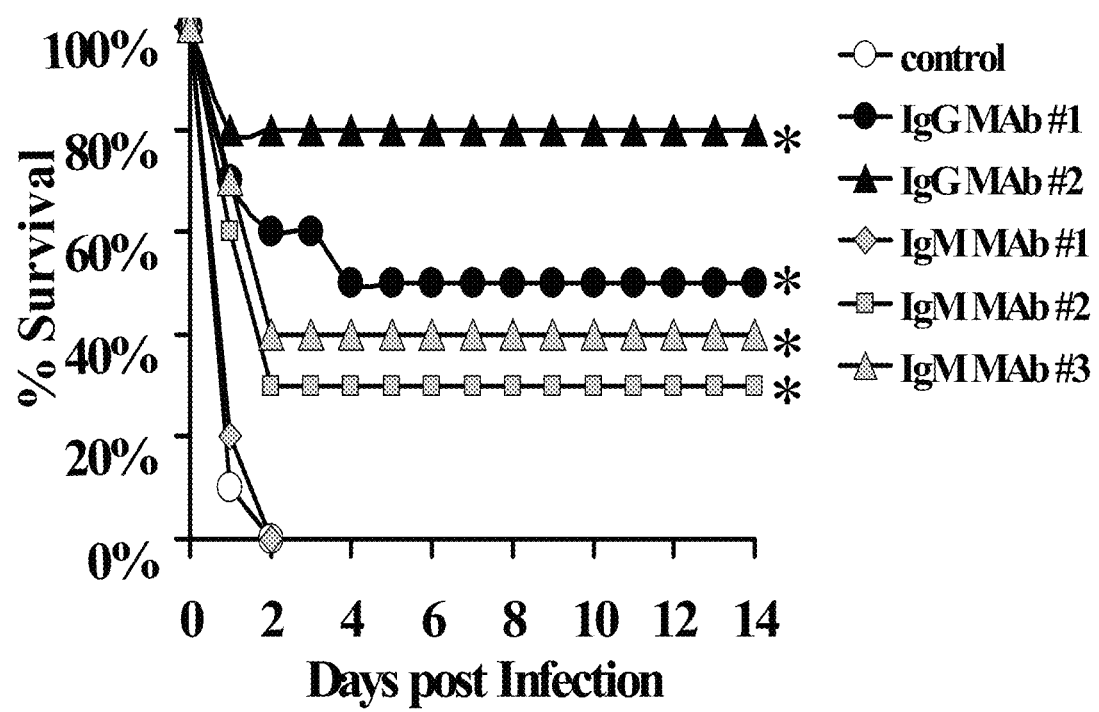
FIG. 15. Anti-OmpA MAb treats lethal *A. baumannii* infection. Mice (n=10 per group from 2 experiments) were infected iv via the tail vein and treated ip with 50 μg of MAb or isotype control antibody per mouse. *$p<0.05$ vs. control.

Monoclonal Antibodies (MAbs) Against OmpA Effectively Treat Lethal *A. baumannii* Bloodstream Infection Multiple MAbs were raised against OmpA and pre-clones selected for subcloning by identifying those pre-clones that could bind to native OmpA on the *A. baumannii* surface. After selection by ELISA and flow cytometry for cell surface staining, five hybridoma subclones, 3 IgMs and 2 IgGs, were obtained. Hybridoma supernatants were dialyzed against PBS. Negative control was an IgG isotype control MAb. C3H/FeJ mice were infected via the tail-vein with *A. baumannii* HUMC1 were treated IP with 50 µg of MAb several hours after infection. 4 of the MAbs substantially improved survival of infected mice, whereas 1 MAb was of no benefit (IgM #1) (FIG. 15). These data confirm that MAb therapy is effective against these infections, validating the concept of passive vaccination against *A. baumannii*, and the composition of matter of the MAbs in hand.

REFERENCES

Bad Bugs, No Drugs. In A White Paper from the Infectious Diseases Society of America (IDSA), Alexandria, Va. 2009. The bacterial challenge: time to react. A call to narrow the gap between multidrug-resistant bacteria in the EU and the development of new antibacterial agents. In European Center for Disease Prevention (ECDC) and European Medicines Agency (EMEA).

Adams, M. D., G. C. Nickel, S. Bajaksouzian, H. Lavender, A. R. Murthy, M. R. Jacobs, and R. A. Bonomo. 2009. Resistance to colistin in *Acinetobacter baumannii* associated with mutations in the PmrAB two-component system. *Antimicrob Agents Chemother* 53:3628-3634.

Alsultan, A. A., A. Hamouda, B. A. Evans, and S. G. Amyes. 2009. *Acinetobacter baumannii*: emergence of four strains with novel bla(OXA-51-like) genes in patients with diabetes mellitus. *J Chemother* 21:290-295.

Bartual, S. G., H. Seifert, C. Hippler, M. A. Luzon, H. Wisplinghoff, and F. Rodriguez-Valera. 2005. Development of a multilocus sequence typing scheme for characterization of clinical isolates of *Acinetobacter baumannii*. *J Clin Microbiol* 43:4382-4390.

Beavers, S. F., D. B. Blossom, T. L. Wiemken, K. Y. Kawaoka, A. Wong, L. Goss, M. I. McCormick, D. Thoroughman, and A. Srinivasan. 2009. Comparison of risk factors for recovery of *Acinetobacter baumannii* during outbreaks at two Kentucky hospitals, 2006. *Public Health Rep* 124:868-874.

Boucher, H. W., G. H. Talbot, J. S. Bradley, J. E. Edwards, D. Gilbert, L. B. Rice, M. Scheld, B. Spellberg, and J. Bartlett. 2009. Bad bugs, no drugs: no ESKAPE! An update from the Infectious Diseases Society of America. *Clin Infect Dis* 48:1-12.

Caricato, A., L. Montini, G. Bello, V. Michetti, R. Maviglia, M. G. Bocci, G. Mercurio, S. M. Maggiore, and M. Antonelli. 2009. Risk factors and outcome of *Acinetobacter baumanii* infection in severe trauma patients. *Intensive Care Med* 35:1964-1969.

Choffnes, E. R., D. A. Relman, and A. Mack. 2010. for the Forum on Microbial Threats, Institute of Medicine of the National Academies. Antibiotic resistance: implications for global health and novel intervention strategies. The National Academies Press, Washington D.C.

Choi, C. H., S. H. Hyun, J. Y. Lee, J. S. Lee, Y. S. Lee, S. A. Kim, J. P. Chae, S. M. Yoo, and J. C. Lee. 2008. *Acinetobacter baumannii* outer membrane protein A targets the nucleus and induces cytotoxicity. *Cell Microbiol* 10:309-319.

D'Agata, E. M., V. Thayer, and W. Schaffner. 2000. An outbreak of *Acinetobacter baumannii* the importance of cross-transmission. *Infect Control Hosp Epidemiol* 21:588-591.

Dizbay, M., O. G. Tunccan, B. E. Sezer, and K. Hizel. 2010. Nosocomial imipenem-resistant *Acinetobacter baumannii* infections: Epidemiology and risk factors. *Scand J Infect Dis*

Doi, Y., S. Husain, B. A. Potoski, K. R. McCurry, and D. L. Paterson. 2009. Extensively drug-resistant *Acinetobacter baumannii*. *Emerg Infect Dis* 15:980-982.

Falagas, M. E., P. I. Rafailidis, D. K. Matthaiou, S. Virtzili, D. Nikita, and A. Michalopoulos. 2008. Pandrug-resistant *Klebsiella pneumoniae, Pseudomonas aeruginosa* and *Acinetobacter baumannii* infections: characteristics and outcome in a series of 28 patients. *Int J Antimicrob Agents* 32:450-454.

Furniss, D., S. Gore, B. Azadian, and S. R. Myers. 2005. *Acinetobacter* infection is associated with acquired glucose intolerance in burn patients. *J Burn Care Rehabil* 26:405-408.

Gordon, N. C., and D. W. Wareham. 2009. A review of clinical and microbiological outcomes following treatment of infections involving multidrug-resistant *Acinetobacter baumannii* with tigecycline. *J Antimicrob Chemother* 63:775-780.

Hernan, R. C., B. Karina, G. Gabriela, N. Marcela, V. Carlos, and F. Angela. 2009. Selection of colistin-resistant *Acinetobacter baumannii* isolates in postneurosurgical meningitis in an intensive care unit with high presence of heteroresistance to colistin. *Diagn Microbiol Infect Dis* 65:188-191.

Hidron, A. I., J. R. Edwards, J. Patel, T. C. Horan, D. M. Sievert, D. A. Pollock, and S. K. Fridkin. 2008. NHSN annual update: antimicrobial-resistant pathogens associated with healthcare-associated infections: annual summary of data reported to the National Healthcare Safety Network at the Centers for Disease Control and Prevention, 2006-2007. *Infect Control Hosp Epidemiol* 29:996-1011.

Higgins, P. G., C. Dammhayn, M. Hackel, and H. Seifert. 2010. Global spread of carbapenem-resistant *Acinetobacter baumannii J Antimicrob Chemother* 65:233-238.

Hoffmann, M. S., M. R. Eber, and R. Laxminarayan. 2010. Increasing resistance of *acinetobacter* species to imipenem in United States hospitals, 1999-2006. *Infect Control Hosp Epidemiol* 31:196-197.

Ibrahim, A. S., J. E. Edwards, Jr., Y. Fu, and B. Spellberg. 2006a. Deferiprone iron chelation as a novel therapy for experimental mucormycosis. *J Antimicrob Chemother* 58:1070-1073.

Ibrahim, A. S., T. Gebermariam, Y. Fu, L. Lin, M. I. Husseiny, S. W. French, J. Schwartz, C. D. Skory, J. E. J. Edwards, and B. Spellberg. 2007. The iron chelator deferasirox protects mice from mucormycosis through iron starvation. *J Clin Invest* 117:2649-2657.

Ibrahim, A. S., B. J. Spellberg, V. Avanesian, Y. Fu, and J. E. J. Edwards. 2006b. The anti-*Candida* rAls1p-N vaccine is broadly active against disseminated candidiasis. *Infect Immun* 74:3039-3041.

Ibrahim, A. S., B. J. Spellberg, V. Avenissian, Y. Fu, S. G. Filler, and J. E. Edwards, Jr. 2005. Vaccination with recombinant N-terminal domain of Als1p improves survival during murine disseminated candidiasis by enhancing cell-mediated, not humoral, immunity. *Infect Immun* 73:999-1005.

Kallen, A. J., A. I. Hidron, J. Patel, and A. Srinivasan. 2010. Multidrug Resistance among Gram-Negative Pathogens Causing Healthcare-Associated Infections Reported to the National Healthcare Safety Network, 2006-2008. *Infect Control Hosp Epidemiol* 31:528-531.

Kim, S. W., C. H. Choi, D. C. Moon, J. S. Jin, J. H. Lee, J. H. Shin, J. M. Kim, Y. C. Lee, S. Y. Seol, D. T. Cho, and J. C. Lee. 2009. Serum resistance of *Acinetobacter baumannii* through the binding of factor H to outer membrane proteins. *FEMS Microbiol Lett* 301:224-231.

King, L. B., E. Swiatlo, A. Swiatlo, and L. S. McDaniel. 2009. Serum resistance and biofilm formation in clinical isolates of *Acinetobacter* baumannii. *FEMS Immunol Med Microbiol* 55:414-421.

Lautenbach, E., M. Synnestvedt, M. G. Weiner, W. B. Bilker, L. Vo, J. Schein, and M. Kim. 2009. Epidemiology and impact of imipenem resistance in *Acinetobacter baumannii*. *Infect Control Hosp Epidemiol* 30:1186-1192.

Lindblad, E. B. 2004a. Aluminium adjuvants—in retrospect and prospect. *Vaccine* 22:3658-3668

Lindblad, E. B. 2004b. Aluminium compounds for use in vaccines. *Immunol Cell Biol* 82:497-505.

Livermore, D. M., R. L. Hill, H. Thomson, A. Charlett, J. F. Turton, R. Pike, B. C. Patel, R. Manuel, S. Gillespie, I.

Balakrishnan, S. P. Barrett, N. Cumberland, and M. Twagira. 2010. Antimicrobial treatment and clinical outcome for infections with carbapenem- and multiply-resistant *Acinetobacter* baumannii around London. *Int J Antimicrob Agents* 35:19-24.

Luo, G., A. S. Ibrahim, B. Spellberg, C. J. Nobile, A. P. Mitchell, and Y. Fu. 2010. *Candida albicans* Hyr1p confers resistance to neutrophil killing and is a potential vaccine target. *J Infect Dis* 201:1718-1728.

McConnell, M. J., J. Dominguez-Herrera, Y. Smani, R. Lopez-Rojas, F. Docobo-Perez, and J. Pachon. 2010. Vaccination with outer membrane complexes elicits rapid protective immunity to multidrug-resistant *Acinetobacter baumannii*. *Infect Immun*

McConnell, M. J., and J. Pachon. 2010a. Active and passive immunization against *Acinetobacter baumannii* using an inactivated whole cell vaccine. *Vaccine* 29:1-5.

McConnell, M. J., and J. Pachon. 2010b. Expression, purification, and refolding of biologically active *Acinetobacter baumannii* OmpA from *Escherichia coli* inclusion bodies. *Protein Expr Purif*

Mera, R. M., L. A. Miller, H. Amrine-Madsen, and D. F. Sahm. 2010. *Acinetobacter baumannii* 2002-2008: Increase of Carbapenem-Associated Multiclass Resistance in the United States. *Microb Drug Resist*

Metan, G., F. Sariguzel, and B. Sumerkan. 2009. Factors influencing survival in patients with multi-drug-resistant *Acinetobacter bacteraemia*. *Eur J Intern Med* 20:540-544.

Molloy, M. P., B. R. Herbert, M. B. Slade, T. Rabilloud, A. S, Nouwens, K. L. Williams, and A. A. Gooley. 2000. Proteomic analysis of the *Escherichia coli* outer membrane. *Eur J Biochem* 267:2871-2881.

Munoz-Price, L. S., T. Zembower, S. Penugonda, P. Schreckenberger, M. A. Lavin, S. Welbel, D. Vais, M. Baig, S. Mohapatra, J. P. Quinn, and R. A. Weinstein. 2010. Clinical Outcomes of Carbapenem-Resistant *Acinetobacter baumannii* Bloodstream Infections: Study of a 2-State Monoclonal Outbreak. *Infect Control Hosp Epidemiol*

Park, Y. K., S. I. Jung, K. H. Park, H. S. Cheong, K. R. Peck, J. H. Song, and K. S. Ko. 2009. Independent emergence of colistin-resistant *Acinetobacter* spp. isolates from Korea. *Diagn Microbiol Infect Dis* 64:43-51.

Perez, F., A. M. Hujer, K. M. Hujer, B. K. Decker, P. N. Rather, and R. A. Bonomo. 2007. Global challenge of multidrug-resistant *Acinetobacter baumannii*. *Antimicrob Agents Chemother* 51:3471-3484.

Perez, F., A. M. Hujer, E. A. Hulten, J. Fishbain, K. M. Hujer, D. Aron, K. Thweatt, C. J. Donskey, and R. A. Bonomo. 2010. Antibiotic resistance determinants in *Acinetobacter* spp and clinical outcomes in patients from a major military treatment facility. *Am J Infect Control* 38:63-65.

Piechaud, M., and L. Second. 1951. [Studies of 26 strains of *Moraxella* Iwoffi]. *Ann Inst Pasteur (Paris)* 80:97-99.

Pitarch, A., A. Jimenez, C. Nombela, and C. Gil. 2006. Decoding serological response to *Candida* cell wall immunome into novel diagnostic, prognostic, and therapeutic candidates for systemic candidiasis by proteomic and bioinformatic analyses. *Mol Cell Proteomics* 5:79-96.

Pitarch, A., M. Pardo, A. Jimenez, J. Pla, C. Gil, M. Sanchez, and C. Nombela. 1999. Two-dimensional gel electrophoresis as analytical tool for identifying *Candida albicans* immunogenic proteins. *Electrophoresis* 20:1001-1010.

Qiu, H., R. Kuolee, G. Harris, and W. Chen. 2009. Role of NADPH phagocyte oxidase in host defense against acute respiratory *Acinetobacter baumannii* infection in mice. *Infect Immun* 77:1015-1021.

Rosenthal, V. D., D. G. Maki, S. Jamulitrat, E. A. Medeiros, S. K. Todi, D. Y. Gomez, H. Leblebicioglu, I. Abu Khader, M. G. Miranda Novales, R. Berba, F. M. Ramirez Wong, A. Barkat, O. R. Pino, L. Duenas, Z. Mitrev, H. Bijie, V. Gurskis, S. S. Kanj, T. Mapp, R. F. Hidalgo, N. Ben Jaballah, L. Raka, A. Gikas, A. Ahmed, L. T. Thu, M. E. Guzman Siritt, and I. Members. 2010. International Nosocomial Infection Control Consortium (INICC) report, data summary for 2003-2008, issued June 2009. *Am J Infect Control* 38:95-104 e102.

Russo, T. A., J. M. Beanan, R. Olson, U. MacDonald, N. R. Luke, S. R. Gill, and A. A. Campagnari. 2008. Rat pneumonia and soft-tissue infection models for the study of *Acinetobacter baumannii* biology. *Infect Immun* 76:3577-3586.

Russo, T. A., U. MacDonald, J. M. Beanan, R. Olson, I. J. MacDonald, S. L. Sauberan, N. R. Luke, L. W. Schultz, and T. C. Umland. 2009. Penicillin-binding protein 7/8 contributes to the survival of *Acinetobacter baumannii* in vitro and in vivo. *J Infect Dis* 199:513-521.

Shevchenko, A., O. N. Jensen, A. V. Podtelejnikov, F. Sagliocco, M. Wilm, O. Vorm, P. Mortensen, H. Boucherie, and M. Mann. 1996a Linking genome and proteome by mass spectrometry: large-scale identification of yeast proteins from two dimensional gels. *Proc Natl Acad Sci USA* 93:14440-14445.

Shevchenko, A., M. Wilm, O. Vorm, and M. Mann. 1996b. Mass spectrometric sequencing of proteins silver-stained polyacrylamide gels. *Anal Chem* 68:850-858.

Smolinski, M. S., M. A. Hamburg, and J. Lederberg, editors. 2003. Microbial Threats to Health: Emergence, Detection, and Response. The Institute of Medicine, Washington D.C.

Soares, N. C., M. P. Cabral, J. R. Parreira, C. Gayoso, M. J. Barba, and G. Bou. 2009. 2-DE analysis indicates that *Acinetobacter baumannii* displays a robust and versatile metabolism. *Proteome Sci* 7:37.

Spellberg, B., M. Blaser, R. Guidos, H. W. Boucher, B. J. S., B. Eisenstein, D. Gerding, R. Lynfield, L. B. Reller, J. Rex, D. Schwartz, E. Septimus, F. C. Tenover, and D. N. Gilbert. 2011. for the Infectious Diseases Society of America. Combating Antimicrobial Resistance Policy Recommendations to Save Lives. *Clin Infect Dis* 52(55):397-428.

Spellberg, B., Y. Fu, J. E. Edwards, Jr., and A. S. Ibrahim. 2005a. Combination therapy with amphotericin B lipid complex and caspofungin acetate of disseminated zygomycosis in diabetic ketoacidotic mice. *Antimicrob Agents Chemother* 49:830-832.

Spellberg, B., R. Guidos, D. Gilbert, J. Bradley, H. W. Boucher, W. M. Scheld, J. G. Bartlett, and J. Edwards, Jr. 2008a. The epidemic of antibiotic-resistant infections: a call to action for the medical community from the Infectious Diseases Society of America. *Clin Infect Dis* 46:155-164.

Spellberg, B., A. S. Ibrahim, M. Yeaman, L. Lin, Y. Fu, V. Avanesian, A. S. Bayer, S. G. Filler, P. Lipke, H. Otoo, and J. E. Edwards. 2008b. The anti-fungal rAls3p-N vaccine protects mice against the bacterium *Staphylococcus aureus*. *Infect Immun* 76:4574-4580.

Spellberg, B. J., A. S. Ibrahim, V. Avanesian, Y. Fu, C. Myers, Q. T. Phan, S. G. Filler, M. R. Yeaman, and J. E. J. Edwards. 2006. Efficacy of the anti-Candida rAls3p-N or rAls1p-N vaccines against disseminated and mucosal candidiasis. *J Infect Dis* 194:256-260.

Spellberg, B. J., A. S. Ibrahim, V. Avenissian, S. G. Filler, C. L. Myers, Y. Fu, and J. E. Edwards, Jr. 2005b. The anti-*Candida albicans* vaccine composed of the recombinant N terminus of Als1p reduces fungal burden and improves survival in both immunocompetent and immunocompromised mice. *Infect Immun* 73:6191-6193.

Sunenshine, R. H., M. O. Wright, L. L. Maragakis, A. D. Harris, X. Song, J. Hebden, S. E. Cosgrove, A. Anderson, J. Carnell, D. B. Jernigan, D. G. Kleinbaum, T. M. Perl, H. C. Standiford, and A. Srinivasan. 2007. Multidrug-resistant *Acinetobacter* infection mortality rate and length of hospitalization. *Emerg Infect Dis* 13:97-103.

Tian, G. B., J. M. Adams-Haduch, T. Bogdanovich, A. W. Pasculle, J. P. Quinn, H. N. Wang, and Y. Doi. 2011. Identification of diverse OXA-40 group carbapenemases, including a novel variant, OXA-160, from *Acinetobacter baumannii* in Pennsylvania. *Antimicrob Agents Chemother* 55:429-432.

Tseng, Y. C., J. T. Wang, F. L. Wu, Y. C. Chen, W. C. Chie, and S. C. Chang. 2007. Prognosis of adult patients with bacteremia caused by extensively resistant *Acinetobacter baumannii*. *Diagn Microbiol Infect Dis* 59:181-190.

Valencia, R., L. A. Arroyo, M. Conde, J. M. Aldana, M. J. Torres, F. Fernandez-Cuenca, J. Garnacho-Montero, J. M. Cisneros, C. Ortiz, J. Pachon, and J. Aznar. 2009. Nosocomial outbreak of infection with pan-drug-resistant *Acinetobacter baumannii* in a tertiary care university hospital. *Infect Control Hosp Epidemiol* 30:257-263.

van Faassen, H., R. KuoLee, G. Harris, X. Zhao, J. W. Conlan, and W. Chen. 2007. Neutrophils play an important role in host resistance to respiratory infection with *Acinetobacter baumannii* in mice. *Infect Immun* 75:5597-5608.

Walker, B., S. Barrett, S. Polasky, V. Galaz, C. Folke, G. Engstrom, F. Ackerman, K. Arrow, S. Carpenter, K. Chopra, G. Daily, P. Ehrlich, T. Hughes, N. Kautsky, S. Levin, K. G. Maler, J. Shogren, J. Vincent, T. Xepapadeas, and A. de Zeeuw. 2009. Environment. Looming global-scale failures and missing institutions. *Science* 325:1345-1346.

Wang, Y. F., and M. J. Dowzicky. 2010. In vitro activity of tigecycline and comparators on *Acinetobacter* spp. isolates collected from patients with bacteremia and MIC change during the Tigecycline Evaluation and Surveillance Trial, 2004 to 2008. *Diagn Microbiol Infect Dis* 68:73-79.

Zakuan, Z. D., H. Azian, O. Mahamarowi, and J. Md Radzi. 2009. The prevalence and risk factors of nosocomial *Acinetobacter* blood stream infections in tertiary teaching hospital in north-eastern Malaysia. *Trop Biomed* 26:123-129.

---

What is claimed is:

1. A composition comprising an isolated antibody, or antigen binding fragment thereof, wherein said antibody or antigen binding fragment specifically binds to an epitope of *A. baumannii* outer membrane protein A (OmpA), wherein said epitope consists of at least 10 but less than 25 amino acids in length and an amino acid sequence of SEQ ID NO:1 that comprises the aspartic acid at position 123, the aspartic acid at position 125, and the asparagine at position 128.

2. The composition of claim 1, further comprising a pharmaceutically acceptable carrier.

3. The composition of claim 1, wherein said epitope consists of at least 10 but less than 20 amino acids in length.

4. The composition of claim 1, wherein said epitope consists of at least 10 but less than 15 amino acids in length.

* * * * *